US010854315B2

(12) United States Patent
Kyriazopoulou-Panagiotopoulou et al.

(10) Patent No.: US 10,854,315 B2
(45) Date of Patent: Dec. 1, 2020

(54) SYSTEMS AND METHODS FOR DETERMINING STRUCTURAL VARIATION AND PHASING USING VARIANT CALL DATA

(71) Applicant: 10X Genomics, Inc., Pleasanton, CA (US)

(72) Inventors: Sofia Kyriazopoulou-Panagiotopoulou, Pleasanton, CA (US); Patrick Marks, San Francisco, CA (US); Michael Schnall-Levin, Pleasanton, CA (US); Xinying Zheng, Pleasanton, CA (US); Mirna Jarosz, Pleasanton, CA (US); Serge Saxonov, Oakland, CA (US); Kristina Giorda, San Mateo, CA (US); Patrice Mudivarti, Berkeley, CA (US); Heather Ordonez, Oakland, CA (US); Jessica Terry, Pleasanton, CA (US); William Haynes Heaton, Pleasanton, CA (US)

(73) Assignee: 10X Genomics, Inc., Pleasanton, CA (US)

( * ) Notice: Subject to any disclaimer, the term of this patent is extended or adjusted under 35 U.S.C. 154(b) by 1285 days.

(21) Appl. No.: 15/019,928

(22) Filed: Feb. 9, 2016

(65) Prior Publication Data

US 2016/0232291 A1 Aug. 11, 2016

Related U.S. Application Data

(63) Continuation of application No. PCT/US2016/017196, filed on Feb. 9, 2016.

(60) Provisional application No. 62/238,077, filed on Oct. 6, 2015, provisional application No. 62/120,247, filed on Feb. 24, 2015, provisional application No. 62/120,330, filed on Feb. 24, 2015, provisional application No. 62/113,693, filed on Feb. 9, 2015.

(51) Int. Cl.
*G16B 30/00* (2019.01)
*G16B 20/00* (2019.01)

(52) U.S. Cl.
CPC ............ *G16B 30/00* (2019.02); *G16B 20/00* (2019.02)

(58) Field of Classification Search
None
See application file for complete search history.

(56) References Cited

U.S. PATENT DOCUMENTS

| 5,149,625 | A | 9/1992 | Church et al. |
|---|---|---|---|
| 5,202,231 | A | 4/1993 | Drmanac et al. |
| 5,413,924 | A | 5/1995 | Kosak et al. |
| 5,436,130 | A | 7/1995 | Mathies et al. |
| 5,512,131 | A | 4/1996 | Kumar et al. |
| 5,587,128 | A | 12/1996 | Wilding et al. |
| 5,605,793 | A | 2/1997 | Stemmer |
| 5,618,711 | A | 4/1997 | Gelfand et al. |
| 5,695,940 | A | 12/1997 | Drmanac et al. |
| 5,736,330 | A | 4/1998 | Fulton |
| 5,834,197 | A | 11/1998 | Parton |
| 5,851,769 | A | 12/1998 | Gray et al. |
| 5,856,174 | A | 1/1999 | Lipshutz et al. |
| 5,958,703 | A | 9/1999 | Dower et al. |
| 5,994,056 | A | 11/1999 | Higuchi |
| 6,046,003 | A | 4/2000 | Mandecki |
| 6,051,377 | A | 4/2000 | Mandecki |
| 6,057,107 | A | 5/2000 | Fulton |
| 6,103,537 | A | 8/2000 | Ullman et al. |
| 6,143,496 | A | 11/2000 | Brown et al. |
| 6,172,218 | B1 | 1/2001 | Brenner |
| 6,297,006 | B1 | 10/2001 | Drmanac et al. |
| 6,297,017 | B1 | 10/2001 | Thompson |

(Continued)

FOREIGN PATENT DOCUMENTS

| EP | 0249007 A2 | 12/1987 |
|---|---|---|
| EP | 0637996 B1 | 7/1997 |

(Continued)

OTHER PUBLICATIONS

Browning, S. R. et al; "Haplotype phasing: existing methods and new developments"; Nature Reviews Genetics; vol. 12; Oct. 2011; p. 703-714. (Year: 2011).*
"Bedtools: General Usage," http://bedtools.readthedocs.io/en/latest/content/generalusage.html; Retrieved from the Internet Jul. 8, 2016, p. 1-9.
Bray, "The JavaScript Object Notation (JSON) Data Interchange Format," Mar. 2014, retrieved from the Internet Feb. 15, 2015; https://tools.ietf.org/html/rfc7159.
Gordon et al., 1998, "Consed: A Graphical Tool for Sequence Finishing," Genome Research 8:198-202.

(Continued)

*Primary Examiner* — Lori A. Clow
*Assistant Examiner* — Marie Archer
(74) *Attorney, Agent, or Firm* — Morgan, Lewis & Bockius LLP

(57) ABSTRACT

Systems and methods for determining structural variation and phasing using variant call data obtained from nucleic acid of a biological sample are provided. Sequence reads are obtained, each comprising a portion corresponding to a subset of the test nucleic acid and a portion encoding a barcode independent of the sequencing data. Bin information is obtained. Each bin represents a different portion of the sample nucleic acid. Each bin corresponds to a set of sequence reads in a plurality of sets of sequence reads formed from the sequence reads such that each sequence read in a respective set of sequence reads corresponds to a subset of the nucleic acid represented by the bin corresponding to the respective set. Binomial tests identify bin pairs having more sequence reads with the same barcode in common than expected by chance. Probabilistic models determine structural variation likelihood from the sequence reads of these bin pairs.

30 Claims, 44 Drawing Sheets

(56) References Cited

U.S. PATENT DOCUMENTS

| | | |
|---|---|---|
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,406,848 B1 | 6/2002 | Bridgham et al. |
| 6,432,360 B1 | 8/2002 | Church |
| 6,485,944 B1 | 11/2002 | Church et al. |
| 6,511,803 B1 | 1/2003 | Church et al. |
| 6,524,456 B1 | 2/2003 | Ramsey et al. |
| 6,586,176 B1 | 7/2003 | Trnovsky et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,323,305 B2 | 1/2008 | Leamon et al. |
| 7,425,431 B2 | 9/2008 | Church et al. |
| 7,536,928 B2 | 5/2009 | Kazuno |
| 7,604,938 B2 | 10/2009 | Takahashi et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,708,949 B2 | 5/2010 | Stone et al. |
| 7,709,197 B2 | 5/2010 | Drmanac |
| 7,745,178 B2 | 6/2010 | Dong |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,067,159 B2 | 11/2011 | Brown et al. |
| 8,133,719 B2 | 3/2012 | Drmanac et al. |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,304,193 B2 | 11/2012 | Ismagilov et al. |
| 8,329,407 B2 | 12/2012 | Ismagilov et al. |
| 8,337,778 B2 | 12/2012 | Stone et al. |
| 8,592,150 B2 | 11/2013 | Drmanac et al. |
| 8,603,749 B2 | 12/2013 | Gillevet |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagliov et al. |
| 8,871,444 B2 | 10/2014 | Griffiths et al. |
| 8,889,083 B2 | 11/2014 | Ismagilov et al. |
| 9,012,370 B2 | 4/2015 | Hong |
| 9,017,948 B2 | 4/2015 | Agresti et al. |
| 9,029,083 B2 | 5/2015 | Griffiths et al. |
| 9,347,059 B2 | 5/2016 | Saxonov |
| 9,388,465 B2 | 7/2016 | Hindson et al. |
| 9,410,201 B2 | 8/2016 | Hindson et al. |
| 9,694,361 B2 | 7/2017 | Bharadwaj |
| 9,695,468 B2 | 7/2017 | Hindson et al. |
| 9,824,068 B2 | 11/2017 | Wong et al. |
| 10,119,167 B2 | 11/2018 | Srinivasan et al. |
| 10,221,442 B2 | 3/2019 | Hindson et al. |
| 2001/0020588 A1 | 9/2001 | Adourian et al. |
| 2001/0044109 A1 | 11/2001 | Mandecki |
| 2002/0034737 A1 | 3/2002 | Drmanac |
| 2002/0051992 A1 | 5/2002 | Bridgham et al. |
| 2002/0089100 A1 | 7/2002 | Kawasaki |
| 2002/0092767 A1 | 7/2002 | Bjornson et al. |
| 2002/0179849 A1 | 12/2002 | Maher et al. |
| 2003/0008285 A1 | 1/2003 | Fischer |
| 2003/0008323 A1 | 1/2003 | Ravkin et al. |
| 2003/0027221 A1 | 2/2003 | Scott et al. |
| 2003/0028981 A1 | 2/2003 | Chandler et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0104466 A1 | 6/2003 | Knapp et al. |
| 2003/0108897 A1 | 6/2003 | Drmanac |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0132122 A1 | 7/2004 | Banerjee et al. |
| 2004/0258701 A1 | 12/2004 | Dominowski et al. |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0287572 A1 | 12/2005 | Mathies et al. |
| 2006/0020371 A1 | 1/2006 | Ham et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0054119 A1 | 3/2007 | Garstecki et al. |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0111241 A1 | 5/2007 | Cereb et al. |
| 2007/0154903 A1 | 7/2007 | Marla et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0213766 A1 | 9/2008 | Brown et al. |
| 2008/0241820 A1 | 10/2008 | Krutzik et al. |
| 2008/0268431 A1 | 10/2008 | Choy et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0098555 A1 | 4/2009 | Roth et al. |
| 2009/0118488 A1 | 5/2009 | Drmanac et al. |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |

(56) References Cited

U.S. PATENT DOCUMENTS

| | | |
|---|---|---|
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0264299 A1 | 10/2009 | Drmanac et al. |
| 2009/0286687 A1 | 11/2009 | Dressman et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0069263 A1 | 3/2010 | Shendure et al. |
| 2010/0105112 A1 | 4/2010 | Holtze et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston et al. |
| 2010/0210479 A1 | 8/2010 | Griffiths et al. |
| 2010/0216153 A1 | 8/2010 | Lapidus et al. |
| 2011/0033854 A1 | 2/2011 | Drmanac et al. |
| 2011/0053798 A1 | 3/2011 | Hindson et al. |
| 2011/0071053 A1 | 3/2011 | Drmanac et al. |
| 2011/0086780 A1 | 4/2011 | Colston et al. |
| 2011/0092376 A1 | 4/2011 | Colston et al. |
| 2011/0092392 A1 | 4/2011 | Colston et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0217736 A1 | 9/2011 | Hindson |
| 2011/0218123 A1 | 9/2011 | Weitz et al. |
| 2011/0257889 A1 | 10/2011 | Klammer et al. |
| 2011/0263457 A1 | 10/2011 | Krutzik et al. |
| 2011/0267457 A1 | 11/2011 | Weitz et al. |
| 2011/0281738 A1 | 11/2011 | Drmanac et al. |
| 2011/0305761 A1 | 12/2011 | Shum et al. |
| 2011/0319281 A1 | 12/2011 | Drmanac |
| 2012/0000777 A1 | 1/2012 | Garrell et al. |
| 2012/0010098 A1 | 1/2012 | Griffiths et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0041727 A1 | 2/2012 | Mishra et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0172259 A1 | 7/2012 | Rigatti et al. |
| 2012/0184449 A1 | 7/2012 | Hixson et al. |
| 2012/0190032 A1 | 7/2012 | Ness et al. |
| 2012/0196288 A1 | 8/2012 | Beer |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0230338 A1 | 9/2012 | Ganeshalingam et al. |
| 2012/0309002 A1 | 12/2012 | Link |
| 2012/0316074 A1 | 12/2012 | Saxonov |
| 2013/0028812 A1 | 1/2013 | Prieto et al. |
| 2013/0046030 A1 | 2/2013 | Rotem et al. |
| 2013/0078638 A1 | 3/2013 | Berka et al. |
| 2013/0079231 A1 | 3/2013 | Pushkarev et al. |
| 2013/0109575 A1 | 5/2013 | Kleinschmidt et al. |
| 2013/0130919 A1 | 5/2013 | Chen et al. |
| 2013/0157870 A1 | 6/2013 | Pushkarev et al. |
| 2013/0157899 A1 | 6/2013 | Adler et al. |
| 2013/0178368 A1 | 7/2013 | Griffiths et al. |
| 2013/0185096 A1 | 7/2013 | Giusti et al. |
| 2013/0189700 A1 | 7/2013 | So et al. |
| 2013/0203605 A1 | 8/2013 | Shendure et al. |
| 2013/0210639 A1 | 8/2013 | Link et al. |
| 2013/0225418 A1 | 8/2013 | Watson |
| 2013/0268206 A1 | 10/2013 | Porreca et al. |
| 2013/0274117 A1 | 10/2013 | Church et al. |
| 2013/0311106 A1 | 11/2013 | White et al. |
| 2013/0317755 A1 | 11/2013 | Mishra et al. |
| 2014/0037514 A1 | 2/2014 | Stone et al. |
| 2014/0057799 A1 | 2/2014 | Johnson et al. |
| 2014/0065234 A1 | 3/2014 | Shum et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0200166 A1 | 7/2014 | Van Rooyen et al. |
| 2014/0206554 A1 | 7/2014 | Hindson et al. |
| 2014/0214334 A1 | 7/2014 | Plattner et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0287963 A1 | 9/2014 | Hindson et al. |
| 2014/0302503 A1 | 10/2014 | Lowe et al. |
| 2014/0323316 A1 | 10/2014 | Drmanac et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov |
| 2015/0066385 A1 | 3/2015 | Schnall-Levin et al. |
| 2015/0111256 A1 | 4/2015 | Church et al. |
| 2015/0133344 A1 | 5/2015 | Shendure et al. |
| 2015/0218633 A1 | 8/2015 | Hindson et al. |
| 2015/0220532 A1 | 8/2015 | Wong |
| 2015/0224466 A1 | 8/2015 | Hindson et al. |
| 2015/0225777 A1 | 8/2015 | Hindson et al. |
| 2015/0225778 A1 | 8/2015 | Hindson et al. |
| 2015/0292988 A1 | 10/2015 | Bharadwaj et al. |
| 2015/0298091 A1 | 10/2015 | Weitz et al. |
| 2015/0299772 A1 | 10/2015 | Zhang |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0304860 A1 | 10/2016 | Hindson et al. |
| 2016/0350478 A1 | 12/2016 | Chin et al. |
| 2017/0235876 A1 | 8/2017 | Jaffe et al. |
| 2018/0196781 A1 | 7/2018 | Wong |
| 2018/0265928 A1 | 9/2018 | Schnall-Levin et al. |

FOREIGN PATENT DOCUMENTS

| | | |
|---|---|---|
| EP | 1019496 B1 | 9/2004 |
| EP | 1482036 B1 | 10/2007 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| GB | 2485850 A | 5/2012 |
| JP | 5949832 A | 3/1984 |
| JP | 2006-507921 A | 3/2006 |
| JP | 2006-289250 A | 10/2006 |
| JP | 2007-268350 A | 10/2007 |
| JP | 2009-208074 | 9/2009 |
| JP | 2012525147 A | 10/2012 |
| RU | 2321638 C2 | 4/2008 |
| WO | WO-1996029629 A2 | 9/1996 |
| WO | WO-1996041011 A1 | 12/1996 |
| WO | WO-1999009217 A1 | 2/1999 |
| WO | WO-1999052708 A1 | 10/1999 |
| WO | WO-2000008212 A1 | 2/2000 |
| WO | WO-2000026412 A1 | 5/2000 |
| WO | WO-2001014589 A2 | 3/2001 |
| WO | WO-2001089787 A2 | 11/2001 |
| WO | WO-2002031203 A2 | 4/2002 |
| WO | WO-2002086148 A1 | 10/2002 |
| WO | WO-2004002627 A2 | 1/2004 |
| WO | WO-2004010106 A2 | 1/2004 |
| WO | WO-2004069849 A2 | 8/2004 |
| WO | WO-2004091763 A2 | 10/2004 |

(56) References Cited

FOREIGN PATENT DOCUMENTS

| WO | WO-2004102204 A1 | 11/2004 |
|---|---|---|
| WO | WO-2004103565 A2 | 12/2004 |
| WO | WO-2004105734 A1 | 12/2004 |
| WO | WO-2005002730 A1 | 1/2005 |
| WO | WO-2005021151 A1 | 3/2005 |
| WO | WO-2005023331 A2 | 3/2005 |
| WO | WO-2005040406 A1 | 5/2005 |
| WO | WO-2005049787 A9 | 6/2005 |
| WO | WO-2005082098 A2 | 9/2005 |
| WO | WO-2006030993 A1 | 3/2006 |
| WO | WO-2006078841 A1 | 7/2006 |
| WO | WO-2006096571 A2 | 9/2006 |
| WO | WO-2007001448 A2 | 1/2007 |
| WO | WO-2007002490 A2 | 1/2007 |
| WO | WO-2007024840 A2 | 3/2007 |
| WO | WO-2007081385 A2 | 7/2007 |
| WO | WO-2007081387 A1 | 7/2007 |
| WO | WO-2007089541 A2 | 8/2007 |
| WO | WO-2007114794 A1 | 10/2007 |
| WO | WO-2007121489 A2 | 10/2007 |
| WO | WO-2007133710 A2 | 11/2007 |
| WO | WO-2007138178 A2 | 12/2007 |
| WO | WO-2007139766 A2 | 12/2007 |
| WO | WO-2007140015 A2 | 12/2007 |
| WO | WO-2007149432 A2 | 12/2007 |
| WO | WO-2008021123 A1 | 2/2008 |
| WO | WO-2008091792 A2 | 7/2008 |
| WO | WO-2008102057 A1 | 8/2008 |
| WO | WO-2008109176 A2 | 9/2008 |
| WO | WO-2008121342 A2 | 10/2008 |
| WO | WO-2008134153 A1 | 11/2008 |
| WO | WO-2009005680 A1 | 1/2009 |
| WO | WO-2009011808 A1 | 1/2009 |
| WO | WO 2009/023821 A1 | 2/2009 |
| WO | WO-2009061372 A1 | 5/2009 |
| WO | WO-2009085215 A1 | 7/2009 |
| WO | WO-2010004018 A2 | 1/2010 |
| WO | WO-2010033200 A2 | 3/2010 |
| WO | WO-2010115154 A1 | 10/2010 |
| WO | WO-2010127304 A2 | 11/2010 |
| WO | WO-2010148039 A2 | 12/2010 |
| WO | WO-2010151776 A2 | 12/2010 |
| WO | WO-2011047870 A1 | 4/2011 |
| WO | WO-2011056546 A1 | 5/2011 |
| WO | WO-2011066476 A1 | 6/2011 |
| WO | WO-2011074960 A1 | 6/2011 |
| WO | WO-2012012037 A1 | 1/2012 |
| WO | WO-2012048341 A1 | 4/2012 |
| WO | WO 2012/061832 A1 | 5/2012 |
| WO | WO-2012055929 A1 | 5/2012 |
| WO | WO 2012/100216 A2 | 7/2012 |
| WO | 2012112804 A1 | 8/2012 |
| WO | WO-2012106546 A2 | 8/2012 |
| WO | WO-2012116331 A2 | 8/2012 |
| WO | WO-2012083225 A2 | 9/2012 |
| WO | WO 2012/142531 A2 | 10/2012 |
| WO | WO 2012/142611 A2 | 10/2012 |
| WO | WO-2012149042 A2 | 11/2012 |
| WO | WO-2012166425 A2 | 12/2012 |
| WO | WO-2013035114 A1 | 3/2013 |
| WO | 2013055955 A1 | 4/2013 |
| WO | WO-2013123125 A1 | 8/2013 |
| WO | WO-2013177220 A1 | 11/2013 |
| WO | WO-2014028537 A1 | 2/2014 |
| WO | WO 2014/093676 A1 | 6/2014 |
| WO | WO 2015/157567 A1 | 10/2015 |
| WO | WO 2015/200891 A1 | 12/2015 |
| WO | WO-2016130578 A1 | 8/2016 |

OTHER PUBLICATIONS

Huang and Marth, 2008, "EagleView: A genome assembly viewer for next-generation sequencing technologies," Genome Research 18:1538-1543.

International Search Report for International Patent Application No. PCT/US2016/013290, dated May 19, 2016, 11 pages.

"SSH Tunnel—Local and Remote Port Forwarding Explained With Examples," Trackets Blog, http://blog.trackets.com/2014/05/17/ssh-tunnel-local-and-remote-port-forwarding-explained-with-examples.html; Retrieved from the Internet Jul. 7, 2016, p. 1-3.

Wheeler et al., 2007, "Database resources of the National Center for Biotechnology Information," Nucleic Acids Res. 35 (Database issue): D5-12.

International Search Report for International Patent Application No. PCT/US2016/017196, dated May 29, 2016, 14 pages.

Bansal et al., "HapCUT: an efficient and accurate algorithm for the haplotype assembly problem," Bioinformatics, vol. 24, 2008, pp. i153-i159.

Bansal et al., 2008, "An MCMC algorithm for haplotype assembly from whole-genome sequence data," Genome Res, 18:1336-1346.

Bentley et al., 2008, Accurate whole human genome sequencing using reversible terminator chemistry, Nature 456:53-59.

Browning et al., "Haplotype phasing: Existing methods and new developments," Nat Rev Genet., 12(10), Apr. 1, 2012, pp. 703-714.

Chen et al., 2009, "BreakDancer: an algorithm for high-resolution mapping of genomic structural variation," Nature Methods 6(9), pp. 677-681.

Choi et al., 2008, "Identification of novel isoforms of the EML4-ALK transforming gene in non-small cell lung cancer," Cancer Res, 68:4971-4976.

Cleary et al., 2014, "Joint variant and de novo mutation identification on pedigrees from high-throughput sequencing data," J Comput Biol, 21:405-419.

"Real-time DNA sequencing from single polymerase molecules" Eid et al., "Real-time sequencing form single polymerase molecules," Science 323:133-138, 2009.

Heng and Durbin, 2010, "Fast and accurate long-read alignment with Burrows-Wheeler transform," Bioinformatics, 25(14): 1754-1760.

Kanehisa and Goto, 2000, "KEGG: Kyoto Encyclopedia of Genes and Genomes," Nucleic Acids Research 28, 27-30.

Kim et al., "HapEdit: an accuracy assessment viewer for haplotype assembly using massively parallel DNA-sequencing technologies," Nucleic Acids Research, 2011, pp. 1-5.

Kirkness et al., 2013, "Sequencing of isolated sperm cells for direct haplotyping of a human genome," Genome Res, 23:826-832.

Kitzman et al., 2011, "Haplotype-resolved genome sequencing of a Gujarati Indian individual." Nat Biotechnol, 29:59-63.

Layer et al., 2014, "LUMPY: A probabilistic framework for structural variant discovery," Genome Biology 15(6):R84.

Lippert et al., 2002, "Algorithmic strategies for the single nucleotide polymorphism haplotype assembly problem," Brief. Bionform 3:23-31.

Margulies et al., 2005, "Genome sequencing in microfabricated high-density picoliter reactors," Nature 437:376-380.

McKenna et al., "The Genome Analysis Toolkit: A MapReduce framework for anaylzing next-generation DNA sequencing data," Genome Research, 2010, pp. 1297-1303.

Miller et al., "Assembly Algorithms for next-generation sequencing data," Genomics, 95 (2010), pp. 315-327.

Myllykangas et al., 2011, "Efficient targeted resequencing of human germline and cancer genomes by oligonucleotide-selective sequencing," Nat Biotechnol, 29:1024-1027.

Pushkarev et al., 2009, "Single-molecule sequencing of an individual human genome," Nature Biotech 17:847-850.

Shendure et al., 2005, "Accurate Multiplex Polony Sequencing of an Evolved bacterial Genome" Science 309:1728-1732.

Tewhey et al., 2011, "The importance of phase information for human genomics," Nat Rev Genet, 12:215-223.

The SAM/BAM Format Specificatio Working Group, "Sequence Allignment/ Map Format Specification," Dec. 28, 2014, p. 1-22.

Zerbino et al., "Velvet: Algorithms for de novo short read assembly using de Bruijn graphs," Genome Research 18, 2008, pp. 821-829.

Zerbino, Daniel, "Velvet Manual—version 1.1," Aug. 15, 2008, pp. 1-22.

Abate et al., Valve-based flow focusing for drop formation. Appl Phys Lett. 2009;94. 3 pages.

(56) References Cited

OTHER PUBLICATIONS

Abate, A.R. et al. "Beating Poisson encapsulation statistics using close-packed ordering" Lab on a Chip (Sep. 21, 2009) 9(18):2628-2631.
Abate, et al. High-throughput injection with microfluidics using picoinjectors. Proc Natl Acad Sci U S A. Nov. 9, 2010;107(45):19163-6. doi: 10.1073-pNas.1006888107. Epub Oct. 20, 2010.
Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.
Aitman, et al. Copy number polymorphism in Fcgr3 predisposes to glomerulonephritis in rats and humans. Nature. Feb. 16, 2006;439(7078):851-5.
Akselband, "Enrichment of slow-growing marine microorganisms from mixed cultures using gel microdrop (GMD) growth assay and fluorescence-activated cell sorting", J. Exp. Marine Biol., 329: 196-205 (2006).
Akselband, "Rapid mycobacteria drug susceptibility testing using gel microdrop (GMD) growth assay and flow cytometry", J. Microbiol. Methods, 62:181-197 (2005).
Anna et al., "Formation of dispersions using 'flow focusing' in microchannels", Appln. Phys. Letts. 82:3 364 (2003).
Attia, U.M et al., "Micro-injection moulding of polymer microfluidic devices" Microfluidics and nanofluidics (2009) 7(1):1-28.
Balikova, et al. Autosomal-dominant microtia linked to five tandem copies of a copy-number-variable region at chromosome 4p16. Am J Hum Genet. Jan. 2008;82(1):181-7. doi: 10.1016-j.ajhg.2007.08.001.
Baret et al. "Fluorescence-activated droplet sorting (FADS): efficient microfluidic cell sorting based on enzymatic activity" Lab on a Chip (2009) 9(13):1850-1858.
Boone, et al. Plastic advances microfluidic devices. The devices debuted in silicon and glass, but plastic fabrication may make them hugely successful in biotechnology application. Analytical Chemistry. Feb. 2002; 78A-86A.
Braeckmans et al., Scanning the Code. Modern Drug Discovery. 2003:28-32.
Bransky, et al. A microfluidic droplet generator based on a piezoelectric actuator. Lab Chip. Feb. 21, 2009;9(4):516-20. doi: 10.1039-b814810d. Epub Nov. 20, 2008.
Brouzes, E et al., "Droplet microfluidic technology for single-cell high-throughput screening" PNAS (2009) 106(34):14195-14200.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Carroll, "The selection of high-producing cell lines using flow cytometry and cell sorting", Exp. Op. Bioi. Therp., 4:11 1821-1829 (2004).
Chaudhary "A rapid method of cloning functional variable-region antibody genes in *Escherichia coli* as single-chain immunotoxins" Proc. Nat!. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101.
Chen, F et al., "Chemical transfection of cells in picoliter aqueous droplets in fluorocarbon oil" Anal. Chem. (2011) 83:8816-8820.
Chokkalingam, V et al., "Probing cellular heterogeneity in cytokine-secreting immune cells using droplet-based microfluidics" Lab Chip (2013) 13:4740-4744.
Chou, H-P. et al. "Disposable Microdevices for DNA Analysis and Cell Sorting" Proc. Solid-State Sensor and Actuator Workshop Hilton Head, SC Jun. 8-11, 1998, pp. 11-14.
Chu, L-Y. et al., "Controllable monodisperse multiple emulsions" Angew. Chem. Int. Ed. (2007) 46:8970-8974.
Clausell-Tormos et al., "Droplet-based microfluidic platforms for the encapsulation and screening of mammalian cells and multicellular organisms", Chem. Biol. 15:427-437 (2008).

Cook, et al. Copy-number variations associated with neuropsychiatric conditions. Nature. Oct. 16, 2008;455(7215):919-23. doi: 10.1038-nature07458.
De Bruin et al., UBS Investment Research. Q-Seriesï163 $^1$/2 : DNa Sequencing. UBS Securities LLC. Jul. 12, 2007. 15 pages.
Demirci, et al. "Single cell epitaxy by acoustic picolitre droplets" Lab Chip. Sep. 2007;7(9):1139-45. Epub Jul. 10, 2007.
Doerr, "The smallest bioreactor", Nature Methods, 2:5 326 (2005).
Dowding, et al. "Oil core-polymer shell microcapsules by interNal phase separation from emulsion droplets. II: controlling the release profile of active molecules" Langmuir. Jun. 7, 2005;21(12):5278-84.
Draper, M.C. et al., "Compartmentalization of electrophoretically separated analytes in a multiphase microfluidic platform" Anal. Chem. (2012) 84:5801-5808.
Dressler, O.J. et al., "Droplet-based microfluidics enabling impact on drug discovery" J. Biomol. Screen (2014) 19(4):483-496.
Drmanac et al., Sequencing by hybridization (SBH): advantages, achievements, and opportunities. Adv Biochem Eng Biotechnol. 2002;77 :75-101.
Droplet Based Sequencing (slides) dated (Mar. 12, 2008), p. 427-437.
Eastburn, D.J. et al., "Ultrahigh-throughput mammalian single-cell reverse-transcriptase polymerase chain reaction in microfluidic droplets" Anal. Chem. (2013) 85:8016-8021.
Esser-Kahn, et al. Triggered release from polymer capsules. Macromolecules. 2011; 44:5539-5553.
Fabi, et al. Correlation of efficacy between EGFR gene copy number and lapatinib-capecitabine therapy in HER2-positive metastatic breast cancer. J. Clin. Oncol. 2010; 28:15S. 2010 ASCO Meeting abstract Jun. 14, 2010:1059.
Fisher, S. et al. "A Scalable, fully automated process for construction of sequence-ready human exome targeted capture libraries" Genome Biology (2011) 2:R1-R15. doi: 10.1186-gb-2011-12-1-r1. Epub Jan. 4, 2011.
Fredrickson, C.K. et al., "Macro-to-micro interfaces for microfluidic devices" Lab Chip (2004) 4:526-533.
Freiberg, et al. "Polymer microspheres for controlled drug release" Int J Pharm. Sep. 10, 2004;282(1-2):1-18.
Fu. A.Y. et al. "A microfabricated fluorescence-activated cell sorter" Nature Biotech (Nov. 1999) 17:1109-1111.
Fulton et al., "Advanced multiplexed analysis with the FlowMetrix system" Clin Chern. Sep. 1997;43(9): 1749-56.
Garstecki, P. et al. "Formation of monodisperse bubbles in a microfluidic flow-focusing device" Appl. Phys. Lett (2004) 85(13):2659-2651. DOI: 10.1063-1.1796526.
Gartner, et al. The Microfluidic Toolbox ï¿$^4$/2 examples for fluidic interfaces and standardization concepts. Proc. SPIE 4982, Microfluidics, BioMEMS, and Medical Microsystems, (Jan. 17, 2003); doi: 10.1117-12.479566, 6 pages.
Ghadessy, et al. Directed evolution of polymerase function by compartmentalized self-replication. Proc Natl Acad Sci U S A. Apr. 10, 2001;98(8):4552-7. Epub Mar. 27, 2001.
Gonzalez, et al. The influence of CCL3L1 gene-containing segmental duplications on HIV-1-AIDS susceptibility. Science. Mar. 4, 2005;307(5714):1434-40. Epub Jan. 6, 2005.
Granieri, Lucia "Droplet-based microfluidics and engineering of tissue plasminogen activator for biomedical applications" Ph.D. Thesis, Nov. 13, 2009 (131 pages).
Guo, M.T. et al., "Droplet microfluidics for high-throughput biological assays" Lab Chip (2012) 12:2146-2155.
Gyarmati et al., "Reversible Disulphide Formation in Polymer Networks: A Versitile Functional Group from Synthesis to Application," European Polymer Journal, 2013, 49, 1268-1286.
Hashimshony, T et al. "CEL-Seq: Single-Cell RNa-Seq by Multiplexed Linear Amplification" Cell Rep. Sep. 27, 2012;2(3):666-73. doi: 10.1016-j.celrep.2012.08.003. Epub Aug. 30, 2012.
He "Selective Encapsulation of Single Cells and Subcellular Organelles into Picoliter- and Femtoliter-Volume Droplets" Anal. Chern 77: 1539-1544 (2005).
Holtze, C. et al. Biocompatible surfactants for water-in-fluorocarbon emulsions. Lab Chip. Oct. 2008;8(10):1632-9. doi: 10.1039-b806706f. Epub Sep. 2, 2008.

(56) References Cited

OTHER PUBLICATIONS

Huebner, "Quantitative detection of protein expression in single cells using droplet microfluidics", Chem. Commun. 1218-1220 (2007).
Hug, H. et al. "Measurement of the number of molecules of a single mRNA species in a complex mRNA preparation" J Theor Biol. Apr. 21, 2003;221(4):615-24.
Illumina, Inc. An Introduction to Next-Generation Sequencing Technology. Feb. 28, 2012, 12 pages.
Jena et al., "Cyclic olefin copolymer based microfluidic devices for biochip applications: Ultraviolet surface grafting using 2-methacryloyloxyethyl phosphorylchloline" Biomicrofluidics (Mar. 15, 2012) 6:012822 (12 pages).
Jung, W-C et al., "Micromachining of injection mold inserts for fluidic channel of polymeric biochips" Sensors (2007) 7:1643-1654.
Khomiakov A et al., "Analysis of perfect and mismatched DNA duplexes by a generic hexanucleotide microchip". Mol Bioi (Mosk). Jul.-Aug. 2003;37(4):726-41. Russian. Abstract only.
Kim, et al. Albumin loaded microsphere of amphiphilic poly(ethylene glycol)- poly(alpha-ester) multiblock copolymer. Eur J Pharm Sci. Nov. 2004;23(3):245-51.
Kim, et al. Fabrication of monodisperse gel shells and functioNal microgels in microfluidic devices. Angew Chem Int Ed Engl. 2007;46(11):1819-22.
Kim, J et al., "Rapid prototyping of microfluidic systems using a PDMS-polymer tape composite" Lab Chip (2009) 9:1290-1293.
Kitzman, et al. Noninvasive whole-genome sequencing of a human fetus. Sci Transl Med. Jun. 6, 2012;4(137):137ra76. doi: 10.1126-scitranslmed.3004323.
Klein, et al. Droplet barcoding for single-cell transcriptomics applied to embryonic stem cells. Cell. May 21, 2015; 161:1187-1201.
Knight, et al. Subtle chromosomal rearrangements in children with unexplained mental retardation. Lancet. Nov. 13, 1999;354(9191):1676-81.
Koster et al., "Drop-based microfluidic devices for encapsulation of single cells", Lab on a Chip The Royal Soc. of Chem. 8: 1110-1115 (2008).
Kutyavin, et al. Oligonucleotides containing 2-aminoadenine and 2-thiothymine act as selectively binding complementary agents. Biochemistry. Aug. 27, 1996;35(34):11170-6.
Lagus, T.P. et al., "A review of the theory, methods and recent applications of high-throughput single-cell droplet microfluidics" J. Phys. D: Appl. Phys. (2013) 46:114005 (21 pages).
Li, Y., et al., "PEGylated PLGA Nanoparticles as protein carriers: synthesis, preparation and biodistribution in rats," Journal of Controlled Release, vol. 71, pp. 203-211 (2001).
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Loscertales, I.G., et al., "Micro-Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24(6):703-707 (Jun. 2006).
Lowe, Adam J."Norbornenes and [n]polynorbornanes as molecular scaffolds for anion recognition" Ph.D. Thesis (May 2010). (361 pages).
Lupski. Genomic rearrangements and sporadic disease. Nat Genet. Jul. 2007;39(7 Suppl):S43-7.
Macosko, et al. Highly Parallel Genome-wide Expression Profiling of Individual Cells Using Nanoliter Droplets. Cell. May 21, 2015;161(5):1202-14. doi: 10.1016-j.cell.2015.05.002.
Mair, D.A. et al., "Injection molded microfluidic chips featuring integrated interconnects" Lab Chip (2006) 6:1346-1354.
Makino, K. et al. "Preparation of hydrogel microcapsules Effects of preparation conditions upon membrane properties" Colloids and Surfaces: B Biointerfaces (1998) 12:97-104.

Marcus. Gene method offers diagnostic hope. The Wall Street Journal. Jul. 11, 2012, 3 pages.
Matochko, W.L. et al., "Uniform amplification of phage display libraries in monodisperse emulsions," Methods (2012) 58:18-27.
Mazutis, et al. Selective droplet coalescence using microfluidic systems. Lab Chip. Apr. 24, 2012;12(10):1800-6. doi: 10.1039-c2lc40121e. Epub Mar. 27, 2012.
Merriman, et al. Progress in ion torrent semiconductor chip based sequencing. Electrophoresis. Dec. 2012;33(23):3397-3417. doi: 10.1002-elps.201200424.
Microfluidic ChipShop. Microfluidic product catalogue. Oct. 2009, 48 pages.
Mirzabekov, "DNA Sequencing by Hybridization—a Megasequencing Method and A Diagnostic Tool?" Trends in Biotechnology 12(1): 27-32 (1994).
Moore, J.L. et al., "Behavior of capillary valves in centrifugal microfluidic devices prepared by three-dimensional printing" Microfluid Nanofluid (2011) 10:877-888.
Mouritzen et al., Single nucleotide polymorphism genotyping using locked nucleic acid (LNa). Expert Rev Mol Diagn. Jan. 2003;3(1):27-38.
Nagashima, S. et al. "Preparation of monodisperse poly(acrylamide-co-acrylic acid) hydrogel microspheres by a membrane emulsification technique and their size dependent surface properties" Colloids and Surfaces: B Biointerfaces (1998) 11:47-56.
Navin, N.E. "The first five years of single-cell cancer genomics and beyond" Genome Res. (2015) 25:1499-1507.
Nguyen, et al. In situ hybridization to chromosomes stabilized in gel microdrops. Cytometry. 1995; 21:111-119.
Novak, R. et al., "Single cell multiplex gene detection and sequencing using microfluidicallygenerated agarose emulsions" Angew. Chem. Int. Ed. Engl. (2011) 50(2):390-395.
Oberholzer, et al. Polymerase chain reaction in liposomes. Chem Biol. Oct. 1995;2(10):677-82.
Ogawa, et al. Production and characterization of O-W emulsions containing cationic droplets stabilized by lecithin-chitosan membranes. J Agric Food Chem. Apr. 23, 2003;51(9):2806-12.
Okushima, "Controlled production of monodisperse double emulsions by two-step droplet breakup in microfluidic devices", Langmuir, 20:9905-9908 (2004).
Perez, C., et al., "Poly(lactic acid)-poly(ethylene glycol) Nanoparticles as new carriers for the delivery ofplasmid DNa," Journal of Controlled Release, vol. 75, pp. 211-224 (2001).
Peters et al., "Accurate whole-genome sequencing and haplotyping from 10 to 20 human cells," Nature, Jul. 12, 2012, vol. 487, pp. 190-195.
Pinto, et al. Functional impact of global rare copy number variation in autism spectrum disorders. Nature. Jul. 15, 2010;466(7304):368-72. doi: 10.1038-nature09146. Epub Jun. 9, 2010.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Ropers. New perspectives for the elucidation of genetic disorders. Am J Hum Genet. Aug. 2007;81(2):199-207. Epub Jun. 29, 2007.
Rotem, A. et al. "Single Cell Chip-Seq Using Drop-Based Microfluidics" Abstract #50. Frontiers of Single Cell Analysis, Stanford University Sep. 5-7, 2013, 1 page.
Rotem, A. et al., "High-throughput single-cell labeling (Hi-SCL) for RNA-Seq using drop-based microfluidics" PLOS One (May 22, 2015) 0116328 (14 pages).
Ryan, et al. Rapid assay for mycobacterial growth and antibiotic susceptibility using gel microdrop encapsulation. J Clin Microbiol. Jul. 1995;33(7):1720-6.
Schirinzi et al., Combinatorial sequencing-by-hybridization: analysis of the NFI gene. Genet Test. 2006 Spring;10(1):8-17.
Schmitt, "Bead-based multiplex genotyping of human papillomaviruses", J. Clinical Microbiol., 44:2 504-512 (2006).
Sebat, et al. Strong association of de novo copy number mutations with autism. Science. Apr. 20, 2007;316(5823):445-9. Epub Mar. 15, 2007.
Seiffert, S. et al., "Smart microgel capsules from macromolecular precursors" J. Am. Chem. Soc. (2010) 132:6606-6609.

(56) References Cited

OTHER PUBLICATIONS

Shah, "Fabrication of mono disperse thermosensitive microgels and gel capsules in micro fluidic devices", Soft Matter, 4:2303-2309 (2008).
Shimkus et al. "A chemically cleavable biotinylated nucleotide: Usefulness in the recovery of protein-DNA complexes from avidin affinity columns" PNAS (1985) 82:2593-2597.
Shlien, et al. Copy number variations and cancer. Genome Med. Jun. 16, 2009;1(6):62. doi: 10.1186-gm62.
Shlien, et al. Excessive genomic DNA copy number variation in the Li-Fraumeni cancer predisposition syndrome. Proc Natl Acad Sci U S A Aug. 12, 2008;105(32):11264-9. doi: 10.1073-pnas.0802970105. Epub Aug. 6, 2008.
Simeonov et al., Single nucleotide polymorphism genotyping using short, fluorescently labeled locked nucleic acid (LNa) probes and fluorescence polarization detection. Nucleic Acids Res. Sep. 1, 2002;30(17):e91.
Sorokin et al., Discrimination between perfect and mismatched duplexes with oligonucleotide gel microchips: role of thermodyNamic and kinetic effects during hybridization. J Biomol Struct Dyn. Jun. 2005;22(6):725-34.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Tawfik, D.S. et al. "Man-made cell-like compartments for molecular evolution" Nature Biotech (Jul. 1998) 16:652-656.
Tewhey, R. et al., "Microdroplet-based PCR enrichment for large-scale targeted sequencing" Nature Biotech. (2009) 27(11):1025-1031 and Online Methods (11 pages).
Theberge, A.B, et al. Microdropelts in microfluidics: an evolving platform for discoveries in chemsitry and biology. Angew Chem Int Ed Engl. Aug. 9, 2010;49(34):5846-68. doi: 10.1002-anie.200906653.
Tonelli, C. et al., "Perfluoropolyether functional oligomers: unusual reactivity in organic chemistry" J. Fluorine Chem. (2002) 118:107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093-protein-gzq032. Epub May 31, 2010.
Turner, et al. "Methods for genomic partitioning" Annu Rev Genomics Human Genet. (2009) 10:263-284. doi: 10.1146-annurev-genom-082908-150112. Review.
Wagner, O et al., "Biocompatible fluorinated polyglycerols for droplet microfluidics as an alternative to PEG-based copolymer surfactants" Lab Chip DOI:10.1039-05LC00823A. 2015, 6 pages.
Wang et al., Single nucleotide polymorphism discrimination assisted by improved base stacking hybridization using oligonucleotide microarrays. Biotechniques. 2003;35:300-08.
Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci U S A. Dec. 10, 2002;99(25):16156-61. Epub Dec. 2, 2002
Weaver, J.C. et al. "Rapid clonal growth measurements at the single-cell level: gel microdroplets and flow cytometry", Biotechnology, 9:873-877 (1991).
Whitesides, "Soft lithography in biology and biochemistry", Annual Review of Biomedical Engineering, 3:335-373 (2001).
Williams, R. et al. "Amplification of complex gene libraries by emulsion PCR" Nature Methods (Jul. 2006) 3(7):545-550.
Woo, et al. G-C-modified oligodeoxynucleotides with selective complementarity: synthesis and hybridization properties. Nucleic Acids Res. Jul. 1, 1996;24(13):2470-5.
Xia, "Soft lithography", Annual Review of Material Science, 28: 153-184 (1998).
Yamamoto, et al. Chemical modification of Ce(IV)-EDTA-base artificial restriction DNa cutter for versatile manipulation of doulbe-stranded DNa. Nucleic Acids Research. 2007; 35(7):e53.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functioNalized nucleosides via the RAFT process. Biomacromolecules. Nov. 2008;9(11):3321-31. doi: 10.1021-bm800867n. Epub Oct. 9, 2008.
Zhao, J., et al., "Preparation of hemoglobin-loaded Nano-sized particles with porous structure as oxygen carriers," Biomaterials, vol. 28, pp. 1414-1422 (2007).
Zhu, S. et al., "Synthesis and self-assembly of highly incompatible polybutadienepoly(hexafluoropropoylene oxide) diblock copolymers" J. Polym. Sci. (2005) 43:3685-3694.
Zimmermann et at., Microscale production of hybridomas by hypo-osmolar electrofusion. Human Antibodies Hybridomas. Jan. 1992; 3(1 ): 14-8.
Zong, C. et al. "Genome-wide detection of single-nucleotide and copy-number variations of a single human cell" Science. Dec. 21, 2012;338(6114):1622-6. doi: 10.1126-science.1229164.
Margulies 2005 Supplementary methods (Year: 2005).
Ekblom, R. et al. "A field guide to whole-genome sequencing, assembly and annotation" Evolutionary Apps (Jun. 24, 2014) 7(9):1026-1042.
Jarosz, M. et al. "Using 1ng of DNA to detect haplotype phasing and gene fusions from whole exome sequencing of cancer cell lines" Cancer Res (2015) 75(supp15):4742.
Lo, et al. On the design of clone-based haplotyping. Genome Biol. 2013;14(9):R100.
McCoy, R. et al. "Illumina TruSeq Synthetic Long-Reads Empower De Novo Assembly and Resolve Complex, Highly-Repetitive Transposable Elements" PLOS (2014) 9(9):e1016689.
Ritz, A. et al. "Characterization of structural variants with single molecule and hybrid sequencing approaches" Bioinformatics (2014) 30(24):3458-3466.
Voskoboynik, A. et al. "The genome sequence of the colonial chordate, Botryllus schlosseri." eLife Jul. 2, 2013, 2:e00569.
Zerbino, D.R. "Using the Velvet de novo assembler for short-read sequencing technologies" Curr Protoc Bioinformatics (Sep. 1, 2010), Chapter 11: Unit 11.5; 12 pages.
Zheng, X.Y. et al. "Haplotyping germline and cancer genomes with high-throughput linked-read sequencing" Nature Biotech (Feb. 1, 2016) 34(3):303-311 and Supplemental Material.
Extended European Search Report for EP Application No. 16749735.3, dated Jul. 10, 2018, 9 pages.
Zheng, X. SeqArray: an R/Bioconductor Package for Big Data Management of Genome-Wide Sequencing Variants, Department of Biostatistics, University of Washington, Dec. 28, 2014, 34 pages.
Co-pending U.S. Appl. No. 15/242,256, filed Aug. 19, 2016.
Grasland-Mongrain, E. et al. "Droplet coalescence in microlfuidic devices" Internet Citation, 2003, XP002436104, Retrieved from the Internet: URL:http:--www.eleves.ens.fr.-home-grasland-rapports-stage4.pdf [retrieved on Jun. 4, 2007], 31 pages.
Microfluidic ChipShop. Microfluidic product catalogue. Mar. 2005, 18 pages.

* cited by examiner

744 — Responsive to a determination that the first value satisfies a predetermined cut-off value, for each barcode that is common to the first bin and the second bin, obtain a fragment pair thereby obtaining one or more fragment pairs. Each fragment pair in the one or more fragment pairs (i) corresponds to a different barcode that is common to the first bin and the second bin and (ii) consists of a different first calculated fragment and a different second calculated fragment. For each respective fragment pair in the one or more fragment pairs the different first calculated fragment consists of a respective first subset of sequence reads in the plurality of sequence reads having the barcode corresponding to the respective fragment pair. Each sequence read in the respective first subset of sequence reads is within a predefined genetic distance of another sequence read in the respective first subset of sequence reads. The different first calculated fragment of the respective fragment pair originates with a first sequence read having the barcode corresponding to the respective fragment pair in the first bin. Each sequence read in the respective first subset of sequence reads is from the first bin. The different second calculated fragment consists of a respective second subset of sequence reads in the plurality of sequence reads having the barcode corresponding to the respective fragment pair. Each sequence read in the respective second subset of sequence reads is within a predefined genetic distance of another sequence read in the respective second subset of sequence reads. The different second calculated fragment of the respective fragment pair originates with a second sequence read having the barcode corresponding to the respective fragment pair in the second bin, and each sequence read in the respective second subset of sequence reads is from the second bin.

746 — The single biological sample is human, the test nucleic acid is the genome of the biological sample, and the first value satisfies the predetermined cut-off value when the first value is $10^{-12}$ or less, when the first value is $10^{-13}$ or less, when the first value is $10^{-14}$ or less, or when the first value is $10^{-15}$ or less.

748 — An identity of the first and second bin is determined using sparse matrix multiplication.

Figure 7D

$$P(r_1, r_2, l_1, l_2, d \mid \text{no } SV; a_b) =$$
$$P(r_1, r_2, l_1, l_2, d \mid SM, \text{no } SV; a_b) P(SM \mid \text{no } SV)$$
$$+ P(r_1, r_2, l_1, l_2, d \mid DM, \text{no } SV; a_b) P(DM \mid \text{no } SV)$$

where,
  *SM* is the hypothesis that the first calculated molecule and the second calculated molecule originated from the same fragment of the test nucleic acid in the plurality of sequence reactions,
  *DM* is the hypothesis that the first calculated molecule and the second calculated molecule originated from different fragments of the test nucleic acid in the plurality of sequencing reactions.
  $P_{frag}(r_1, l_1; a_b)$ is the probability of observing $r_1$ reads from a second molecule of unknown length such that the reads span an observed length of $l_1$, and
  is the probability of observing $r_2$ reads from a second molecule of unknown length such that the reads span an observed length of $l_2$.

---

$P_{frag}(r_1, l_1; a_b)$ and $P_{frag}(r_2, l_2; a_b)$ are each computed as $$\sum_{m: m \geq l} \left( r(r-1) \left(\frac{l}{m}\right)^{r-2} \frac{m-l}{m^2} \right) P_p(r; m a_b) P_L(m)$$
$$= \sum_{m: m \geq l} (m - l) P_p(r - 2; a_b l) P_p(0; a_b(m - l)) a_b^2 P_L(m)$$

where $P_p(r; b)$ is the probability mass function of a Poisson distribution with parameter b, and $P_L(m)$ is the (pre-estimated) probability that the true molecule length of the respective molecule is m.

---

$P(r_1, r_2, l_1, l_2, d \mid SM, \text{no } SV; a_b)$ is computed as $$\sum_{m: m \geq l_1 + l_2 + d} (m - l_1 - l_2 - d) P_p(r_1 - 2; a_b l_1) P_p(r_2 - 2; a_b l_2) P_p(0; a_b(m - l_1 - l_2)) a_b^4 P_L(m)$$

where m is length of the true molecule length, $P_p(r_1 - 2; a_b l_1)$ is a probability mass function of a Poisson distribution with parameter b for $r_1$, $P_p(r_2 - 2; a_b l_2)$ and $r_2$, $P_p(0; a_b(m - l_1 - l_2))$ are each probability mass functions of a Poisson distribution with parameter b, and $P_L(m)$ is a pre-estimated probability that the true common molecule length is m.

- 768 — The structural variation is an insertion or deletion of 50 consecutive bases or more, 500 consecutive bases or more, or 5000 consecutive bases or more, into the different portion of the test nucleic acid that is represented by the first set of sequence reads.

- 770 — The different portion of the test nucleic acid of the first bin overlaps the different portion of the test nucleic acid represented by the second bin.

- 772 — At least 50, 80 percent, or 95 percent of the different portion of the test nucleic acid of the first bin overlaps the different portion of the test nucleic acid of the second bin.

- 774 — The structural variation is a translocation of 50 consecutive bases or more into the different portion of the test nucleic acid that is represented by the first set of sequence reads from the different portion of the test nucleic acid that is represented by the second set of sequence reads.

- 776 — The different portion of the test nucleic acid represented by the bin corresponding to the first set of sequence reads is from a first chromosome of the biological sample, and the different portion of the test nucleic acid represented by the bin corresponding to the second set of sequence reads is from a second chromosome of the biological sample, where the second chromosome is other than the first chromosome.

- 778 — The first chromosome is a paternal chromosome and the second chromosome is a maternal chromosome.

- 780 — The biological sample is human and the first chromosome is any of chromosome 1-21.

- 782 — The structural variation is deemed to have occurred, the method further comprising treating a subject that originated the biological sample with a treatment regimen responsive to the structural variation.

- 784 — The treatment regimen comprises a diet modification.

- 786 — The treatment regimen comprises application of a pharmaceutical composition that inhibits a biological pathway associated with the structural variation.

- 788 — Maintaining a blackout list, the blackout list comprising a plurality of blackout regions of the test nucleic acid, and the method further comprises eliminating a sequence read, prior to the identifying, from the number of respective sequence reads when the first portion of the sequence read overlaps a blackout region in the plurality of blackout regions.

Figure 7H

| Metric | NA12878 WGS | NA12878 WES |
|---|---|---|
| Input Material | 1 ng | 1 ng |
| Mean Coverage | 23x | 139x |
| Mapped Read Fraction | 97% | 99% |
| PCR Duplication Rate | 0.8% | 4.7% |
| Barcode Diversity | >100k | >100k |
| N50 Linked Reads / Molecule | 66 | 37 |
| Mean Molecule Length (Length Weighted) | 61.3 kb | 64.7 kb |

Figure 10

$$\log P(O_{t,f}|A_{t,p}) = \sum_r \mathbf{1}(S_r = A_{t,p})(1 - 10^{-Q_r/10}) + \mathbf{1}(S_r \neq A_{t,p})(10^{-Q_r/10})$$

$$P(O_{1,f},\ldots O_{N,f}|\mathbf{X}) = \frac{(1-\alpha)}{2}\left(\prod_i P(O_{t,f}|A_{t,x_i}) + \prod_i P(O_{t,f}|A_{t,1-x_i})\right) + \alpha\prod_i 0.5$$

$$P(\mathbf{O}|\mathbf{X}) = \prod_f P(O_{1,f},\ldots O_{N,f}|\mathbf{X})$$

Figure 12

| Metric | NA12878 WGS | HuRef 1 WGS | NA20847 WGS | NA12878 WES |
|---|---|---|---|---|
| Mean Coverage | 23x | 23x | 23x | 139x |
| N50 Phase Block | 2.3 MB | 1.2MB | 1.6MB | 306KB |
| Short Switch | 0.25% | 0.4% | 1.4% | 0.24% |
| Long Switch | 0.016% | 0.017% | 0.08% | 0.03% |
| % SNPs Phased | 97.2% | 94.6% | 97.4% | 95.5% |
| % Genes Fully Phased (<100kb) | 95.9% | 90.0% | 92.3% | 96.1% |

Figure 14

| Chrom1 | Start1 | Chrom2 | Start2 | Phase Set | BCs Intersecting Hap1 | BCs Intersecting Hap2 | P | Deleted Haplotype | Deletion Inherited by NA12882 | Phasing Consistent with Inheritance |
|---|---|---|---|---|---|---|---|---|---|---|
| chr1 | 189704495 | chr1 | 189783155 | 50188502070 | 57 | 4 | 4.90E-13 | 1 | No | Yes |
| chr3 | 162512117 | chr3 | 162626153 | 190161712492 | 2 | 57 | 6.10E-15 | 2 | Yes | Yes |
| chr5 | 104432082 | chr5 | 104503476 | 27098341819 | 5 | 28 | 6.60E-05 | 2 | Yes | Yes |
| chr6 | 78967148 | chr6 | 79036215 | 31076466627 | 45 | 7 | 7.00E-08 | 1 | No | Yes |
| chr6 | 78967148 | chr6 | 79036215 | 310789671164 | 50 | 2 | 6.10E-13 | 1 | No | Yes |
| chr8 | 39232044 | chr8 | 39386994 | 39030957010 | 45 | 0 | 5.70E-14 | 1 | Yes | Yes |
| chr8 | 39232044 | chr8 | 39386994 | 39039370800 | 46 | 0 | 2.80E-14 | 1 | Yes | Yes |
| chr5 | 99400840 | chr5 | 99714778 | 27098341819 | 97 | 87 | 0.51 | FP | No | N/A |
| chr14 | 376315990 | chr14 | 377771213 | 62033781205 | 2 | 8 | 0.11 | FP | No | N/A |
| chr14 | 106932612 | chr14 | 107174772 | 640106692870 | 10 | 13 | 0.68 | FP | No | N/A |

Figure 16

| Sample Description | Sample name | Input mass (ng) | Mean Dup Rate | Mean Depth | % genes phased (<100kb) | Longest Phase Block (MB) |
|---|---|---|---|---|---|---|
| Acute Promyelocytic Leukemia | ACC207 | 1 | 1.09 | 178 | 91.4 | 1.2 |
| Triple negative breast cancer | HCC38 | 1 | 1.13 | 173 | 93.7 | 1.5 |
| Matched normal | HCC38BL | 1 | 1.08 | 81 | 90.7 | 0.8 |
| Triple negative breast cancer | HCC1143 | 1 | 1.13 | 176 | 95.5 | 1.1 |
| Matched normal | HCC1143BL | 1 | 1.07 | 100 | 93.8 | 0.6 |
| Colorectal adenocarcinoma | HCT-15 | 1 | 1.09 | 140 | 91.9 | 1.8 |
| Non-small cell lung cancer | NCI-H2228 | 1 | 1.05 | 159 | 91.3 | 0.6 |

Figure 19

| Sample description | Sample name | Input mass (ng) | Mean Dup rate | Mean Depth | Longest phase block (Mb) | Gene Fusion(s) Annotated | Detected |
|---|---|---|---|---|---|---|---|
| Acute promyelocytic leukemia | ACC207 | 1 | 1.07 | 132 | 1.2 | PML-RARA | Yes |
| Triple negative breast cancer | HCC38 | 1 | 1.1 | 123 | 1.5 | LDHC-SERGF | Yes |
| | | | | | | MBOAT2-PRKCE | Yes |
| | | | | | | CUTA-SLC22A1 | Yes |
| | | | | | | SLC6A6-PRKAR2A | Yes |
| | | | | | | ABCD6-RRP15 | No |
| Triple negative breast cancer | HCC1143 | 1 | 1.08 | 99 | 1.1 | FAM65B-MIPEP | Yes |
| | | | | | | GCNT2-C6ORF52 | Yes |
| | | | | | | MCF2L2 - NRG2 | No |
| Non-small cell lung cancer | NCI-H2228 | 1 | 1.05 | 159 | 0.6 | EML4-ALK | Yes |
| | | | | | | ALK-PTPN3 | Yes |

Figure 20

| Fusion | Pos1 | Pos2 | Phase Block | #BC's in SV | #BC's, hap1 | #BC's, hap2 | p |
|---|---|---|---|---|---|---|---|
| EML4/ALK | Chr2: 29,447,360 | Chr2: 42,499,30 | Chr2:29,225,502-29,446,202 | 25 | 0 | 23 | 2.40E-07 |
| ALK/PTPN3 | Chr2: 29,498,180 | Chr9: 112,204,017 | Chr9:112,184,972-112,225,774 | 30 | 0 | 22 | 4.80E-07 |

Figure 24

| | Bases on Target | Fragments on Target | 5' gene | 3' gene | SV Quality Score |
|---|---|---|---|---|---|
| 0.2 fmol Intronic bait | 0.55 | 0.94 | BCR | ABL1 | 35 |
| No intronic bait | 0.56 | 0.95 | BCR | ABL1 | 0 |

Figure 30

SYSTEMS AND METHODS FOR DETERMINING STRUCTURAL VARIATION AND PHASING USING VARIANT CALL DATA

CROSS REFERENCE TO RELATED APPLICATIONS

This application claims priority to U.S. Provisional Patent Application 62/238,077, entitled "Systems and Methods for Determining Structural Variation Using Probabilistic Models," filed Oct. 6, 2015, which is hereby incorporated by reference in its entirety.

This application also claims priority to U.S. Provisional Patent Application 62/113,693, entitled "Systems and Methods for Determining Structural Variation," filed Feb. 9, 2015, which is hereby incorporated by reference in its entirety.

This application also claims priority to U.S. Provisional Patent Application 62/120,247, entitled "Systems and Methods for Implementing Linked Read Algorithms for Haplotype Phasing and Structural Variant Detection," filed Feb. 24, 2015, which is hereby incorporated by reference in its entirety.

This application also claims priority to U.S. Provisional Patent Application 62/120,330, entitled "Detecting Structural Variants and Phasing Haplotypes from Cancer Exome Sequencing Using 1 ng Dna Input," filed Feb. 24, 2015, which is hereby incorporated by reference in its entirety.

This application also claims priority to International Patent Application PCT/US2016/017196, entitled "Systems and Methods for Determining Structural Variation and Phasing Using Variant Call Data," filed Feb. 9, 2016, which is hereby incorporated by reference in its entirety.

TECHNICAL FIELD

This specification describes technologies relating to haplotype phasing and structural variant detection using nucleic acid sequencing data.

BACKGROUND

Haplotype assembly from experimental data obtained from human genomes sequenced using massively parallelized sequencing methodologies has emerged as a prominent source of genetic data. Such data serves as a cost-effective way of implementing genetics based diagnostics as well as human disease study, detection, and personalized treatment.

The long-range information provided by platforms such as those disclosed in U.S. Patent Application No. 62/072,214, filed Oct. 29, 2014, entitled "Analysis of Nucleic Acid Sequences" greatly facilitates the detection of large-scale structural variations of the genome, such as translocations, large deletions, or gene fusions. Other examples include, but are not limited to the sequencing-by-synthesis platform (ILLUMINA), Bentley et al., 2008, "Accurate whole human genome sequencing using reversible terminator chemistry, Nature 456:53-59; sequencing-by-litigation platforms (POLONATOR; ABI SOLiD), Shendure et al., 2005, "Accurate Multiplex Polony Sequencing of an Evolved bacterial Genome" Science 309:1728-1732; pyrosequencing platforms (ROCHE 454), Margulies et al., 2005, "Genome sequencing in microfabricated high-density picoliter reactors," Nature 437:376-380; and single-molecule sequencing platforms (HELICOS HELISCAPE); Pushkarev et al., 2009, "Single-molecule sequencing of an individual human genome," Nature Biotech 17:847-850, (PACIFIC BIOSCIENCES) Eid et al., "Real-time sequencing form single polymerase molecules," Science 323:133-138, each of which is hereby incorporated by reference in its entirety.

Several algorithms have been developed for detecting such events from whole genome sequencing (WGS) data. See, for example, Chen et al., 2009, "BreakDancer: an algorithm for high-resolution mapping of genomic structural variation," Nature Methods 6(9), pp, 677-681 and Layer et al., 2014, "LUMPY: A probabilistic framework for structural variant discovery," Genome Biology 15(6):R84. The goal of these algorithms is to detect the endpoints of structural variants (e.g., the endpoints of a deletion or a gene fusion). These endpoints are also referred to as "breakpoints" and the terms endpoints and breakpoints are used interchangeably. In order to detect breakpoints, existing algorithms rely on the detection of read pairs that are mapped to the genome at unexpected orientations with respect to each other or at unexpected distances (too far from each other or too close to each other relative to the insert size). This implies that, in order for the breakpoint to be detected by conventional algorithms, it must be spanned by read pairs. This limitation makes existing algorithms not applicable to targeted sequencing data, such as whole exome sequencing (WES) data. This is because the breakpoints would be spanned by read pairs only if they were very close to the target regions. This is usually not the case. For example many gene fusions in cancer happen on gene introns rather than exons, so they would not be detectable with WES.

The availability of haplotype data spanning large portions of the human genome, the need has arisen for ways in which to efficiently work with this data in order to advance the above stated objectives of diagnosis, discovery, and treatment, particularly as the cost of whole genome sequencing for a personal genome drops below $1000. To computationally assemble haplotypes from such data, it is necessary to disentangle the reads from the two haplotypes present in the sample and infer a consensus sequence for both haplotypes. Such a problem has been shown to be NP-hard. See Lippert et al., 2002, "Algorithmic strategies for the single nucleotide polymorphism haplotype assembly problem," Brief. Bionform 3:23-31, which is hereby incorporated by reference.

Given the above background, what is needed in the art are improved systems and methods for haplotype phasing and structural variant detection using sequencing data from parallelized sequencing methodologies.

SUMMARY

Technical solutions (e.g., computing systems, methods, and non-transitory computer readable storage mediums) for identifying structural variations and for haplotype phasing are provided. With platforms such as those disclosed in U.S. Provisional Patent Application No. 62/072,214, filed Oct. 29, 2014, entitled "Analysis of Nucleic Acid Sequences," or U.S. Provisional Patent Application 62/113,693, entitled "Systems and Methods for Determining Structural Variation," filed Feb. 9, 2015, each of which is hereby incorporated by reference, the genome is fragmented and partitioned and barcoded prior to the target identification. Therefore the integrity of the barcode information is maintained across the genome. The barcode information is used to identify potential structural variation breakpoints by detecting regions of the genome that show significant barcode overlap. They are also used to obtain phasing information.

The following presents a summary of the invention in order to provide a basic understanding of some of the aspects of the invention. This summary is not an extensive overview of the invention. It is not intended to identify key/critical elements of the invention or to delineate the scope of the invention. Its sole purpose is to present some of the concepts of the invention in a simplified form as a prelude to the more detailed description that is presented later.

Various embodiments of systems, methods and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various embodiments are used.

Part A, Structural Variation.

In some implementations, there is provided a method of detecting a structural variant in sequencing data of a test nucleic acid obtained from a biological sample. The method comprises performing certain operations at a computer system having one or more processors and memory storing one or more programs for execution by the one or more processors. A plurality of sequence reads is obtained. Each respective sequence read in the plurality of sequence reads comprises a first portion that corresponds to a subset of the test nucleic acid and a second portion that encodes an barcode for the respective sequence read. As used herein, the terms "sequence read" and "sequencing read" are used interchangeably. The barcode is independent of the sequencing data of the test nucleic acid. In some embodiments, a first sequence read in the plurality of sequence reads is from a subset of the test nucleic acid that is greater than 10 kilobase pairs (kbp), 20 kbp, 30 kbp, 40 kbp, 50 kbp, 60 kbp, 70 kbp, 80 kbp, 90 kbp, or 100 kbp. In some embodiments, a first sequence read in the plurality of sequence reads is 2×36 bp, 2×50 bp, 2×76 bp, 2×100 bp, 2×150 bp or 2×250 bp, where the terminology 2×N by means that the sequence read has two reads of length N base pairs from a single piece of nucleic acid (e.g., from a text nucleic acid obtained from a biological sample) that are separated by an unspecified length. In some embodiments this unspecified length is between 200 to 1200 base pairs. In some embodiments, a first sequence read in the plurality of sequence reads represents at least 25 bp, at least 30 bp, at least 50 bp, at least 100 bp, at least 200 bp, at least 250 bp, at least 500 bp, less than 500 bp, less than 400 bp, or less than 300 bp of a single piece of nucleic acid (e.g., from a text nucleic acid obtained from a biological sample).

Bin information for a plurality of bins is also obtained. Each respective bin in the plurality of bins represents a different portion of the test nucleic acid. The bin information identifies, for each respective bin in the plurality of bins, a set of sequence reads in a plurality of sets of sequence reads. Each sequence read in each set of sequence reads in the plurality of sets of sequence reads is in the plurality of sequence reads. Moreover, each respective sequence read in each respective set of sequence reads in the plurality of sets of sequence reads has a respective first portion that corresponds to a subset of the test nucleic acid that at least partially overlaps the different portion of the test nucleic acid that is represented by the bin corresponding to the respective set of sequence reads.

A determination is made as to the number of unique barcodes in a first set of sequence reads in the plurality of sequence reads, where the first set of sequence reads is of a first bin in the plurality of bins, that are also found in a second set of sequence reads in the plurality of sequence reads, where the second set of sequence reads is of a second bin in the plurality of bins. From this, a probability or likelihood that this number is attributable to chance is determined by comparison of (a) a metric based upon the determined number to (b) a threshold criterion. When the metric satisfies the threshold criterion, a structural variation is deemed to have occurred in (i) the different portion of the test nucleic acid that is represented by the first set of sequence reads and/or (ii) the different portion of the test nucleic acid that is represented by the second set of sequence reads. In some embodiments, this metric is computed as:

$$p = \Pi_i^n f_{b_i}$$

in which $\{b_1, b_2, \ldots, b_n\}$ is the set of n unique barcodes that is found in both the first and second set of sequence reads, i is an integer index to n, and $f_{b_i}$ is the fraction of the plurality of bins in which the first portion of sequence read $b_i$ appears. In some such embodiments, the metric is deemed to satisfy the threshold criterion when p is $10^{-2}$ or less, $10^{-3}$ or less, $10^{-4}$ or less, $10^{-5}$ or less, $10^{-6}$ or less, or $10^{-7}$ or less.

In some embodiments, the structural variation is an insertion or deletion of 50 consecutive bases or more, 500 consecutive bases or more, 5000 consecutive bases or more, or 10000 consecutive bases or more into the different portion of the test nucleic acid that is represented by the first set of sequence reads. In some embodiments, the structural variation is a single nucleotide polymorphism.

In some embodiments, the metric is deemed to satisfy the threshold criterion, and the method further comprises aligning each respective sequence read in the number of respective sequence reads to (i) the subset of the test nucleic acid corresponding to the first set of sequence reads and (ii) the subset of the test nucleic acid corresponding to the second set of sequence reads. A first alignment quality is determined for each respective sequence read in the number of respective sequence reads against the subset of the test nucleic acid corresponding to the first set of sequence reads based on such aligning. Then, a second alignment quality is determined for each respective sequence read in the number of respective sequence reads against the subset of the test nucleic acid corresponding to the second set of sequence reads based on the aligning. Each sequence read having a first alignment quality and a second alignment quality that are similar is eliminated from the number of respective sequence reads. With this new number of respective sequence reads, the operation of determining a probability or likelihood that the number is attributable to chance by is recomputed as a comparison of (A) the metric based upon the newly reduced number to (B) a threshold criterion. When the recomputed metric satisfies the threshold criterion, a structural variation is deemed to have occurred in (i) the different portion of the test nucleic acid that is represented by the first set of sequence reads and/or (ii) the different portion of the test nucleic acid that is represented by the second set of sequence reads.

In some embodiments, a blackout list is maintained. This blackout list comprises a plurality of blackout regions of the test nucleic acid. In such embodiments, a sequence read is eliminated from the number of respective sequence reads used to evaluate against the threshold criterion when the first portion of the sequence read overlaps a blackout region in the plurality of blackout regions.

In some embodiments, each bin in the plurality of bins represents at least 20 kbp, at least 50 kbp, at least 100 kbp, at least 250 kbp, or at least 500 kbp.

In some embodiments, the different portion of the test nucleic acid represented by the first bin overlaps the different portion of the test nucleic acid represented by the second bin. In some such embodiments, at least 50 percent, at least 80 percent, or at least 95 percent of the different portion of the test nucleic acid represented by the first bin overlaps the different portion of the test nucleic acid represented by the second bin.

In some embodiments there is no overlap between each different portion of the test nucleic acid represented by each respective bin in the plurality of bins.

In some embodiments, each respective sequence read in each respective set of sequence reads, in the plurality of sequence reads, has a respective first portion that corresponds to a subset of the test nucleic acid that fully overlaps the different portion of the test nucleic acid that is represented by the bin corresponding to the respective set of sequence reads.

In some embodiments, the plurality of bins comprises 10,000 or more bins, 100,000 or more bins, or 1,000,000 or more bins. In some embodiments the biological sample is from a multi-chromosomal species and the test nucleic acid comprises a plurality of nucleic acids collectively representing a plurality of chromosome from the multi-chromosomal species.

In some embodiments, the barcode in the second portion of each respective sequence read in the plurality of sequence reads encodes a unique predetermined value selected from the set $\{1, \ldots, 1024\}$, the set $\{1, \ldots, 4096\}$, the set $\{1, \ldots, 16384\}$, the set $\{1, \ldots, 65536\}$, the set $\{1, \ldots, 262144\}$, the set $\{1, \ldots, 1048576\}$, the set $\{1, \ldots, 4194304\}$, the set $\{1, \ldots, 16777216\}$, the set $\{1, \ldots, 67108864\}$, or the set $\{1, \ldots, 1 \times 10^{12}\}$.

In some embodiments, the barcode in the second portion of a sequence read in the plurality of sequence reads is localized to a contiguous set of oligonucleotides. In some such embodiments, the contiguous set of oligonucleotides is an N-mer, where N is an integer selected from the set $\{4, \ldots, 20\}$.

In some embodiments, the barcode in the second portion of a sequence read in the plurality of sequence reads is localized to a predetermined noncontiguous set of nucleotides within the sequence read. For instance, the noncontiguous set is localized, in various embodiments, to two noncontiguous portions, three noncontiguous portions, four noncontiguous portions, five noncontiguous portions or more of the sequence read. In some embodiments, the predetermined noncontiguous set of nucleotides collectively consists of N nucleotides, where N is an integer in the set $\{4, \ldots, 20\}$.

In some embodiments, the first sequence read corresponds to a subset of the test nucleic acid that is greater than 20 kbp, 30 kbp, 40 kbp, 50 kbp, 60 kbp, 70 kbp, or 80 kbp. In some embodiments, a first sequence read in the plurality of sequence reads is 2×36 bp, 2×50 bp, 2×76 bp, 2×100 bp, 2×150 bp or 2×250 bp, where the terminology 2×N by means that the sequence read has two reads of length N base pairs from a single piece of nucleic acid (e.g., from a text nucleic acid obtained from a biological sample) that are separated by an unspecified length. In some embodiments this unspecified length is between 200 to 1200 base pairs. In some embodiments, a first sequence read in the plurality of sequence reads represents at least 25 bp, at least 30 bp, at least 50 bp, at least 100 bp, at least 200 bp, at least 250 bp, at least 500 bp, less than 500 bp, less than 400 bp, or less than 300 bp of a single piece of nucleic acid (e.g., from a text nucleic acid obtained from a biological sample).

In some embodiments, the structural variation is a translocation of 50 consecutive bases or more into the different portion of the test nucleic acid that is represented by the first set of sequence reads from the different portion of the test nucleic acid that is represented by the second set of sequence reads.

In some embodiments, the different portion of the test nucleic acid represented by the bin corresponding to the first set of sequence reads is from a first chromosome of the biological sample, and the different portion of the test nucleic acid represented by the bin corresponding to the second set of sequence reads is from a second chromosome of the biological sample, where the second chromosome is other than the first chromosome. In some such embodiments, the first chromosome is a paternal chromosome and the second chromosome is a maternal chromosome. In some such embodiments, the biological sample is human and the first chromosome is chromosome 21, 18 or 13.

In some embodiments, the structural variation is deemed to have occurred and the method further comprises treating a subject that originated the biological sample with a treatment regimen responsive to the structural variation. In some embodiments, the treatment regimen comprises a diet modification. In some embodiments, the treatment regimen comprises application of a pharmaceutical composition that inhibits or augments a biological pathway associated with the structural variation.

Another aspect of the present disclosure is computing system comprising one or more processors and memory storing one or more programs to be executed by the one or more processors. The one or more programs comprise instructions for obtaining a plurality of sequence reads. Each respective sequence read in the plurality of sequence reads comprises a first portion that corresponds to a subset of the test nucleic acid and a second portion that encodes a barcode for the respective sequence read. The barcode is independent of the sequencing data of the test nucleic acid. Each respective bin in the plurality of bins represents a different portion of the test nucleic acid. The bin information identifies, for each respective bin in the plurality of bins, a set of sequence reads in a plurality of sets of sequence reads. Each sequence read in each set of sequence reads in the plurality of sets of sequence reads is in the plurality of sequence reads. Moreover, each respective sequence read, in each respective set of sequence reads in the plurality of sets of sequence reads, has a respective first portion that corresponds to a subset of the test nucleic acid that at least partially overlaps the different portion of the test nucleic acid that is represented by the bin corresponding to the respective set of sequence reads. A determination is made of the number of unique barcodes in a first set of sequence reads in the plurality of sequence reads, where the first set of sequence reads is of a first bin in the plurality of bins, that are also found in a second set of sequence reads in the plurality of sequence reads, where the second set of sequence reads is a second bin the plurality of bins. A probability or likelihood that this number is attributable to chance is made by comparison of a metric based upon the number to a threshold criterion. When the metric satisfies the threshold criterion, a structural variation is deemed to have occurred in (i) the different portion of the test nucleic acid that is represented by the first set of sequence reads and/or (ii) the different portion of the test nucleic acid that is represented by the second set of sequence reads.

Another aspect of the present disclosure provides a non-transitory computer readable storage medium storing one or more programs configured for execution by a computer. The one or more programs comprise instructions for obtaining a plurality of sequence reads. Each respective sequence read in the plurality of sequence reads comprises a first portion that corresponds to a subset of the test nucleic acid and a second portion that encodes an barcode for the respective sequence read. The barcode is independent of the sequencing data of the test nucleic acid. Bin information for a plurality of bins is obtained. Each respective bin in the plurality of bins represents a different portion of the test nucleic acid. The bin information identifies, for each respective bin in the plurality of bins, a set of sequence reads in a plurality of sets of sequence reads. Each sequence read in each set of sequence reads in the plurality of sets of sequence reads is in the plurality of sequence reads. Moreover, each respective sequence read, in each respective set of sequence reads in the plurality of sets of sequence reads, has a respective first portion that corresponds to a subset of the test nucleic acid that at least partially overlaps the different portion of the test nucleic acid that is represented by the bin corresponding to the respective set of sequence reads. A determination is made of the number of unique barcodes in a first set of sequence reads in the plurality of sequence reads, where the first set of sequence reads is of a first bin in the plurality of bins, that are also found in a second set of sequence reads in the plurality of sequence reads, where the second set of sequence reads is of a second bin in the plurality of bins. A probability or likelihood that this number is attributable to chance is made by comparison of a metric based upon the number to a threshold criterion. When the metric satisfies the threshold criterion, a structural variation is deemed to have occurred in (i) the different portion of the test nucleic acid that is represented by the first set of sequence reads and/or (ii) the different portion of the test nucleic acid that is represented by the second set of sequence reads.

Part B, Additional Embodiment for Structural Variation.

Another aspect of the present disclosure provide s a method of determining a likelihood of a structural variation occurring in a test nucleic acid obtained from a single biological sample. The method comprises, at a computer system having one or more processors, and memory storing one or more programs for execution by the one or more processors, obtaining a plurality of sequence reads from a plurality of sequencing reactions in which the test nucleic acid is fragmented. Each respective sequence read in the plurality of sequence reads comprises a first portion that corresponds to a subset of the test nucleic acid and a second portion that encodes a barcode for the respective sequence read. The barcode is independent of the sequencing data of the test nucleic acid.

The method further comprises obtaining bin information for a plurality of bins. Each respective bin in the plurality of bins represents a different portion of the test nucleic acid. The bin information identifies, for each respective bin in the plurality of bins, a set of sequence reads in a plurality of sets of sequence reads that are in the plurality of sequence reads. The respective first portion of each respective sequence read in each respective set of sequence reads in the plurality of sets of sequence reads corresponds to a subset of the test nucleic acid that at least partially overlaps the different portion of the test nucleic acid that is represented by the bin corresponding to the respective set of sequence reads.

The method further comprises identifying, from among the plurality of bins, a first bin and a second bin that correspond to portions of the test nucleic acid that are nonoverlapping. The first bin is represented by a first set of sequence reads in the plurality of sequence reads and the second bin is represented by a second set of sequence reads in the plurality of sequence reads.

The method further comprises determining a first value that represents a numeric probability or likelihood that the number of barcodes common to the first set and the second set is attributable to chance.

The method further comprises, responsive to a determination that the first value satisfies a predetermined cut-off value, for each barcode that is common to the first bin and the second bin, obtaining a fragment pair thereby obtaining one or more fragment pairs, each fragment pair in the one or more fragment pairs (i) corresponding to a different barcode that is common to the first bin and the second bin and (ii) consisting of a different first calculated fragment and a different second calculated fragment. For each respective fragment pair in the one or more fragment pairs: the different first calculated fragment consists of a respective first subset of sequence reads in the plurality of sequence reads having the barcode corresponding to the respective fragment pair, where each sequence read in the respective first subset of sequence reads is within a predefined genetic distance of another sequence read in the respective first subset of sequence reads, the different first calculated fragment of the respective fragment pair originates with a first sequence read having the barcode corresponding to the respective fragment pair in the first bin, and each sequence read in the respective first subset of sequence reads is from the first bin. The different second calculated fragment consists of a respective second subset of sequence reads in the plurality of sequence reads having the barcode corresponding to the respective fragment pair, where each sequence read in the respective second subset of sequence reads is within a predefined genetic distance of another sequence read in the respective second subset of sequence reads, the different second calculated fragment of the respective fragment pair originates with a second sequence read having the barcode corresponding to the respective fragment pair in the second bin, and each sequence read in the respective second subset of sequence reads is from the second bin.

The method further comprises computing a respective likelihood based upon a probability of occurrence of a first model and a probability of occurrence of a second model regarding the one or more fragment pairs to thereby provide a likelihood of a structural variation in the test nucleic acid. Here, the first model specifies that the respective first calculated fragments and the respective second calculated fragments of the one or more fragment pairs are observed given no structural variation in the target nucleic acid sequence and are part of a common molecule. Further, the second model specifies that the respective first calculated fragments and the respective second calculated fragments of the one or more fragment pairs are observed given structural variation in the target nucleic acid sequence.

In some embodiments, the computed likelihood term is a ratio score between the probability of occurrence of the first model and the probability of occurrence of the second model.

In some embodiments, the first bin and the second bin are at least a predetermined number of kilobases apart on the test nucleic acid.

In some embodiments, the first bin and the second bin are at least 50 kilobases apart on the test nucleic acid.

In some embodiments, a binomial test to compute the first value. In some embodiments, this binomial test has the form:

$$p = 1 - P_{Binom}(n; n_1 n_2 / B)$$

wherein p is the first value, expressed as a p-value, n is the number of unique barcodes that is found in both in the first and second set of sequence reads, $n_1$ is the number of unique barcodes in the first set of sequence reads, $n_2$ is the number of unique barcodes in the second set of sequence reads, and B is the total number of unique barcodes across the plurality of bins.

In some embodiments, the single biological sample is human, the test nucleic acid is the genome of the biological sample, and the first value satisfies the predetermined cut-off value when the first value is $10^{-14}$ or less. In some embodiments, the single biological sample is human, the test nucleic acid is the genome of the biological sample, and the first value satisfies the predetermined cut-off value when the first value is $10^{-15}$ or less.

In some embodiments, the structural variation is an insertion or deletion of 50 consecutive bases or more into the different portion of the test nucleic acid that is represented by the first set of sequence reads. In some embodiments, the structural variation is an insertion or deletion of 500 consecutive bases or more into the different portion of the test nucleic acid that is represented by the first set of sequence reads. In some embodiments, the structural variation is an insertion or deletion of 5000 consecutive bases or more into the different portion of the test nucleic acid that is represented by the first set of sequence reads.

In some embodiments, the structural variation is associated with a genetic disease. In some embodiments, each bin in the plurality of bins represents at least 20 kilobases of the test nucleic acid, at least 50 kilobases of the test nucleic acid, at least 100 kilobases of the test nucleic acid, at least 250 kilobases of the test nucleic acid, or at least 500 kilobases of the test nucleic acid. In some embodiments, each respective sequence read in each respective set of sequence reads in the plurality of sequence reads has a respective first portion that corresponds to a subset of the test nucleic acid that fully overlaps the different portion of the test nucleic acid that is represented by the bin corresponding to the respective set of sequence reads.

In some embodiments, the plurality of bins comprises 10,000 or more bins, 100,000 or more bins, or 1,000,000 or more bins.

In some embodiments, the biological sample is from a multi-chromosomal species and the test nucleic acid comprises a plurality of nucleic acids collectively representing a plurality of chromosomes in the multi-chromosomal species.

In some embodiments, the barcode in the second portion of each respective sequence read in the plurality of sequence reads encodes a unique predetermined value selected from the set $\{1, \ldots, 1024\}$, selected from the set $\{1, \ldots, 4096\}$, selected from the set $\{1, \ldots, 16384\}$, selected from the set $\{1, \ldots, 65536\}$, selected from the set $\{1, \ldots, 262144\}$, selected from the set $\{1, \ldots, 1048576\}$, selected from the set $\{1, \ldots, 4194304\}$, selected from the set $\{1, \ldots, 16777216\}$, selected from the set $\{1, \ldots, 67108864\}$, or selected from the set $\{1, \ldots, 1 \times 10^{12}\}$.

In some embodiments, the barcode in the second portion of a respective sequence read in the plurality of sequence reads is localized to a contiguous set of oligonucleotides within the respective sequence read.

In some embodiments, the contiguous set of oligonucleotides is an N-mer, wherein N is an integer selected from the set $\{4, \ldots, 20\}$.

In some embodiments, the barcode in the second portion of a sequence read in the plurality of sequence reads is localized to a predetermined noncontiguous set of nucleotides within the sequence read. In some embodiments, the predetermined noncontiguous set of nucleotides collectively consists of N nucleotides, wherein N is an integer in the set $\{4, \ldots, 20\}$.

In some embodiments, the first sequence read corresponds to a first subset of the test nucleic acid that is greater than 10 kilobases. In some embodiments, the first sequence read corresponds to a first subset of the test nucleic acid that is greater than 20 kilobases.

In some embodiments, the structural variation is deemed to have occurred, the method further comprising treating a subject that originated the biological sample with a treatment regimen responsive to the structural variation.

In some embodiments, the treatment regimen comprises a diet modification. In some embodiments, the treatment regimen comprises application of a pharmaceutical composition that inhibits or augments a biological pathway associated with the structural variation.

In some embodiments, an identity of the first and second bin is determined by using sparse matrix multiplication. In some embodiments, the sparse matrix multiplication has the form:

$$V = A_1^T A_2,$$

where $A_1$ is a first $B \times N_1$ matrix of barcodes that includes the first bin, $A_2$ is a second $B \times N_2$ matrix of barcodes that includes the second bin, B is the number of unique barcodes across the plurality of bins, $N_1$ is the number of bins in $A_1$, $N_2$ is the number of bins in $A_2$, and $A_1^T$ is the transpose of matrix $A_1$.

In some embodiments, the first bin is associated with a first chromosome of the biological sample, the second bin is associated with a second chromosome of the biological sample, $N_1$ is the number of bins associated with the first chromosome, and $N_2$ is the number of bins associated with the second chromosome.

In some embodiments, the first and second bin are both associated with a first chromosome of the biological sample, $N_1$ is the number of bins associated with the first chromosome, and $N_2$ equals $N_1$.

In some embodiments, a blackout list is maintained, where the blackout list comprises a plurality of blackout regions of the test nucleic acid, the method further comprising eliminating a sequence read from the plurality of sequence reads when the first portion of the sequence read overlaps a blackout region in the plurality of blackout regions.

In some embodiments, the computed likelihood in the computing is computed as:

$$LR = \frac{P(\text{observed fragments} | SV)}{P(\text{observed fragments} | \text{no } SV)}$$

where, LR is equal to a product of a plurality of terms, wherein each term in the plurality of terms (i) represents a respective fragment pair in the one or more fragment pairs and (ii) has the form:

$$\frac{P(r_1, r_2, l_1, l_2, d | SV; a_b)}{P(r_1, r_2, l_1, l_2, d | \text{no } SV; a_b)}$$

where $r_1$ is a number of sequence reads in the respective first subset of sequence reads in the first calculated fragment for the respective fragment pair, $l_1$ is a length of the first calculated fragment as determined by the first subset of sequence reads of the respective fragment pair, $r_2$ is a number of reads in the respective second subset of sequence reads in the second calculated fragment for the respective fragment pair, $l_2$ is a length of the second calculated fragment as determined by the second subset of sequence reads of the respective fragment pair, d is a distance between the first calculated fragment and the second calculated fragment of the respective fragment pair in the test nucleic acid, $a_b$ is a read rate of the first barcode across the plurality of sequence reads, SV indicates the first calculated fragment and the second calculated fragment are observed in accordance with the first model, and no SV indicates the first calculated fragment and the second calculated fragment are observed in accordance with the second model.

In some embodiments:

$$P(r_1,r_2,l_1,l_2,d|\text{no } SV;a_b)=P(r_1,r_2,l_1,l_2,d|SM, \text{no } SV;a_b)$$
$$P(SM|\text{no } SV)+P(r_1,r_2,l_1,l_2,d|DM, \text{no } SV;a_b)P$$
$$(DM|\text{no } SV),$$

where SM is the hypothesis that the first calculated molecule and the second calculated molecule originated from the same fragment of the test nucleic acid in the plurality of sequencing reactions, DM is the hypothesis that the first calculated molecule and the second calculated molecule originated from different fragments of the test nucleic acid in the plurality of sequencing reactions, $$P(r_1,r_2,l_1,l_2,d|DM, \text{no } SV;a_b)=P_{frag}(r_1,l_1;a_b)P_{frag}(r_2,l_2;a_b),$$

where $P_{frag}(r_1,l_1;a_b)$ is the probability of observing $r_1$ reads from a first molecule of unknown length such that the reads span an observed length of $l_1$, and $P_{frag}(r_2,l_2;a_b)$ is the probability of observing $r_2$ reads from a second molecule of unknown length such that the reads span an observed length of $l_2$.

In some embodiments, $P_{frag}(r_1,l_1;a_b)$ and $P_{frag}(r_2,l_2;a_b)$ are each computed as $$\sum_{m:m\geq l}\left(r(r-1)\left(\frac{l}{m}\right)^{r-2}\frac{m-l}{m^2}\right)P_p(r;ma_b)P_L(m)=$$
$$\sum_{m:m\geq l}(m-l)P_p(r-2;a_bl)P_p(0;a_b(m-l))a_b^2P_L(m)$$

where, $P_p(r;b)$ is the probability mass function of a Poisson distribution with parameter b, and $P_L(m)$ is the (pre-estimated) probability that the true molecule length of the respective molecule is m.

In some embodiments, $P(r_1,r_2,l_1,l_2,d|SM, \text{no } SV;a_b)$ is computed as $$\sum_{m:m\geq l_1+l_2+d}(m-l_1-l_2-d)P_p(r_1-$$
$$2;a_bl_1)P_p(r_2-2;a_bl_2)P_p(0;a_b(m-l_1-l_2))a_b^4P_L(m)$$

where m is the length of the true molecule length, $P_p(r_1-2;a_bl_1)$ is a probability mass function of a Poisson distribution with parameter b for $r_1$, $P_p(r_2-2;a_bl_2)$ is a probability mass function of a Poisson distribution with parameter b for $r_2$, $P_p(0;a_b(m-l_1-l_2))$ is a probability mass function of a Poisson distribution with parameter b, and $P_L(m)$ is a pre-estimated probability that the true common molecule length is m.

In some embodiments, $$P(r_1,r_2,l_1,l_2,d|SV;a_b)=P(r_1,r_2,l_1,l_2,2d'|SM, \text{no } SV;a_b)P$$
$$(SM|\text{no } SV)+P(r_1,r_2,l_1,l_2,2d'|DM, \text{no } SV;a_b)P$$
$$(DM|\text{no } SV),$$

where SM is the hypothesis that the first calculated molecule and the second calculated molecule originated from the same fragment of the test nucleic acid in the plurality of sequencing reactions, DM is the hypothesis that the first calculated molecule and the second calculated molecule originated from different fragments of the test nucleic acid in the plurality of sequencing reactions, $P(r_1,r_2,l_1,l_2,2d'|DM,SV;a_b)=P_{frag}(r_1,l_1;a_b)P_{frag}(r_2,l_2;a_b)$, where $P_{frag}(r_1,l_1;a_b)$ is the probability of observing $r_1$ reads from a first molecule of unknown length such that the reads span an observed length of $l_1$, $P_{frag}(r_2,l_2;a_b)$ is the probability of observing $r_2$ reads from a second molecule of unknown length such that the reads span an observed length of $l_2$, and 2d'=is a distance between the first calculated fragment and the second calculated fragment of the respective fragment pair in the test nucleic acid taking into account an estimate of the breakpoints of a structural variation associated with the first calculated molecule and the second calculated molecule. In some such embodiments $P_{frag}(r_1,l_1;a_b)$ and $P_{frag}(r_2,l_2;a_b)$ are each computed as $$\sum_{m:m\geq l}\left(r(r-1)\left(\frac{l}{m}\right)^{r-2}\frac{m-l}{m^2}\right)P_p(r;ma_b)P_L(m)=$$
$$\sum_{m:m\geq l}(m-l)P_p(r-2;a_bl)P_p(0;a_b(m-l))a_b^2P_L(m)$$

where, $P_p(r;b)$ is the probability mass function of a Poisson distribution with parameter b, and $P_L(m)$ is the (pre-estimated) probability that the true molecule length of the respective molecule is m. In some such embodiments $P(r_1,r_2,l_1,l_2,2d'|SM,SV;a_b)$ is computed as $$\sum_{m:m\geq l_1+l_2+d}(m-l_1-l_2-2d')P_p(r_1-$$
$$2;a_bl_1)P_p(r_2-2;a_bl_2)P_p(0;a_b(m-l_1-l_2))a_b^4P_L(m)$$

where m is the length of the true molecule length, $P_p(r_1-2;a_bl_1)$ is a probability mass function of a Poisson distribution with parameter b for $r_1$, $P_p(r_2-2;a_bl_e)$ is a probability mass function of a Poisson distribution with parameter b for $r_2$, $P_p(0;a_b(m-l_1-l_2))$ is a probability mass function of a Poisson distribution with parameter b, and $P_L(m)$ is a pre-estimated probability that the true common molecule length is m. In some such embodiments, 2d' is estimated by computing the maximum extent d' such that $P_p(0;a_bd')\geq 0.75$.

In some embodiments, the plurality of sequence reads represents whole genome sequencing data. In some embodiments, the plurality of sequence reads represents targeted sequencing of a subset of a genome, a first subset of the plurality of sequence reads sequence reads are from inside the subset of the genome and have a first read rate of $a_b$, a second subset of the plurality of sequence reads sequence reads are from outside the subset of the genome and have a first read rate of $\tilde{a}_b$, wherein $\tilde{a}_p$ is different than $a_b$, and wherein the likelihood in the computing (F) corrects for the different read rates of the respective first and second subset of the plurality of sequence reads.

Another aspect of the present disclosure provides a computing system, comprising one or more processors, memory storing one or more programs to be executed by the one or more processors. The one or more programs comprising instructions for obtaining a plurality of sequence reads from a plurality of sequencing reactions in which the test nucleic acid is fragmented. Each respective sequence read in the plurality of sequence reads comprises a first portion that corresponds to a subset of the test nucleic acid and a second portion that encodes a barcode for the respective sequence read. The barcode is independent of the sequencing data of the test nucleic acid.

The one or more programs further comprise instructions for obtaining bin information for a plurality of bins. Each respective bin in the plurality of bins represents a different portion of the test nucleic acid. The bin information identifies, for each respective bin in the plurality of bins, a set of sequence reads in a plurality of sets of sequence reads that are in the plurality of sequence reads. The respective first portion of each respective sequence read in each respective set of sequence reads in the plurality of sets of sequence reads corresponds to a subset of the test nucleic acid that at least partially overlaps the different portion of the test nucleic acid that is represented by the bin corresponding to the respective set of sequence reads. The one or more programs further comprise instructions for identifying, from among the plurality of bins, a first bin and a second bin that correspond to portions of the test nucleic acid that are nonoverlapping, where the first bin is represented by a first set of sequence reads in the plurality of sequence reads and the second bin is represented by a second set of sequence reads in the plurality of sequence reads.

The one or more programs further comprise instructions for determining a first value that represents a numeric probability or likelihood that the number of barcodes common to the first set and the second set is attributable to chance.

The one or more programs further comprise instructions for, responsive to a determination that the first value satisfies a predetermined cut-off value, for each barcode that is common to the first bin and the second bin, obtaining a fragment pair thereby obtaining one or more fragment pairs. Each fragment pair in the one or more fragment pairs (i) corresponds to a different barcode that is common to the first bin and the second bin and (ii) consists of a different first calculated fragment and a different second calculated fragment, wherein, for each respective fragment pair in the one or more fragment pairs. The different first calculated fragment consists of a respective first subset of sequence reads in the plurality of sequence reads having the barcode corresponding to the respective fragment pair. Each sequence read in the respective first subset of sequence reads is within a predefined genetic distance of another sequence read in the respective first subset of sequence reads. The different first calculated fragment of the respective fragment pair originates with a first sequence read having the barcode corresponding to the respective fragment pair in the first bin. Each sequence read in the respective first subset of sequence reads is from the first bin. The different second calculated fragment consists of a respective second subset of sequence reads in the plurality of sequence reads having the barcode corresponding to the respective fragment pair. Each sequence read in the respective second subset of sequence reads is within a predefined genetic distance of another sequence read in the respective second subset of sequence reads. The different second calculated fragment of the respective fragment pair originates with a second sequence read having the barcode corresponding to the respective fragment pair in the second bin. Each sequence read in the respective second subset of sequence reads is from the second bin. The one or more programs comprising instructions for computing a respective likelihood based upon a probability of occurrence of a first model and a probability of occurrence of a second model regarding the one or more fragment pairs to thereby provide a likelihood of a structural variation in the test nucleic acid. Here, the first model specifies that the respective first calculated fragments and the respective second calculated fragments of the one or more fragment pairs are observed given no structural variation in the target nucleic acid sequence and are part of a common molecule. Further, the second model specifies that the respective first calculated fragments and the respective second calculated fragments of the one or more fragment pairs are observed given structural variation in the target nucleic acid sequence.

Part C, Phasing Methods.

Another aspect of the present disclosure provides methods for phasing sequencing data of a test nucleic acid sample. In some embodiments the test nucleic acid sample is obtained from a single biological sample from a single organism of a species. In some embodiments the test nucleic acid sample is obtained from a single biological sample but may represent more than a single species. Such a situation arises, for example, when a host has been infected by, for instance, a retrovirus.

The test nucleic acid sample comprises a first set of haplotypes ($H_O$) and a second set of haplotypes ($H_1$). In other words, the biological sample is diploid and inherits maternal and paternal haplotypes. For instance, some portions of the genome of the biological sample are paternally inherited while other portions of the genome are maternally inherited. If the portions that are maternally inherited were to arbitrarily be designated the haplotype $H_O$, the portions that are paternally inherited are designated $H_1$.

In typical embodiments, the method occurs at a computer system having one or more processors, and memory storing one or more programs for execution by the one or more processors of the methods. In the disclosed methods, a reference consensus sequence for all or a portion of a genome of the species is obtained. In some embodiments, the reference consensus sequence is partial or incomplete. In some embodiments, the reference consensus sequence is the sequence of only a single organism of the species. In some embodiments, the reference consensus sequence is the consensus sequence of a plurality of organisms of the species.

In the method, a plurality of variant calls $A_{i,p}$ is obtained. Here, i is an index to a position in the reference consensus sequence. In some embodiments, $p \in \{0, 1\}$ in which label "0" assigns a respective variant call in $A_{i,p}$ to $H_O$ and label "1" assigns the respective variant call to $H_1$, and n is the number of variants calls in $A_{i,p}$. For example, if n is 5, there are five positions i in $A_{i,p}$ and each such position is independently labeled as either 0 (indicating a first haplotype) or 1 (indicating a second haplotype).

In some alternative embodiments, $p \in \{0, 1, -1\}$ in which label "0" assigns a respective variant call in $A_{i,p}$ to $H_O$, label "1" assigns the respective variant call to $H_1$, and label "−1" provides the advantageous possibility of denoting an error condition in the assignment of the variant call to a haplotype. This alternative embodiment takes into consideration that standard variant calling algorithms that are relied upon to provide calls at positions $A_{i,p}$ between $H_O$ and $H_1$ may, in fact, call such positions incorrectly on occasion. For instance, consider the case in which there are twenty sequence reads from the same sequenced nucleic acid fragment f, each with the same barcode 132, for a position i of fragment f and further suppose that conventional variant calling algorithms call position i heterozygous with seventeen of the sequence reads called $H_0$ at position i and the remaining three called $H_1$ at position i. Further suppose that ground truth for position i from fragment f is, in fact homozygous $H_0$ meaning that the standard variant calling algorithms should have called position i $H_0$ for all twenty sequence reads. As such, the conventional haplotype assignment has miscalled three of the sequence reads. The disclosed alternative phasing embodiment p∈{0, 1, −1} advantageously accounts for the possibility of this form of error. In the example of the twenty sequence reads above where three of the twenty sequence reads are miscalled at position i, this position i in all twenty of the sequence reads is assigned −1 ($H_{-1}$), the error state, when such error at position i is being sampled (to see if it provides a better phasing solution) by the disclosed phasing algorithms. The ability to selectively sample for this error state advantageously protects the phasing algorithm from error in the input data that arises, for instance due to error in the sequencing process, weak sequencing signal, and the like.

In the methods, a plurality of barcoded sequence reads $\vec{O}$ is obtained. In some embodiments, each respective sequence read $\vec{O}_q$ in the plurality of sequence reads, where q is an integer index into $\vec{O}$, comprises a first portion that corresponds to a subset of the reference sequence and a second portion that encodes a respective barcode, independent of the reference sequence, for the respective sequence read, in a plurality of barcodes.

In some embodiments, each respective sequence read $\vec{O}_q$ in the plurality of sequence reads $\vec{O}$ is ∈{0, 1, −}$^n$, where (i) each respective label "0" for the respective sequence read $\vec{O}_q$ assigns a corresponding variant call in $A_{i,p}$ to $H_0$, (ii) each respective label "1" for the respective sequence read $\vec{O}_q$ assigns a corresponding variant call in $A_{i,p}$ to $H_1$, and (iii) each respective label "−" for the respective sequence read $\vec{O}_q$ indicates that the corresponding variant call in $A_{i,p}$ is not covered. For example, consider the case in which $\vec{O}_q$ contains 5 of the 10 variant calls in $A_{i,p}$. In this example, $\vec{O}_q$ will contain five variant calls with values "−" because they are not in the respective sequence read and $\vec{O}_q$ will contain values for the five other variant calls in $A_{i,p}$. Each value in these five values will be a zero or a one depending on the haplotype assigned to the respective variant call in the sequence read. In some embodiments, such haplotype assignments are obtained for the variant calls in individual sequence reads using conventional haplotype assignment algorithms.

In some embodiments, to account for possible error in the zygosity of a variant call as described above, each respective sequence read $\vec{O}_q$ in the plurality of sequence reads $\vec{O}$ is ∈{0, 1, −1, −}$^n$, where (i) each respective label "0" for the respective sequence read $\vec{O}_q$ assigns a corresponding variant call in $A_{i,p}$ to $H_0$, (ii) each respective label "1" for the respective sequence read $\vec{O}_q$ assigns a corresponding variant call in $A_{i,p}$ to $H_1$, (iii) each respective label "−1" for the respective sequence read $\vec{O}_q$ assigns a corresponding variant call in $A_{i,p}$ to the zygosity error condition (present, but neither $H_0$ nor $H_1$), and (iv) each respective label "−" for the respective sequence read $\vec{O}_q$ indicates that the corresponding variant call in $A_{i,p}$ is not covered.

In the disclosed methods, a phasing result $\vec{X}$ is obtained by optimization of haplotype assignments at individual positions i in $A_{i,p}$. In embodiments where each respective sequence read $\vec{O}_q$ in the plurality of sequence reads $\vec{O}$ is ∈{0, 1, −}$^n$, these haplotype assignments are each between $H_0$ and $H_1$ at individual positions i for the plurality of sequence reads. In the alternative embodiments where possible error in the zygosity of the position i is to be additionally sampled in the phasing algorithm, each respective sequence read $\vec{O}_q$ in the plurality of sequence reads $\vec{O}$ is ∈{0, 1, −1, −}$^n$, these haplotype assignments are each between $H_0$, $H_1$ and $H_{-1}$ at individual positions i for the plurality of sequence reads, where $H_{-1}$ denotes the zygosity error condition above.

Sequence reads are aligned to a reference genome. Furthermore, sequence reads that have the same barcode are grouped together. In this way, sequence reads with a common barcode are partitioned into groups that are likely to have originated from a single genomic input fragment f, and thus provide evidence that the alleles covered by the sequence read came from the same haplotype.

In embodiments where each respective sequence read $\vec{O}_q$ in the plurality of sequence reads $\vec{O}$ is ∈{0, 1, −}$^n$, the probability of the observed sequence reads covering variant i from fragment f is computed as:

$$\log P(O_{i,f} \mid A_{i,p}) = \sum_r 1(S_r = A_{i,p})(1 - 10^{-Q_r/10}) + 1(S_r \neq A_{i,p})(10^{-Q_r/10})$$

where,
r sums over all sequence reads for fragment f,
$1(S_r = A_{i,p})$ is the indicator function that has the value "1" when the $r^{th}$ sequence read $S_r$ from fragment f matches $A_{i,p}$ and is "0" otherwise,
$1(S_r \neq A_{i,p})$ is the indicator function that has the value "1" when the $r^{th}$ sequence read $S_r$ from fragment f does not matches $A_{i,p}$ and is "0" otherwise, and
$Q_r$ is a relevant quality value associated with the $r^{th}$ sequence read.

In embodiments where each respective sequence read $\vec{O}_q$ in the plurality of sequence reads $\vec{O}$ is ∈{0, 1, −1, −}$^n$, that is possible zygosity error at position i is additionally sampled, the probability of the observed sequence reads covering variant i from fragment f is computed as:

$$\log P(O_{i,f} \mid A_{i,p}) = \sum_r 1(S_r = A_{i,p})(1 - 10^{-Q_r/10}) + 1(S_r \neq A_{i,p})(10^{-Q_r/10}) + 1(A_{i,p} = X^-)^{0.5}$$

where,
$X^-$ is $H_{-1}$, and
$1(A_{i,p} = X^-)$ is the indicator function that has the value "1" when $A_{i,p}$ is equal to −1 ($H_{-1}$) and is "0" otherwise.

In embodiments where $\vec{O}$ is ∈{0, 1, −}$^n$, the phasing result can be obtained by optimizing an objective function expressed as a maximum likelihood phasing parity vector:

$$\hat{X} = \overset{\text{argmax}}{\vec{X}} P(\vec{O} \mid \vec{X})$$

Here, $\hat{X}$ is the refined phasing vector while $\vec{X}$ is the phasing vector result to be inferred and $$P(\vec{O} \mid \vec{X}) = \Pi_f P(O_{1,f}, \ldots, O_{N,f}).$$

In embodiments where $\vec{O}$ is $\in \{0, 1, -1, -\}^n$, the phasing vector can be found by optimizing an overall objective function:

$$\overset{\text{argmax}}{\vec{X}} P(\vec{X} \mid \vec{O}) \bigg| = \frac{P(\vec{X})P(\vec{O} \mid \vec{X})}{C} \text{ where,}$$

$$P(\vec{X}) = \prod_i \frac{(1-\varepsilon_i)}{2}(X_i = H_1) + (X_i = H_0) + \varepsilon_i(X_i = H_{-1}),$$

$H_{-1}$ is the condition of zygosity error at position i,
$\varepsilon_i$ is an estimate of incurring this form of error at position i, and $$P(\vec{O} \mid \vec{X}) = \prod_f P(O_{1,f}, \ldots, O_{N,f}).$$

In some embodiments, $\varepsilon_i$ is a function of the type of variant at position i. For instance $\varepsilon_i$ is given a first value if the variant at position i arises through genetic insertions or deletion, and another value if the variant at position i arises by other means (e.g., single nucleotide polymorphisms).

Each $O_{i,f}$ in $(O_{1,f}, \ldots, O_{N,f})$ is the respective subset of barcoded sequence reads for fragment f (e.g., contain the same barcode sequence). Moreover, $$P(O_{1,f}, \ldots, O_{N,f} \mid X, H_f=0) = \Pi_i P(O_{i,f} \mid A_{i,X_i}),$$

$$P(O_{1,f}, \ldots, O_{N,f} \mid X, H_f=1) = \Pi_i P(O_{i,f} \mid A_{i,1-X_i}), \text{ and}$$

$$P(O_{1,f}, \ldots, O_{N,f} \mid X, H_f=M) = \Pi_i 0.5.$$

Here, M indicates a mixture of $H_f=0$ and $H_f=1$ for fragment f. In other words, $H_f=0$ represents fragment f mapping to $H_0$ and $H_f=1$ represents fragment f mapping to $H_1$. The above three equations provide for the three possibilities for the sequence reads having a common barcode: either the sequence reads are haplotype 0 (from the first haplotype set), haplotype 1 (from the second haplotype set), or they are M, which arises in the rare instance where both maternal and paternal genomic material for the region of the reference sequence covered by the partition associated with sequence barcode f is present in the partition giving rise to a sequence read $O_{q,f}$.

In some embodiments, ten or more sequence reads have the same barcode, twenty or more sequence reads have the same barcode, thirty or more sequence reads have the same barcode, one hundred or more sequence reads have the same barcode, or one thousand or more sequence reads have the same barcode.

In some embodiments, the three possible haplotype assignments for each $O_{q,f}$ in $(O_{1,f}, \ldots, O_{N,f})$ are scored as:

$$P(O_{1,f}, \ldots, O_{N,f} \mid X) =$$

$$\frac{(1-\alpha)}{2}\left(\prod_i P(O_{i,f} \mid A_i, X_i) + \prod_i P(O_{i,f} \mid A_i, 1-X_i)\right) + \alpha \prod_i 0.5.$$

Here, $\alpha$ is a predetermined fractional value representing a likelihood or probability that $H_f=M$ arises (prior probability that $H_f=M$), and log $P(O_{i,f} \mid A_{i,p})$ is defined as above for either the embodiment where $\vec{O}$ is $\in \{0, 1, -\}^n$ or the embodiment where $\vec{O}$ is $\in \{0, 1, -1, -\}^n$.

In some embodiments, the set of variant calls comprises a plurality of heterozygous single nucleotide polymorphisms, heterozygous inserts, or heterozygous deletions in the test nucleic acid.

In some embodiments, the first set of haplotypes (H=0) consists of maternal haplotypes for the single organism, and the second set of haplotypes (H=1) consists of paternal haplotypes for the single organism.

In some embodiments, the plurality of barcodes comprises 1000 or more barcodes, 10,000 or more barcodes, 100,000 or more barcodes, or 1×10⁶ or more barcodes. In some embodiments, the species is human.

In some embodiments, the plurality of variant calls $A_{i,p}$ comprises 1000 or more variant calls, or 10,000 or more variant calls. In some embodiments, the plurality of sequence reads comprises 10,000 or more sequence reads, 100,000 or more sequence reads, or 1×10⁶ or more sequence reads.

In some embodiments X is (x) where x is a binary string of length n, each value of "0" in x indicates origination of the corresponding variant call in the first set of haplotypes (H=0), and each value of "1" in x indicates origination of the corresponding variant call in the second set of haplotypes H=1).

In some embodiments, the first set of haplotypes (H=0) consists of a single maternal haplotype and the second set of haplotypes (H=1) consists of a single paternal haplotype. In some embodiments, the first set of haplotypes (H=0) comprises five or more maternal haplotypes corresponding to five or more maternal chromosomes and the second set of haplotypes (H=1) comprises five or more paternal haplotypes corresponding to five or more paternal chromosomes.

In some embodiments, the subset of sequence reads that originate from the same fragment f (and include the same respective sequence barcode) comprises 10 or more sequence reads, 30 or more sequence reads, or 100 or more sequence reads.

In some embodiments, a subset of sequence reads that include the same respective sequence read represent a fragment f of the reference consensus sequence that is at least 30 kilobases in length, at least 40 kilobases in length, or between 20 kilobases and 60 kilobases length. In some such embodiments, each such sequence read in the subset of sequence reads is 2×36 bp, 2×50 bp, 2×76 bp, 2×100 bp, 2×150 bp or 2×250 bp, where the terminology 2×N by means that the sequence read has two reads of length N base pairs from the reference consensus sequence that are separated by an unspecified length. In some embodiments this unspecified length is between 200 to 1200 base pairs. In some embodiments, each sequence read in the subset of sequence reads represents at least 25 bp, at least 30 bp, at least 50 bp, at least 100 bp, at least 200 bp, at least 250 bp, at least 500 bp, less than 500 bp, less than 400 bp, or less than 300 bp of the reference consensus sequence.

In some embodiments, one of the overall objective function is optimized. In some embodiments the overall objective function is optimized. In some embodiments, the hierarchical search comprises, for each respective local block of variant calls in $A_{i,p}$ that are localized to a corresponding subset of the reference consensus sequence, using a beam search over the assignments of $X_k, X_{k+1}, \ldots, X_{k+j}$ in the respective local block of variant calls, where k is the first variant in the respective local block of variant calls, j is a number of variant calls in the respective local block of variant calls and where assignments of $X_k, X_{k+1}, \ldots, X_{k+j}$ are found by computing one of the objective functions described above in which the phasing vector of the objective function in respective computations of the objective function for assignments $X_k, X_{k+1}, \ldots, X_{k+j}$ is limited to $X_k, X_{k+1}, \ldots, X_{k+j}$, thereby finding an optimal phasing solution for each respective local block of variant calls. Further, in some embodiments, neighboring local blocks of variant calls in $A_{i,p}$ are greedily joined using the optimal phasing solution for each respective local block of variant calls thereby obtaining an estimate of the optimal phasing configuration $\hat{X}$. In some embodiments, neighboring local blocks of variant calls in $A_{i,p}$ are joined using Monte Carlo algorithms, or other stochastic searches such as simulated annealing or Boltzmann learning, etc. using the optimal phasing solution for each respective local block of variant calls. See for example Duda et al., 2001, *Pattern Classification*, Second Edition, John Wiley & Sons, Inc., New York, which is hereby incorporated by reference herein for such purpose of disclosing, for instance, stochastic search methods.

In some embodiments, refining the phase result further comprises iteratively swapping the phase result of individual $x_i$ in the estimate of the optimal phasing configuration) $\hat{X}$ and recomputing the objective function, thereby obtaining $\hat{X}$.

In some embodiments, a respective local block of variant calls consists of between 20 and 60 variants in $A_{i,p}$. In some embodiments, a respective local block of variant calls consists of between 30 and 80 variants in $A_{i,p}$. In some embodiments, an iteration of the beam search for the assignments of one of $X_k, X_{k+1}, \ldots, X_{k+j}$ discards all but a predetermined number of solutions for $\hat{X}$. In some embodiments, the predetermined number of solutions for $\hat{X}$ is 1000 or less. In some embodiments, predetermined number of solutions for $\hat{X}$ is 5000 or less.

In some embodiments, the species is human and the test nucleic acid sample comprises the genome of the biological sample. In some embodiments, the species is a multi-chromosomal species and the test nucleic acid sample comprises a plurality of nucleic acids collectively representing a plurality of chromosomes in the multi-chromosomal species.

In some embodiments, the barcode in the second portion of each respective sequence read in the plurality of sequence reads O encodes a unique predetermined value selected from the set $\{1, \ldots, 1024\}$, selected from the set $\{1, \ldots, 4096\}$, selected from the set $\{1, \ldots, 16384\}$, selected from the set $\{1, \ldots, 65536\}$, selected from the set $\{1, \ldots, 262144\}$, selected from the set $\{1, \ldots, 1048576\}$, selected from the set $\{1, \ldots, 4194304\}$, selected from the set $\{1, \ldots, 16777216\}$, selected from the set $\{1, \ldots, 67108864\}$, or selected from the set $\{1, \ldots, 1\times 10^{12}\}$. In some embodiments, the barcode in the second portion of a respective sequence read in the plurality of sequence reads is localized to a contiguous set of oligonucleotides within the respective sequence read. In some embodiments, the contiguous set of oligonucleotides is an N-mer, where N is an integer selected from the set $\{4, \ldots, 20\}$. In some embodiments, the barcode in the second portion of a sequence read in the plurality of sequence reads is localized to a predetermined noncontiguous set of nucleotides within the sequence read. In some embodiments, the predetermined noncontiguous set of nucleotides collectively consists of N nucleotides, wherein N is an integer in the set $\{4, \ldots, 20\}$.

In some embodiments, the subset of sequence reads in the plurality of sequence reads having the same barcode corresponds to a portion of the reference consensus sequence that is greater than 10 kilobases. In some embodiments, the subset of sequence reads having the same barcode corresponds to a portion of the reference consensus sequence that is greater than 20 kilobases.

Another aspect of the present disclosure provides a computing system, comprising one or more processors and memory storing one or more programs to be executed by the one or more processors. The one or more programs comprise instructions for phasing sequencing data of a test nucleic acid sample obtained from a biological sample from a single organism of a species. The test nucleic acid sample comprises a first set of haplotypes (H=0) and a second set of haplotypes (H=1). The one or more programs execute the phasing methods disclosed in the present disclosure.

Another aspect of the present disclosure provides a method of phasing sequencing data of a test nucleic acid sample obtained from a biological sample from a single organism of a species. The test nucleic acid sample comprises a first set of haplotypes (H=0) and a second set of haplotypes (H=1). The method comprises, at a computer system having one or more processors, and memory storing one or more programs for execution by the one or more processors, obtaining a plurality of variant calls $A_{i,p}$, where i is an index to a position in a reference consensus sequence for all or a portion of a genome of the species, and $p \in \{0, 1\}$ in which label 0 assigns a respective variant call in $A_{i,p}$ to H=0 and label 1 assigns the respective variant call to H=1. For each respective local block of variant calls in $A_{i,p}$ that are localized to a corresponding subset of the reference consensus sequence, a beam search or equivalent search technique is used over the haplotype assignments of local phasing vectors $X_k, X_{k+1}, \ldots, X_{k+j}$ in the respective local block of variant calls, where k is the first variant in the respective local block of variant calls, j is a number of variant calls in the respective local block of variant calls, assignments of $X_k, X_{k+1}, \ldots, X_{k+j}$ are found by computing an objective function in which the phasing vector of the objective function in respective computations is limited to $X_k, X_{k+1}, \ldots, X_{k+j}$, and the objective function is calculated by matching observed sequence reads of the test nucleic acid sample against the respective local block of variant calls in $A_{i,p}$, thereby finding a phasing solution for each respective local block of variant calls in $A_{i,p}$. Upon completion of the beam search for each respective local block of variant calls in $A_{i,p}$, neighboring local blocks of variant calls in $A_{i,p}$ are greedily joined using the phasing solution for each respective local block of variant calls thereby obtaining a phasing configuration $\hat{X}$ for the single organism of the species. In some embodiments, the method further comprises iteratively swapping the phase result of individual $x_i$ in $\hat{X}$ and recomputing the objective function, thereby obtaining $\hat{X}$. In some embodiments, a respective local block of variant calls consists of between 20 and 60 variants in $A_{i,p}$. In some embodiments, a respective local block of variant calls consists of between 30 and 80 variants in $A_{i,p}$. In some embodiments, an iteration of the beam search for the assignments of one of $X_k, X_{k+1}, \ldots, X_{k+j}$ discards all but a predetermined number of solutions for $\hat{X}$ (e.g., 1000 or less, 5000 or less, etc.)

Another aspect of the present disclosure provides a method of addressing error in the zygosity of variant calls in phasing sequencing data of a test nucleic acid sample obtained from a biological sample from a single organism of a species. The test nucleic acid sample comprises a first set of haplotypes ($H_0$) and a second set of haplotypes ($H_1$). The method comprises, at a computer system having one or more processors, and memory storing one or more programs for execution by the one or more processors, obtaining a reference consensus sequence for all or a portion of a genome of the species and obtaining a plurality of variant calls $A_{i,p}$ for the biological sample. Here, i is an index to a position in the reference consensus sequence and $p \in \{0, 1, -1\}$ in which label 0 assigns a respective variant call in $A_{i,p}$ to $H_O$, label 1 assigns the respective variant call to $H_1$, and label $-1$ assigns the respective variant call to the zygosity error condition $H_{-1}$. In the method, a plurality of sequence reads $\vec{O}$ for the biological sample is obtained. Each respective sequence read $\vec{O}_i$ in the plurality of sequence reads comprises a first portion that corresponds to a subset of the reference sequence and a second portion that encodes a respective barcode, independent of the reference sequence, for the respective sequence read, in a plurality of barcodes. Each respective sequence read $\vec{O}i$ in the plurality of sequence reads is $\in \{0, 1, -1, -\}^n$. Here, (i) n is the number of variants calls in $A_{i,p}$, (ii) each respective label 0 for the respective sequence read $\vec{O}i$ assigns a corresponding variant call in $A_{i,p}$ to $H_O$, (iii) each respective label 1 for the respective sequence read $\vec{O}i$ assigns a corresponding variant call in $A_{i,p}$ to $H_O$, (iv) each respective label $-1$ for the respective sequence read $\vec{O}i$ assigns a corresponding variant call in $A_{i,p}$ to $H_{-1}$, and (v) each respective label for the respective sequence read $\vec{O}i$ indicates that the corresponding variant call in $A_{i,p}$ is not covered. In the method, a phasing vector result $\hat{X}$ is refined by optimization of haplotype assignments at individual positions i in $A_{i,p}$ between $H_O$, $H_1$ and $H_{-1}$ for the plurality of sequence reads using an overall objective function:

$$\hat{X} = \genfrac{}{}{0pt}{}{\text{argmax}}{\vec{X}} \left. P(\vec{X} \mid \vec{O}) \right) = \frac{P(\vec{X})P(\vec{O} \mid \vec{X})}{C} \text{ where}$$

$$P(\vec{X}) = \prod_i \frac{(1-\varepsilon_i)}{2}(X_i = H_1) + (X_i = H_0) + \varepsilon_i(X_i = H_{-1}),$$

$\varepsilon_i$ is an estimate of incurring $H_{-1}$ at position i, and $P(\vec{O}|\vec{X}) = \Pi_f P(O_{1,f}, \ldots, O_{N,f})$, $\hat{X}$ is the refined phasing vector result,
C is a constant,
$\vec{X}$ is the phasing vector result to be inferred, and
$(O_{1,f}, \ldots, O_{N,f})$ is the respective subset of N variant calls in the plurality of variant calls $A_{i,p}$ observed in the subset of sequence reads that include the same respective barcode from the plurality of barcodes.

In some embodiments, $(O_{1,f}, \ldots, O_{N,f}|\vec{X}, H_f=0) = \Pi_i P(O_{i,f}|A_{i,X_i})$, $P(O_{1,f}, \ldots, O_{N,f}|\vec{X}, H_f=1) = \Pi_i P(O_{i,f}|A_{i,1-X_i})$, $P(O_{1,f}, \ldots, O_{N,f}|\vec{X}, H_f=M) = \Pi_i 0.5$, M indicates a mixture of $H_f=0$ and $H_f=1$ for the respective barcode f, $$P(O_{1,f}, \ldots, O_{N,f} \mid \vec{X}) = \frac{(1-\alpha)}{2}\left(\prod_i P(O_{i,f} \mid A_i, X_i) + \prod_i P(O_{i,f} \mid A_i, 1-X_i)\right) + \alpha \prod_i 0.5,$$

$\log P(O_{i,f}|A_{i,p}) = \Sigma_r 1(S_r = A_{i,p})(1 - 10^{-Q_r/10}) + 1(S_r \ne A_{i,p})$
$(10^{-Q_r/10}) + 1(A_{i,p} = H_{-1})0.5$ $\alpha$ is a predetermined fractional value representing a likelihood or probability that $H_f = M$ arises, i is the $i^{th}$ variant in the respective subset of N variant calls observed for the subset of sequence reads that include the same respective barcode, r sums over the subset of sequence reads that include the same respective barcode, $1(S_r = A_{i,p})$ is an indicator function testing if the base assignment at position i in the $r^{th}$ sequence read $S_r$ in the subset of sequence reads that include the same respective barcode matches Ai,p, wherein when they match $1(S_r = A_{i,p})$ has a value of 1 and when they do not match $1(S_r = A_{i,p})$ has a value of zero, $1(S_r \ne A_{i,p})$ is an indicator function testing if the base assignment at position i in the $r^{th}$ sequence read $S_r$ in the subset of sequence reads that include the same respective barcode does not match Ai,p, wherein when they do not match $1(S_r \ne A_{i,p})$ has a value of 1 and when they do match $1(S_r = A_{i,p})$ has a value of zero, $1(A_{i,p} = H_{-1})$ is an indicator function that has a value of 1 when $A_{i,p}$ is equal to $H_{-1}$ and is a value of zero otherwise, and $Q_r$ is a quality value for $S_r$ for the read base at the position of i in the reference consensus sequence.

In some embodiments, the plurality of variant calls comprises a plurality of heterozygous single nucleotide polymorphisms, heterozygous inserts, or heterozygous deletions in the test nucleic acid. In some embodiments, the first set of haplotypes ($H_0$) consists of maternal haplotypes for the single organism, and the second set of haplotypes ($H_1$) consists of paternal haplotypes for the single organism.

In some embodiments, the plurality of barcodes comprises 1000 or more barcodes. In some embodiments, the plurality of barcodes comprises 10,000 or more barcodes. In some embodiments, the plurality of barcodes comprises 100,000 or more barcodes. In some embodiments, the plurality of barcodes comprises $1 \times 10^6$ or more barcodes. In some embodiments, the species is human. In some embodiments, the plurality of variant calls $A_{i,p}$ comprises 1000 or more variant calls or 10,000 or more variant calls. In some embodiments, the plurality of sequence reads comprises 10,000 or more sequence reads, 100,000 or more sequence reads, or $1 \times 10^6$ or more sequence reads.

In some embodiments, $\vec{X}$ is (x), where x is a binary string of length n, each value of 0 in x indicates origination of the corresponding variant call in the first set of haplotypes ($H_0$), and each value of 1 in x indicates origination of the corresponding variant call in the second set of haplotypes ($H_1$).

In some embodiments, the first set of haplotypes ($H_0$) consists of a single maternal haplotype and the second set of haplotypes ($H_1$) consists of a single paternal haplotype.

In some embodiments, the first set of haplotypes ($H_0$) comprises five or more maternal haplotypes corresponding to five or more maternal chromosomes and the second set of haplotypes ($H_1$) comprises five or more paternal haplotypes corresponding to five or more paternal chromosomes.

In some embodiments, the subset of sequence reads that include the same respective barcode f comprises 10 or more sequence reads. In some embodiments, the subset of sequence reads that include the same respective barcode f comprises 30 or more sequence reads. In some embodiments, the subset of sequence reads that include the same respective barcode f comprises 100 or more sequence reads. In some embodiments, a subset of sequence reads that include the same respective barcode f represent at least 30 kilobases of the reference consensus sequence or at least 40 kilobases of the reference consensus sequence.

In some embodiments, the refining optimizes the overall objective function using a hierarchical search over $\vec{X}$. In some embodiments, the hierarchical search comprises, for each respective local block of variant calls in $A_{i,p}$ that are localized to a corresponding subset of the reference consensus sequence, using a beam search over the assignments of $X_k, X_{k+1}, \ldots, X_{k+j}$ in the respective local block of variant calls, where k is the first variant in the respective local block of variant calls, j is a number of variant calls in the respective local block of variant calls and wherein assignments of $X_k, X_{k+1}, \ldots, X_{k+j}$ are found by computing the objective function in which the phasing vector of the objective function in respective computations is limited to $X_k, X_{k+1}, \ldots, X_{k+j}$, thereby finding an optimal phasing solution for each respective local block of variant calls, and greedily joining neighboring local blocks of variant calls in $A_{i,p}$ using the optimal phasing solution for each respective local block of variant calls thereby obtaining an estimate of the optimal phasing configuration $\hat{X}$. In some embodiments, the refining the phase result further comprises iteratively swapping the phase result of individual $x_i$ in the estimate of the optimal phasing configuration $\hat{X}$ and recomputing the objective function, thereby obtaining $\hat{X}$.

In some embodiments, a respective local block of variant calls consists of between 20 and 60 variants in $A_{i,p}$. In some embodiments, a respective local block of variant calls consists of between 30 and 80 variants in $A_{i,p}$. In some embodiments, an iteration of the beam search for the assignments of one of $X_k, X_{k+1}, \ldots, X_{k+j}$ discards all but a predetermined number of solutions for $\hat{X}$. In some embodiments, the predetermined number of solutions for $\hat{X}$ is 1000 or less. In some embodiments, the predetermined number of solutions for $\hat{X}$ is 5000 or less.

In some embodiments, the species is human and the test nucleic acid sample comprises the genome of the biological sample. In some embodiments, the species is a multi-chromosomal species and the test nucleic acid sample comprises a plurality of nucleic acids collectively representing a plurality of chromosomes in the multi-chromosomal species.

In some embodiments, barcode in the second portion of each respective sequence read in the plurality of sequence reads O encodes a unique predetermined value selected from the set $\{1, \ldots, 1024\}$, selected from the set $\{1, \ldots, 4096\}$, selected from the set $\{1, \ldots, 16384\}$, selected from the set $\{1, \ldots, 65536\}$, selected from the set $\{1, \ldots, 262144\}$, selected from the set $\{1, \ldots, 1048576\}$, selected from the set $\{1, \ldots, 4194304\}$, selected from the set $\{1, \ldots, 16777216\}$, selected from the set $\{1, \ldots, 67108864\}$, or selected from the set $\{1, \ldots, 1\times 10^{12}\}$.

In some embodiments, the barcode in the second portion of a respective sequence read in the plurality of sequence reads is localized to a contiguous set of oligonucleotides within the respective sequence read. In some embodiments, the contiguous set of oligonucleotides is an N-mer, wherein N is an integer selected from the set $\{4, \ldots, 20\}$.

In some embodiments, the barcode in the second portion of a sequence read in the plurality of sequence reads is localized to a predetermined noncontiguous set of nucleotides within the sequence read. In some embodiments, the predetermined noncontiguous set of nucleotides collectively consists of N nucleotides, wherein N is an integer in the set $\{4, \ldots, 20\}$.

In some embodiments, a sequence read in the plurality of sequence reads corresponds to a portion of the reference consensus sequence that is greater than 10 kilobases or greater than 20 kilobases.

In some embodiments, the plurality of variant calls is obtained from the plurality of sequence reads. In some embodiments, the plurality of sequence reads is obtained from a plurality of barcoded-oligo coated gel-beads and wherein the test nucleic acid sample is 50 ng or less. In some embodiments, the plurality of barcoded-oligo coated gel-beads comprises 10,000 beads. In some embodiments, the plurality of barcoded-oligo coated gel-beads comprises 50,000 beads. In some embodiments, is 25 ng or less, 10 ng or less, 5 ng or less, or 2.5 ng or less.

In some embodiments, the plurality of sequencing reads $\vec{O}$ is obtained within ten minutes of exposure to the plurality of barcodes. In some embodiments, the plurality of sequencing reads $\vec{O}$ is obtained within twenty minutes of exposure to the plurality of barcodes.

The present disclosure further provides a non-transitory computer readable storage medium storing one or more programs configured for execution by a computer, the one or more programs comprising instructions for carrying out any of the disclosed methods. Thus, these methods, systems, and non-transitory computer readable storage medium provide improved methods for detecting a structural variant in sequencing data of a test nucleic acid obtained from a biological sample.

Thus, these methods, systems, and non-transitory computer readable storage medium provide improved methods for detecting structural variants in sequencing data of a test nucleic acid obtained from a biological sample and for phasing such data.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the drawings. In the figures that include method flowcharts, boxes that are dashed indicate example embodiments.

FIGS. 7A, 7B, 7C, 7D, 7E, 7F, 7G, and 7H illustrate a method of detecting a structural variant in sequencing data of a test nucleic acid obtained from a biological sample in accordance with some implementations.

FIG. 10 provides metrics on two separate sequencing runs (from two different sources of target nucleic acid) using the systems and methods of the present disclosure.

FIG. 12 illustrates a phasing objective function in accordance with an embodiment of the systems and methods of the present disclosure in which $O_{q,f}$ are the observations of variant i, from molecule f, $A_{i,p}$ is the allele on phase p at variant i, $X_i$ is the phasing of variant i, $Sr=A_{i,p}$ means that sequence read r matches allele $A_{i,p}$, and $\alpha$ is the allele collision probability.

FIG. 14 illustrates phase metrics for the phasing in accordance with an embodiment of the systems and methods of the present disclosure in which an example of the phasing of the present disclosure (column "NA12878 WES") is compared with conventional phasing (columns NA12878 WGS, HuRef 1 WGS, and NA20847 WGS).

FIG. 16 illustrates called deletions in NA12878 using an embodiment of the systems and methods of the present disclosure.

FIG. 19 provides sequencing metrics for various samples run using the disclosed systems and methods.

FIG. 20 illustrates detection of annotated gene fusions using the systems and methods of the present disclosure.

FIG. 24 illustrates haplotype phasing of gene fusion events in accordance with some embodiments of the present disclosure.

FIG. 30 summarizes structural variant statistics for 0.2 fmol of intronic bait versus no intronic bait runs described in FIGS. 27 through 29.

DETAILED DESCRIPTION

The present disclosure generally provides methods, processes, and particularly computer implemented processes and non-transitory computer program products for use in the analysis of genetic sequence data, and in particular, for detecting structural variations (e.g., deletions, duplications, copy-number variants, insertions, inversions, translocations, long term repeats (LTRs), short term repeats (STRs), and a variety of other useful characterizations), as well as for haplotype phasing, in sequencing data of a test nucleic acid obtained from a biological sample. Details of implementations are now described in relation to the Figures.

Figure 1:
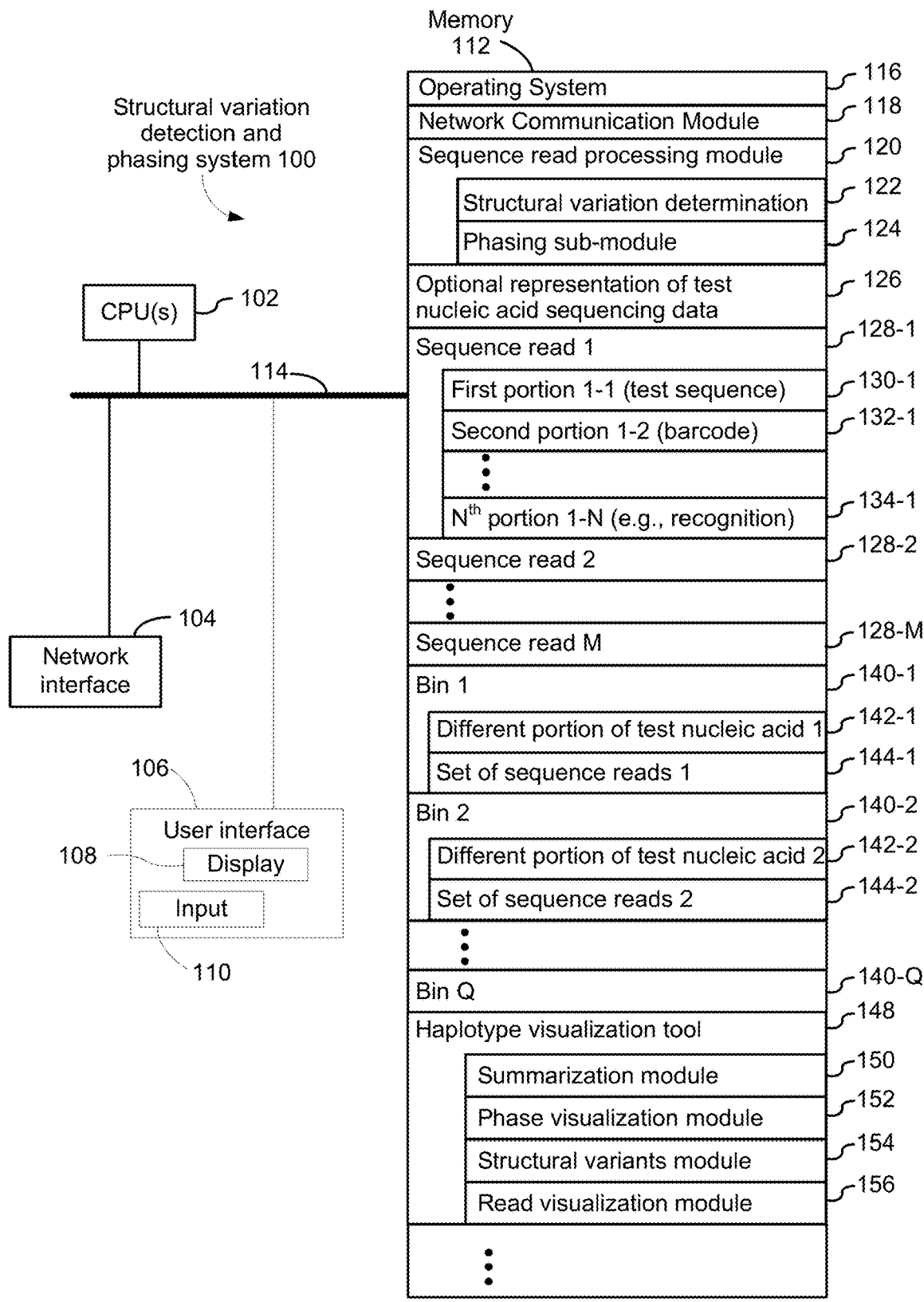
FIG. 1 is an example block diagram illustrating a computing device in accordance with some implementations.
Figure 2A:
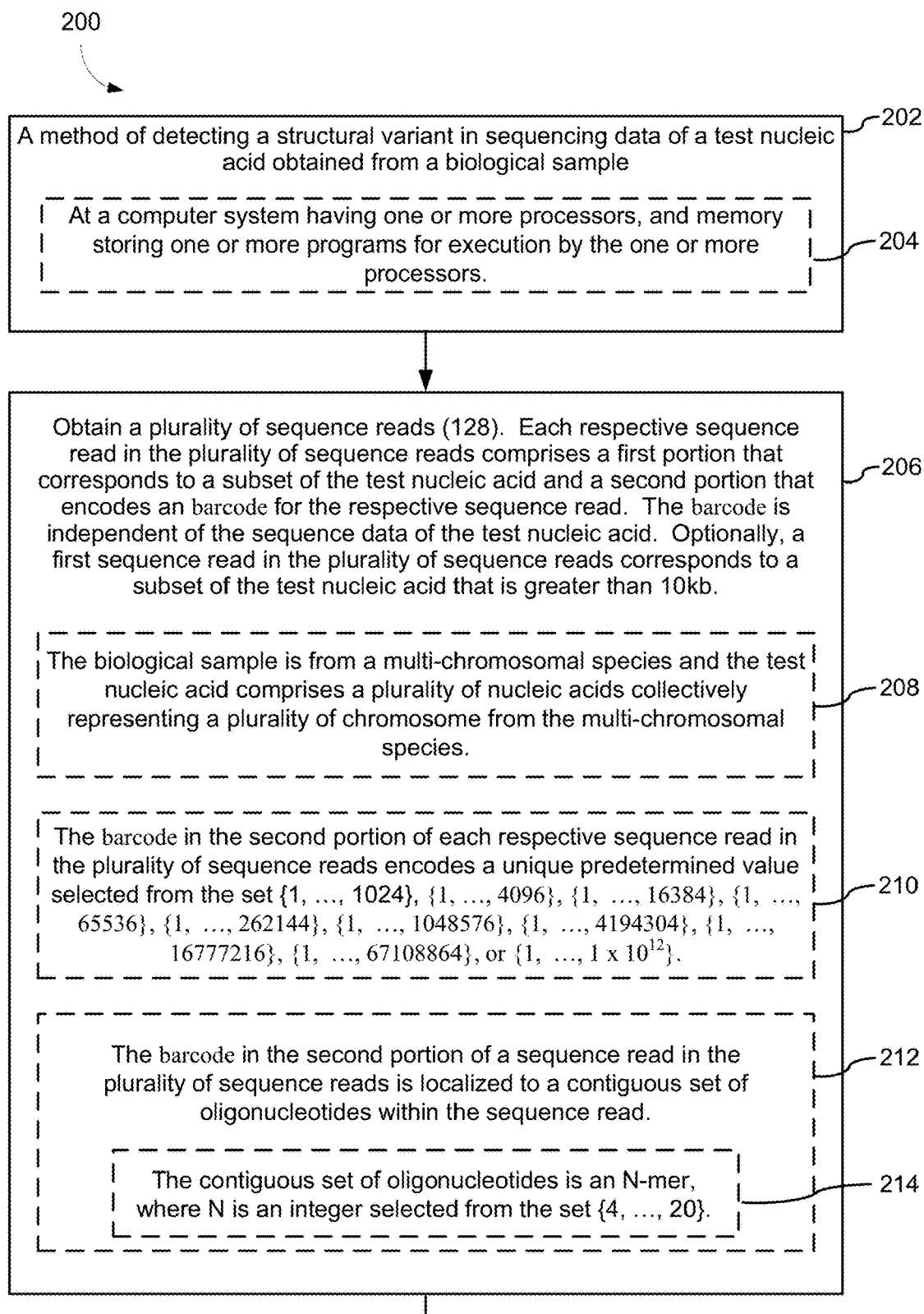
FIGS. 2A, 2B, 2C, 2D, and 2E illustrate a method of detecting a structural variant in sequencing data of a test nucleic acid obtained from a biological sample in accordance with some implementations.
Figure 2B:
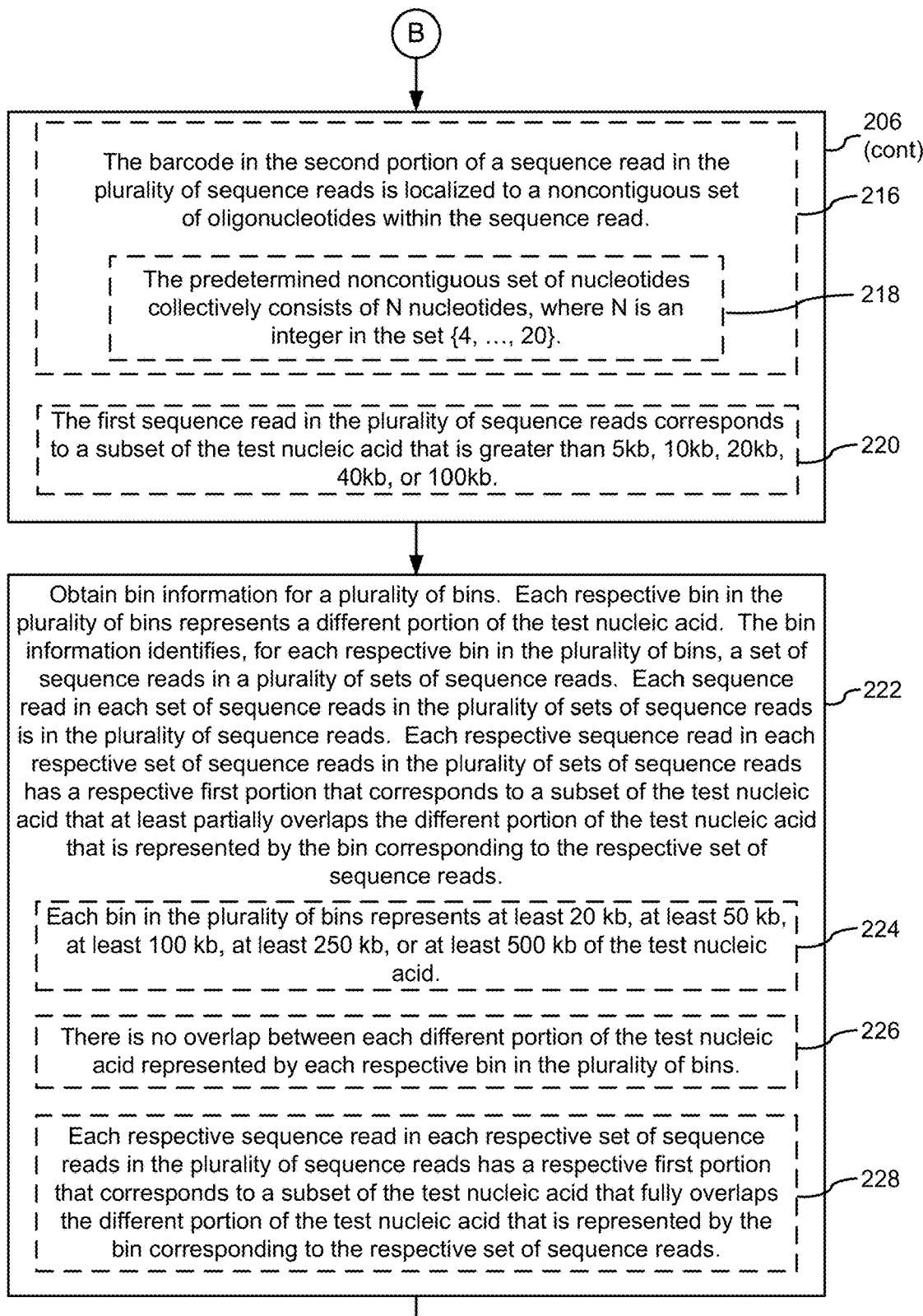
Figure 2C:
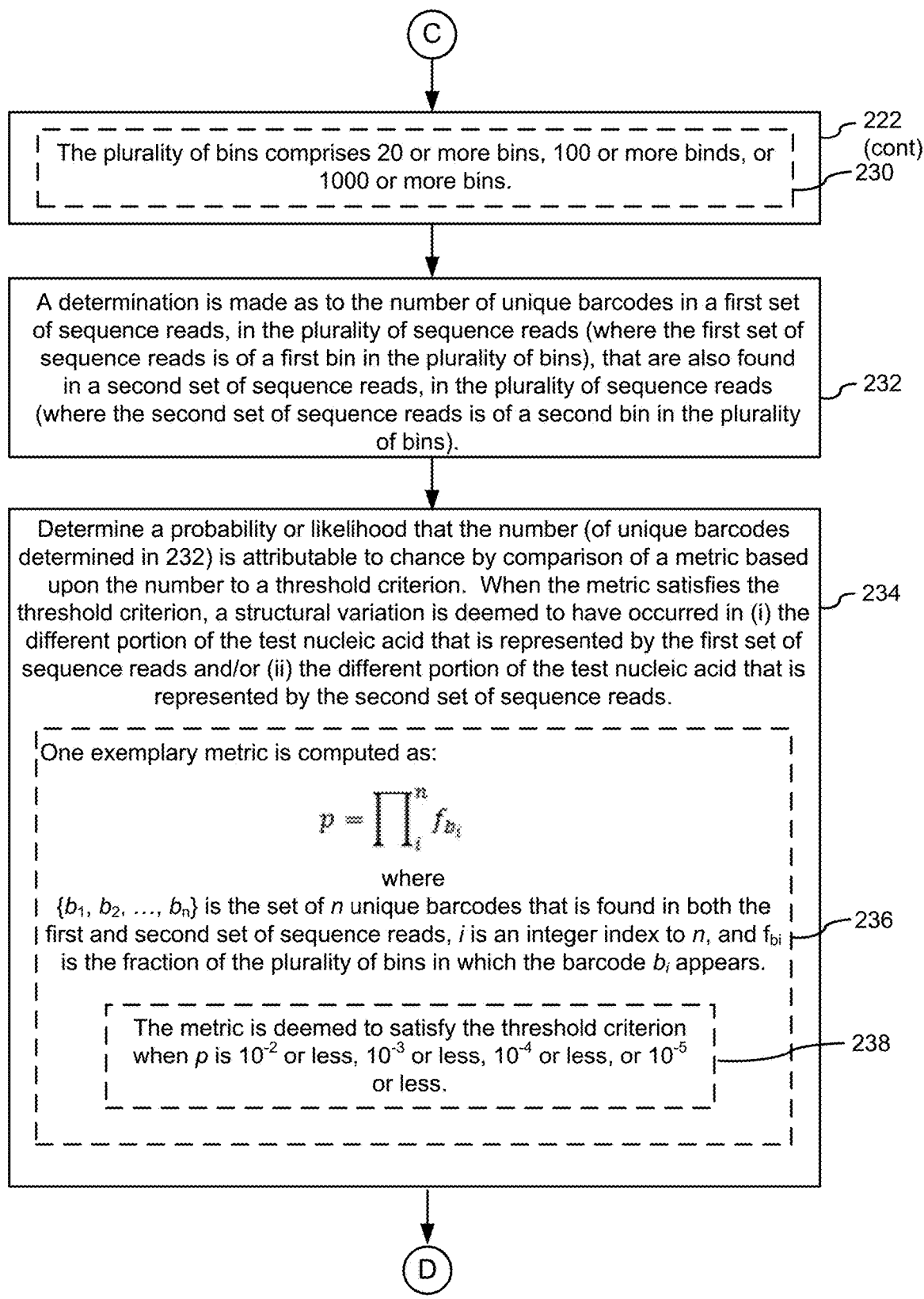
Figure 2D:
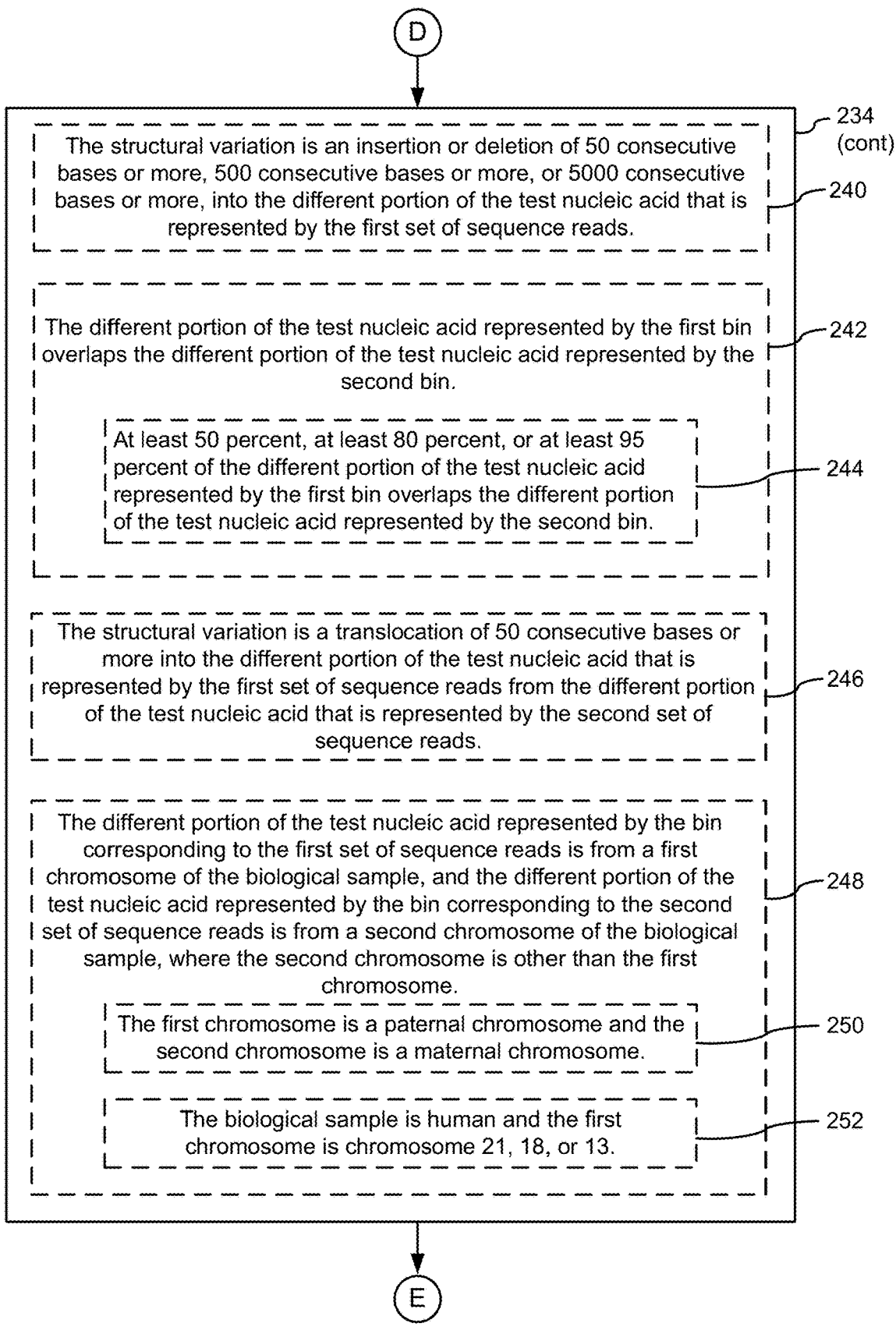
Figure 2E:
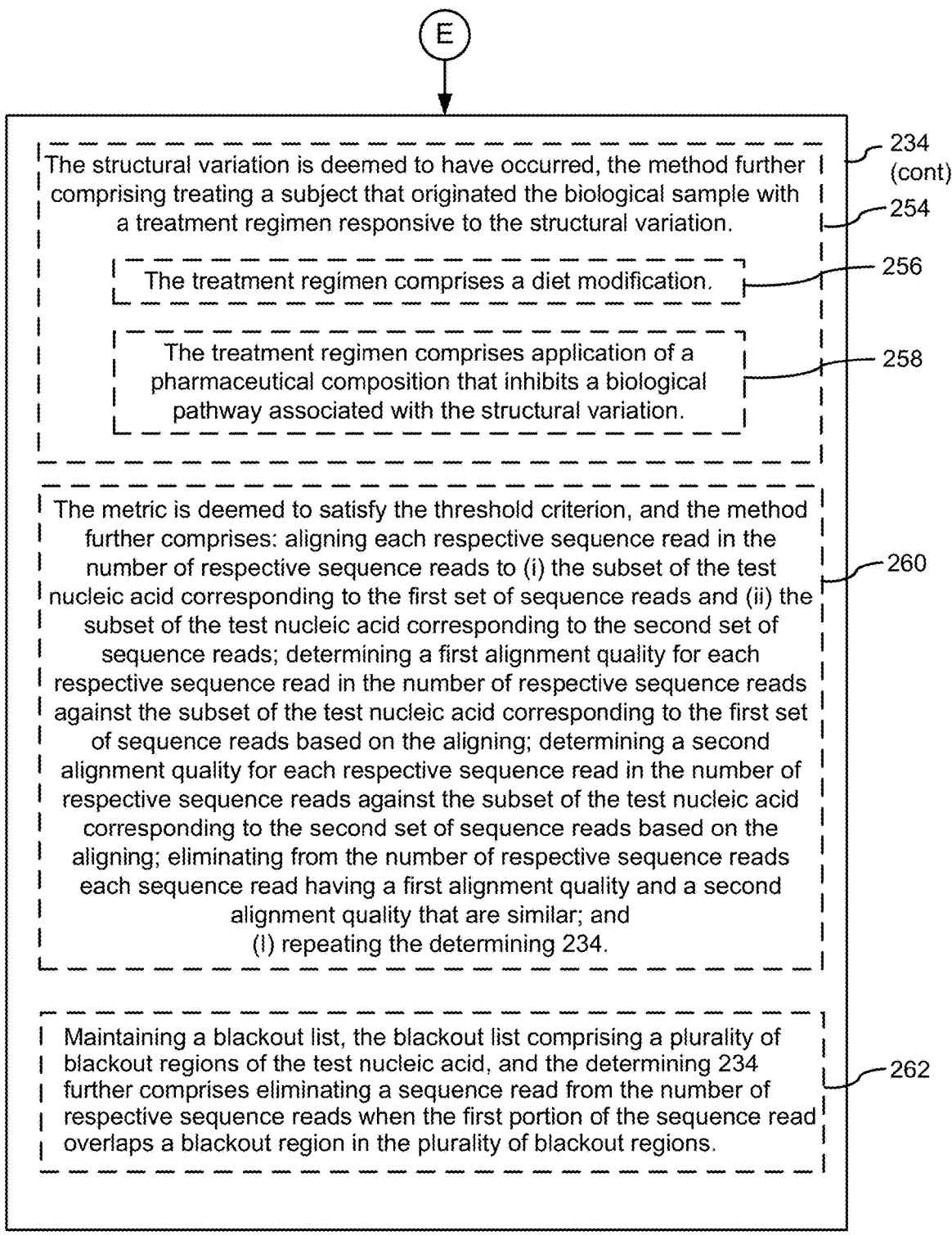

FIG. 1 is a block diagram illustrating a structural variant detection and phasing system 100 in accordance with some implementations. The device 100 in some implementations includes one or more processing units CPU(s) 102 (also referred to as processors), one or more network interfaces 104, a user interface 106, a memory 112, and one or more communication buses 114 for interconnecting these components. The communication buses 114 optionally include circuitry (sometimes called a chipset) that interconnects and controls communications between system components. The memory 112 typically includes high-speed random access memory, such as DRAM, SRAM, DDR RAM, ROM, EEPROM, flash memory, CD-ROM, digital versatile disks (DVD) or other optical storage, magnetic cassettes, magnetic tape, magnetic disk storage or other magnetic storage devices, other random access solid state memory devices, or any other medium which can be used to store desired information; and optionally includes non-volatile memory, such as one or more magnetic disk storage devices, optical disk storage devices, flash memory devices, or other non-volatile solid state storage devices. The memory 112 optionally includes one or more storage devices remotely located from the CPU(s) 102. The memory 112, or alternatively the non-volatile memory device(s) within the memory 112, comprises a non-transitory computer readable storage medium. In some implementations, the memory 112 or alternatively the non-transitory computer readable storage medium stores the following programs, modules and data structures, or a subset thereof:

- an optional operating system 116, which includes procedures for handling various basic system services and for performing hardware dependent tasks;
- an optional network communication module (or instructions) 118 for connecting the device 100 with other devices, or a communication network;
- an optional sequence read processing module 120 for processing sequence reads, including a structural variation determination sub-module 122 for identifying structural variations in a genetic sample from a single organism of a species and a phasing sub-module 124 for identifying the haplotype of each sequence read of the genetic sample;
- one or more nucleic acid sequencing datasets 126, each such dataset obtained using a genetic sample from a single organism of a species;
- a plurality of sequence reads 128, each respective sequence read in the plurality of sequence reads comprising at least a first portion 130 that corresponds to a subset of the test nucleic acid 602 and a second portion 132 that encodes a barcode for the respective sequence read;
- a plurality of bins, each respective bin 140 in the plurality of bins representing a different portion 142 of the test nucleic acid 602 and further associated with a set of sequence reads 144 of the test nucleic acid; and
- a haplotype visualization tool 148 for to visualizing structural variation and phasing information in nucleic acid sequencing data, including a summarization module 150, a phase visualization module 152, a structural variants (visualization) module 154, and a read visualization module 156.

In some implementations, the user interface 106 includes an input device (e.g., a keyboard, a mouse, a touchpad, a track pad, and/or a touch screen) 100 for a user to interact with the system 100 and a display 108.

In some implementations, one or more of the above identified elements are stored in one or more of the previously mentioned memory devices, and correspond to a set of instructions for performing a function described above. The above identified modules or programs (e.g., sets of instructions) need not be implemented as separate software programs, procedures or modules, and thus various subsets of these modules may be combined or otherwise re-arranged in various implementations. In some implementations, the memory 112 optionally stores a subset of the modules and data structures identified above. Furthermore, in some embodiments, the memory stores additional modules and data structures not described above. In some embodiments, one or more of the above identified elements is stored in a computer system, other than that of system 100, that is addressable by system 100 so that system 100 may retrieve all or a portion of such data when needed.

Although FIG. 1 shows a "structural variation detection and phasing system 100," the figure is intended more as functional description of the various features which may be present in computer systems than as a structural schematic of the implementations described herein. In practice, and as recognized by those of ordinary skill in the art, items shown separately could be combined and some items could be separated.

Part A, Structural Variation.

FIG. 2 is a flow chart illustrating a method of determining a structural variation occurring in a test nucleic acid obtained from a single biological sample (202). In some embodiments, the method takes place at a computer system having one or more processors, and memory storing one or more programs for execution by the one or more processors in accordance with some embodiments (204).

Obtaining a Plurality of Sequence Reads.

In accordance with the disclosed systems and methods, a plurality of sequence reads 128 is obtained (206) using a test nucleic acid 602. Such sequence reads ultimately form the basis of a nucleic acid sequencing dataset 126. Each respective sequence read 128 in the plurality of sequence reads comprises a first portion 130 that corresponds to a subset of the test nucleic acid and a second portion 132 that encodes an barcode for the respective sequence read. The barcode is independent of the sequencing data of the test nucleic acid. In other words, the barcode is not derived from, or a function of the sequencing data of the test nucleic acid. In some instances a sequence read is referred to herein as a next generation sequencing (NGS) read-pair.

In some embodiments, a first sequence read in the plurality of sequence reads corresponds to a subset of the test nucleic acid that is is 2×36 bp, 2×50 bp, 2×76 bp, 2×100 bp, 2×150 bp or 2×250 bp, where the terminology 2×N by means that the sequence read has two reads of length N base pairs from a single piece of nucleic acid (e.g., from a text nucleic acid obtained from a biological sample) that are separated by an unspecified length. In some embodiments this unspecified length is between 200 to 1200 base pairs. In some embodiments, a first sequence read in the plurality of sequence reads represents at least 25 bp, at least 30 bp, at least 50 bp, at least 100 bp, at least 200 bp, at least 250 bp, at least 500 bp, less than 500 bp, less than 400 bp, or less than 300 bp of a single piece of nucleic acid (e.g., from a text nucleic acid obtained from a biological sample). More generally, sequence read 128 obtained in some embodiments, are assembled into contigs with an N50 of at least about 10 kbp, at least about 20 kbp, or at least about 50 kbp. In more preferred aspects, sequence reads are assembled into contigs of at least about 100 kbp, at least about 150 kbp, at least about 200 kbp, and in many cases, at least about 250 kbp, at least about 300 kbp, at least about 350 kbp, at least about 400 kbp, and in some cases, or at least about 500 kbp or more. In still other embodiments, sequence reads are phased into contigs with an N50 in excess of 200 kbp, in excess of 300 kbp, in excess of 400 kbp, in excess of 500 kbp, in excess of 1 Mb, or even in excess of 2 Mb are obtained in accordance with the present disclosure. See Miller et al., 2010, "Assembly algorithms for next generation sequencing data," Genomics 95, pp. 315-327, which is hereby incorporated by reference for a definition on N50 and conventional contig assembly algorithms.

Figure 6:
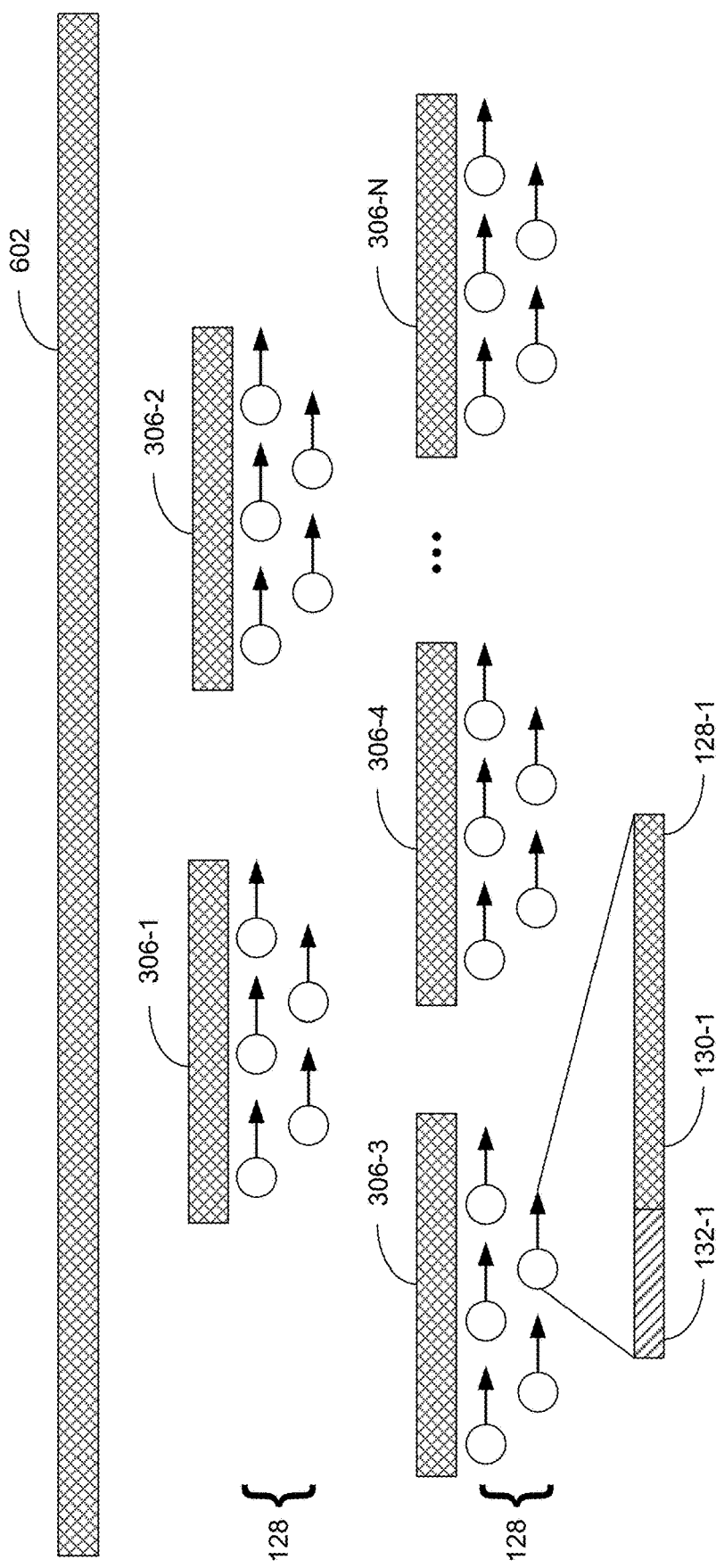
FIG. 6 illustrates the relationship between the test nucleic acid (e.g., chromosomal DNA), the different fragments of the larger test nucleic acid, and sequence reads of fragments in accordance with some embodiments.

In some embodiments, as illustrated in FIG. 6, to obtain the plurality of sequence reads 128, a larger contiguous nucleic acid 602 (the test nucleic acid, e.g., chromosomal DNA) is fragmented to form fragments 306 and these fragments are compartmentalized, or partitioned into discrete compartments or partitions (referred to interchangeably herein as partitions). In some embodiments, the test nucleic acid 602 is the genome of a multi-chromosomal organism such as a human. In some embodiments, more than 10, more than 100, more than 1000, more than 10,000, more than 100,000, more than $1 \times 10^6$, or more than $5 \times 10^6$ sets of sequence reads are obtained, corresponding more than 10, more than 100, more than 1000, more than 10,000, more than 100,000, more than $1 \times 10^6$, or more than $5 \times 10^6$ partitions. FIG. 6 thus illustrates the relationship between the larger contiguous nucleic acid 602, the different fragments 306 of the larger contiguous nucleic acid, and sequence reads 128 of fragments. Typically, between 1 and 250 fragments 604, between 5 and 500 fragments 604 or between 10 and 1000 fragments 604 are each partitioned into a separate partition. In any event, sufficiently few of the fragments 804 are partitioned into the same partition such that the chance that the fragments 804 in a single partition have any appreciable overlapping sequences is unlikely. Sequence reads 728 of each fragment 804 are made. In typical embodiments, sequence reads 128 are short in length (e.g., less than 1000 bases) so that they can be sequenced in automated sequencers. Each sequence read 128 in a partition includes a common second portion 132 that forms a barcode that is independent of the sequence of the larger contiguous nucleic 602 acid nucleic acid and that identifies the partition, in a plurality of partitions, in which the respective sequence read was formed.

In some embodiments, the test nucleic acid is the genome of a multi-chromosomal organism such as a human. In some embodiments, the biological sample is from a multi-chromosomal species and the test nucleic acid comprises a plurality of nucleic acids collectively representing a plurality of chromosomes from the multi-chromosomal species (208).

Each partition maintains separation of its own contents from the contents of other partitions. As used herein, the partitions refer to containers or vessels that may include a variety of different forms, e.g., wells, tubes, micro or nanowells, through holes, or the like. In preferred aspects, however, the partitions are flowable within fluid streams. In some embodiments, these vessels are comprised of, e.g., microcapsules or micro-vesicles that have an outer barrier surrounding an inner fluid center or core, or have a porous matrix that is capable of entraining and/or retaining materials within its matrix. In a preferred aspect, however, these partitions comprise droplets of aqueous fluid within a non-aqueous continuous phase, e.g., an oil phase. A variety of different suitable vessels are described in, for example, U.S. patent application Ser. No. 13/966,150, filed Aug. 13, 2013, which is hereby incorporated by reference herein in its entirety. Likewise, emulsion systems for creating stable droplets in non-aqueous or oil continuous phases are described in detail in, e.g., Published U.S. Patent Application No. 2010-0105112, which is hereby incorporated by reference herein in its entirety. In certain embodiments, microfluidic channel networks are particularly suited for generating partitions. Examples of such microfluidic devices include those described in detail in Provisional U.S. Patent Application No. 61/977,804, filed Apr. 4, 2014, the full disclosure of which is incorporated herein by reference in its entirety for all purposes. Alternative mechanisms may also be employed in the partitioning of individual cells, including porous membranes through which aqueous mixtures of cells are extruded into non-aqueous fluids. Such systems are generally available from, e.g., Nanomi, Inc.

In the case of droplets in an emulsion, partitioning of the test nucleic acid fragments into discrete partitions may generally be accomplished by flowing an aqueous, sample containing stream, into a junction into which is also flowing a non-aqueous stream of partitioning fluid, e.g., a fluorinated oil, such that aqueous droplets are created within the flowing stream partitioning fluid, where such droplets include the sample materials. As described below, the partitions, e.g., droplets, also typically include co-partitioned barcode oligonucleotides.

The relative amount of sample materials within any particular partition may be adjusted by controlling a variety of different parameters of the system, including, for example, the concentration of test nucleic acid fragments in the aqueous stream, the flow rate of the aqueous stream and/or the non-aqueous stream, and the like. The partitions described herein are often characterized by having overall volumes that are less than 1000 pL, less than 900 pL, less than 800 pL, less than 700 pL, less than 600 pL, less than 500 pL, less than 400 pL, less than 300 pL, less than 200 pL, less than 100 pL, less than 50 pL, less than 20 pL, less than 10 pL, or even less than 1 pL. Where co-partitioned with beads, it will be appreciated that the sample fluid volume within the partitions may be less than 90% of the above described volumes, less than 80%, less than 70%, less than 60%, less than 50%, less than 40%, less than 30%, less than 20%, or even less than 10% of the above described volumes. In some cases, the use of low reaction volume partitions is particularly advantageous in performing reactions with small amounts of starting reagents, e.g., input test nucleic acid fragments. Methods and systems for analyzing samples with low input nucleic acids are presented in U.S. Provisional Patent Application No. 62/017,580, filed Jun. 26, 2014, the full disclosure of which is hereby incorporated by reference in its entirety.

Once the test nucleic acid fragments 306 are introduced into their respective partitions, the test nucleic acid fragments 306 within partitions are generally provided with unique barcodes such that, upon characterization of those test nucleic acid fragments 306, they may be attributed as having been derived from their respective partitions. In some embodiments, such unique barcodes are previously, subsequently or concurrently delivered to the partitions that hold the compartmentalized or partitioned test nucleic acid fragments, in order to allow for the later attribution of the characteristics, e.g., nucleic acid sequence information, to the sample nucleic acids included within a particular compartment, and particularly to relatively long stretches of contiguous sample nucleic acids that may be originally deposited into the partitions.

Accordingly, the fragments 604 are typically co-partitioned with the unique barcodes (e.g., barcode sequences). In particularly preferred aspects, the unique barcodes are provided in the form of oligonucleotides that comprise nucleic acid barcode sequences that is attached to test nucleic acid fragments in the partitions. The oligonucleotides are partitioned such that as between oligonucleotides in a given partition, the nucleic acid barcode sequences contained therein are the same, but as between different partitions, the oligonucleotides can, and preferably have differing barcode sequences. In preferred embodiments, only one nucleic acid barcode sequence is associated with a given partition, although in some embodiments, two or more different barcode sequences are present in a given partition.

The nucleic acid barcode sequences will typically include from 6 to about 20 or more nucleotides within the sequence of the oligonucleotides. In some embodiments, these nucleotides are completely contiguous, i.e., in a single stretch of adjacent nucleotides. In alternative embodiments, they are separated into two or more separate subsequences that are separated by one or more nucleotides. Typically, separated subsequences are separated by about 4 to about 16 intervening nucleotides.

The test nucleic acid 602 is typically partitioned such that the nucleic acids are present in the partitions in relatively long fragments or stretches of contiguous nucleic acid molecules 306 of the original test nucleic acid 602. As illustrated in FIG. 6, these fragments 306 typically represent a number of overlapping fragments of the overall test nucleic acid to be analyzed, e.g., an entire chromosome, exome, or other large genomic fragment. In some embodiments, the test nucleic acid 602 includes whole genomes, individual chromosomes, exomes, amplicons, or any of a variety of different nucleic acids of interest. Typically, the fragments 306 of the test nucleic acid 602 that are partitioned are longer than 1 kbp, longer than 5 kbp, longer than 10 kbp, longer than 15 kbp, longer than 20 kbp, longer than 30 kbp, longer than 40 kbp, longer than 50 kbp, longer than 60 kbp, longer than 70 kbp, longer than 80 kbp, longer than 90 kbp or even longer than 100 kbp.

The test nucleic acid 602 is also typically partitioned at a level whereby a given partition has a very low probability of including two overlapping fragments 306 of the starting test nucleic acid 602. This is typically accomplished by providing the test nucleic acid 602 at a low input amount and/or concentration during the partitioning process. As a result, in preferred cases, a given partition includes a number of long, but non-overlapping fragments 306 of the starting test nucleic acid 602. The nucleic acid fragments 306 in the different partitions are then associated with unique barcodes where, for any given partition, nucleic acids contained therein possess the same unique barcode, but where different partitions include different unique barcodes. Moreover, because the partitioning step allocates the sample components into very small volume partitions or droplets, it will be appreciated that in order to achieve the desired allocation as set forth above, one need not conduct substantial dilution of the sample, as would be required in higher volume processes, e.g., in tubes, or wells of a multiwell plate. Further, because the systems described herein employ such high levels of barcode diversity, one can allocate diverse barcodes among higher numbers of genomic equivalents, as provided above. In some embodiments, in excess of 10,000, 100,000, 500,000, etc. diverse barcode types are used to achieve genome:(barcode type) ratios that are on the order of 1:50 or less, 1:100 or less, 1:1000 or less, or even smaller ratios, while also allowing for loading higher numbers of genomes (e.g., on the order of greater than 100 genomes per assay, greater than 500 genomes per assay, 1000 genomes per assay, or even more) while still providing for far improved barcode diversity per genome. Here, each such genome is an example of a test nucleic acid.

Figure 3A:
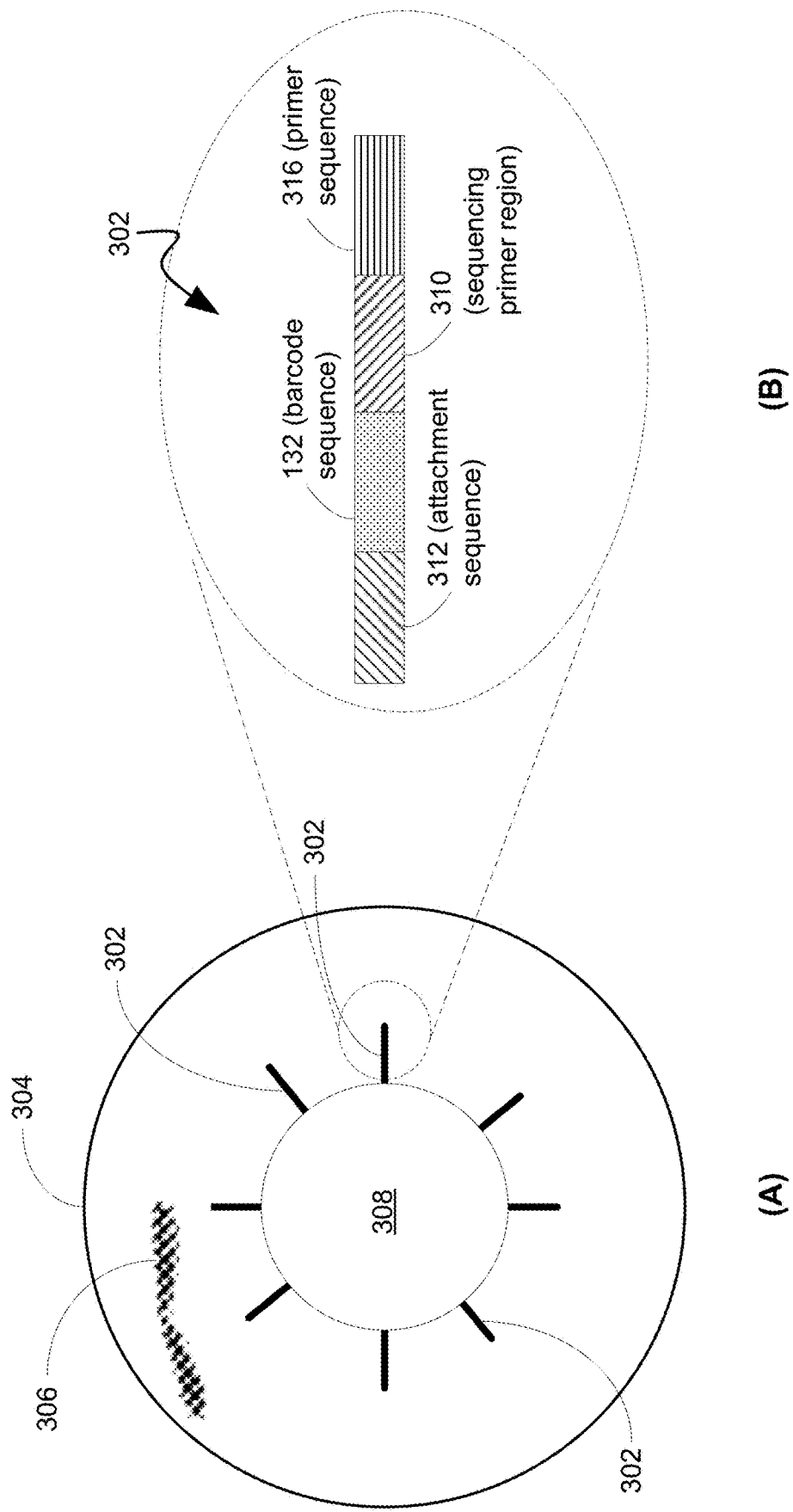
FIGS. 3A, 3B, 3C, 3D, 3E, 3F,3G and 3H illustrate exemplary constructs in accordance with some embodiments.

Referring to FIG. 3A, panel B, often the above-described partitioning is performed by combining the sample containing the test nucleic acid with a set of oligonucleotide tags 302 (containing the barcodes 132) that are releasably-attached to beads 308 prior to the partitioning step. The oligonucleotides 302 may comprise at least a primer region 316 and a barcode 132 region. Between oligonucleotides 302 within a given partition, the barcode region 132 is substantially the same barcode sequence, but as between different partitions, the barcode region in most cases is a different barcode sequence. In some embodiments, the primer region 316 is an N-mer (either a random N-mer or an N-mer designed to target a particular sequence) that is used to prime the fragments 306 within the sample within the partitions. In some cases, where the N-mer is designed to target a particular sequence, the primer region 316 is designed to target a particular chromosome (e.g., human chromosome 1, 2, 3, 4, 5, 6, 7, 8, 9, 10, 11, 12, 13, 14, 15, 16, 17, 18, 19, 20, 21, 22, X, or Y), or region of a chromosome, e.g., an exome or other targeted region. In some cases, the N-mer is designed to target a particular gene or genetic region, such as a gene or region associated with a disease or disorder (e.g., cancer). In some cases, the N-mer is designed to target a particular structural variation. Within the partitions, an amplification reaction is conducted using the primer sequence 316 (e.g. N-mer) to prime the test nucleic acid fragments 306 at different places along the length of the fragment. As a result of the amplification, each partition contains amplified products of the nucleic acid 602 that are attached to an identical or near-identical barcode, and that represent overlapping, smaller fragments of the nucleic acids in each partition. The barcode 132 therefore serves as a marker that signifies that a set of nucleic acids originated from the same partition, and thus potentially also originated from the same test nucleic acid fragment 306. It will be appreciated that there are typically several fragments 306 in any given partition. Nevertheless, in typical embodiments, fragments 306 that are in the same partition typically do not have any significant overlap and so it is possible to localize the amplified sequence reads to the correct fragment 304 in any given partition. Following amplification, the amplified nucleic acids are pooled, sequenced to form sequence reads, and aligned using a sequencing algorithm. Because shorter sequence reads may, by virtue of their associated barcode sequences, be aligned and attributed to a single, long originating fragment of the test nucleic acid 602, all of the identified variants on that sequence can be attributed to a single originating fragment 306 and single originating chromosome of the test nucleic acid 602. Further, by aligning multiple co-located variants across multiple long fragments 306, one can further characterize that chromosomal contribution. Accordingly, conclusions regarding the phasing of particular genetic variants may then be drawn. Such information may be useful for identifying haplotypes, which are generally a specified set of genetic variants that reside on the same nucleic acid strand or on different nucleic acid strands. Moreover, additionally or alternatively, structural variants are identified.

In some embodiments, referring to FIG. 3A, the co-partitioned oligonucleotide tags 302 also comprise functional sequences in addition to the barcode sequence 132 and the primer region sequence 316. For instance, in some embodiments, the co-partitioned oligonucleotide tags 302 also comprise other functional sequences useful in the processing of the partitioned nucleic acids such as targeted or random/universal amplification primer sequences for amplifying test nucleic acid fragments 306 within the partitions 304 while attaching the associated barcode sequences, sequencing primers, hybridization or probing sequences, e.g., for identification of presence of the sequences, or for pulling down barcoded nucleic acids, or any of a number of other potential functional sequences. See, for example, the disclosure on co-partitioning of oligonucleotides and associated barcodes and other functional sequences, along with sample materials as described in, for example, U.S. Patent Application Nos. 61/940,318, filed Feb. 7, 2014, 61/991,018, Filed May 9, 2014, and U.S. patent application Ser. No. 14/316,383, filed on Jun. 26, 2014, as well as U.S. patent application Ser. No. 14/175,935, filed Feb. 7, 2014, the full disclosures of which is hereby incorporated by reference in their entireties.

In one exemplary process, beads are provided, where each such bead includes large numbers of the above described oligonucleotides releasably attached to the beads. In such embodiments, all of the oligonucleotides attached to a particular bead include the same nucleic acid barcode sequence, but a large number of diverse barcode sequences are represented across the population of beads used. Typically, the population of beads provides a diverse barcode sequence library that includes at least 1000 different barcode sequences, at least 10,000 different barcode sequences, at least 100,000 different barcode sequences, or in some cases, at least 1,000,000 different barcode sequences. Additionally, each bead typically is provided with large numbers of oligonucleotide molecules attached. In particular, the number of molecules of oligonucleotides including the barcode sequence on an individual bead may be at least about 10,000 oligonucleotides, at least 100,000 oligonucleotide molecules, at least 1,000,000 oligonucleotide molecules, at least 100,000,000 oligonucleotide molecules, and in some cases at least 1 billion oligonucleotide molecules.

In some embodiments, the oligonucleotides are releasable from the beads upon the application of a particular stimulus to the beads. In some cases, the stimulus is a photo-stimulus, e.g., through cleavage of a photo-labile linkage that may release the oligonucleotides. In some cases, a thermal stimulus is used, where elevation of the temperature of the beads environment results in cleavage of a linkage or other release of the oligonucleotides form the beads. In some cases, a chemical stimulus is used that cleaves a linkage of the oligonucleotides to the beads, or otherwise results in release of the oligonucleotides from the beads.

In some embodiments, the beads including the attached oligonucleotide tags 302 are co-partitioned with the individual samples, such that a single bead and a single sample are contained within an individual partition. In some cases, where single bead partitions are desired, it may be desirable to control the relative flow rates of the fluids such that, on average, the partitions contain less than one bead per partition, in order to ensure that those partitions that are occupied, are primarily singly occupied. Likewise, in some embodiments, the flow rate is controlled to provide that a higher percentage of partitions are occupied, e.g., allowing for only a small percentage of unoccupied partitions. In preferred aspects, the flows and channel architectures are controlled as to ensure a desired number of singly occupied partitions, less than a certain level of unoccupied partitions and less than a certain level of multiply occupied partitions.

FIG. 3 of U.S. Patent Application No. 62/072,214, filed Oct. 29, 2014, entitled "Analysis of Nucleic Acid Sequences," which is hereby incorporated by reference and the portions of the specification describing FIG. 3 provide a detailed example of one method for barcoding and subsequently sequencing a test nucleic acid (referred to in the reference as a "sample nucleic acid") in accordance with one embodiment of the present disclosure. As noted above, while single bead occupancy may be the most desired state, it will be appreciated that multiply occupied partitions, or unoccupied partitions may often be present. FIG. 4 of U.S. Patent Application No. 62/072,214, filed Oct. 29, 2014, entitled "Analysis of Nucleic Acid Sequences," which is hereby incorporated by reference and the portions of the specification describing FIG. 4 provide a detailed example of a microfluidic channel structure for co-partitioning samples and beads comprising barcode oligonucleotides in accordance with one embodiment of the present disclosure.

Once co-partitioned, the oligonucleotide tags 302 disposed upon the bead are used to barcode and amplify the partitioned samples. One process for use of these barcode oligonucleotides in amplifying and barcoding samples is described in detail in U.S. Patent Application Nos. 61/940,318, filed Feb. 7, 2014, 61/991,018, filed May 9, 2014, and Ser. No. 14/316,383, filed on Jun. 26, 2014, the full disclosures of which are hereby incorporated by reference in their entireties. Briefly, in one aspect, the oligonucleotides present on the beads that are co-partitioned with the samples are released from their beads into the partition with the samples. The oligonucleotides typically include, along with the barcode sequence 132, a primer sequence at its 5' end 316. In some embodiments, this primer sequence is a random oligonucleotide sequence intended to randomly prime numerous different regions of the samples. In some embodiments the primer sequence 316 is a specific primer sequence targeted to prime upstream of a specific targeted region of the sample.

Once released, the primer portion of the oligonucleotide anneals to a complementary region of test nucleic acid fragments 306 in the partition. Extension reaction reagents, e.g., DNA polymerase, nucleoside triphosphates, co-factors (e.g., $Mg^{2+}$ or $Mn^{2+}$ etc.), that are also co-partitioned with the fragments 306 and beads 304, extend the primer sequence using the fragments 306 as a template, to produce a complementary sequence to the strand of the test nucleic fragment 306 to which the primer annealed, and this complementary sequence includes the oligonucleotide 302 and its associated barcode sequence 132. Annealing and extension of multiple primers to different portions of the fragments 306 in the partition 304 may result in a large pool of overlapping complementary portions of the test nucleic acid fragments 306, each possessing its own barcode sequence 132 indicative of the partition 304 in which it was created. In some cases, these complementary fragments may themselves be used as a template primed by the oligonucleotides present in the partition 304 to produce a complement of the complement that again, includes the barcode sequence 132. In some cases, this replication process is configured such that when the first complement is duplicated, it produces two complementary sequences at or near its termini, to allow the formation of a hairpin structure or partial hairpin structure that reduces the ability of the molecule to be the basis for producing further iterative copies. A schematic illustration of one example of this is shown in FIG. 3F.

As FIG. 3A shows, oligonucleotides 302 that include a barcode sequence 132 are co-partitioned in, e.g., a droplet 304 in an emulsion, along with a sample test nucleic acid fragment 306. In some embodiments, the oligonucleotides 302 are provided on a bead 308 that is co-partitioned with the test nucleic acid fragment 306. The oligonucleotides 302 are preferably releasable from the bead 308, as shown in FIG. 3A, panel (A). As shown in FIG. 3A panel (B), the oligonucleotides 302 includes a barcode sequence 132, in addition to one or more functional sequences, e.g., sequences 312, 132 and 316. For example, oligonucleotide 302 is shown as further comprising attachment sequence 312 that may function as an attachment or immobilization sequence for a given sequencing system, e.g., a P5 sequence used for attachment in flow cells of an ILLUMINA, HISEQ or MISEQ system. In other words, attachment sequence 312 is used to reversibly attach oligonucleotide 302 to a bead 308 in some embodiments. As shown in FIG. 3A, panel B, the oligonucleotide 302 also includes a primer sequence 316, which may include a random or targeted N-mer (discussed above) for priming replication of portions of the sample test nucleic acid fragment 306. Also included within exemplary oligonucleotide 302 of FIG. 3A, panel B, is a sequence 310 which may provide a sequencing priming region, such as a "read1" or R1 priming region, that is used to prime polymerase mediated, template directed sequencing by synthesis reactions in sequencing systems. In many cases, the barcode sequence 132, immobilization sequence 312 and exemplary R1 sequence 310 may be common to all of the oligonucleotides 302 attached to a given bead. The primer sequence

316 may vary for random N-mer primers, or may be common to the oligonucleotides on a given bead for certain targeted applications.

Figure 3B:
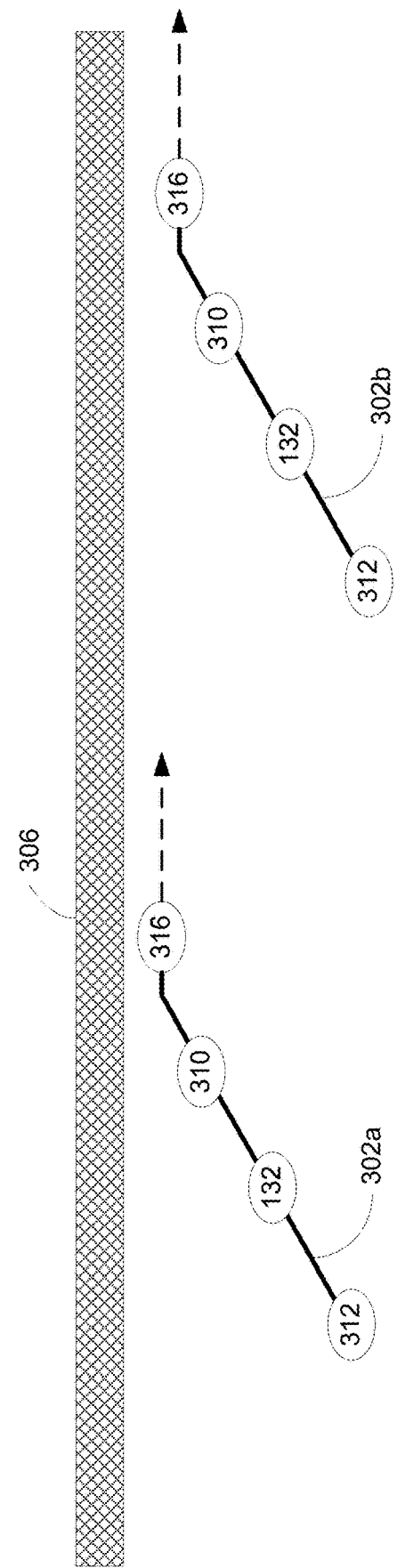
Figure 4:
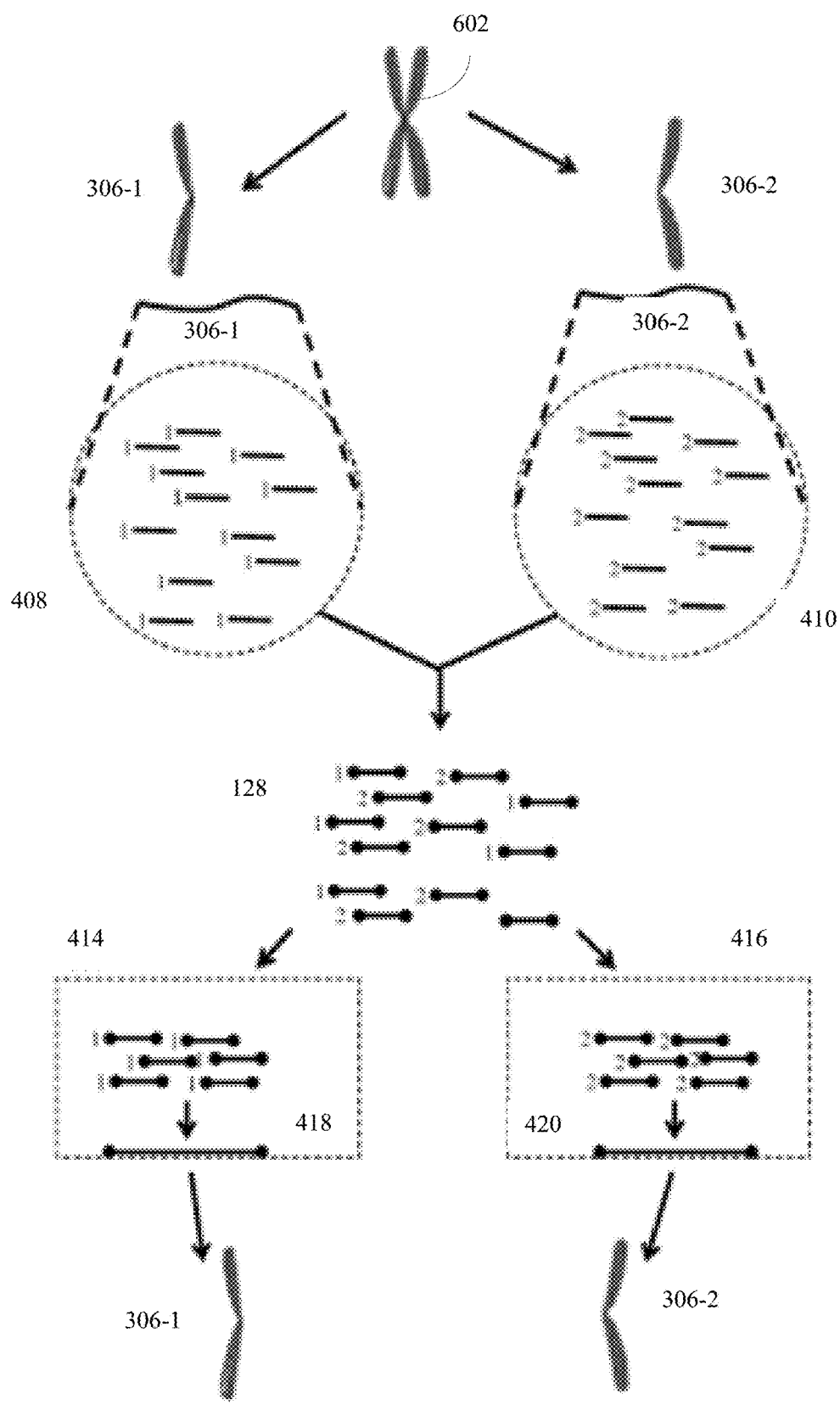
FIG. 4 illustrates a method of identifying bins of sequence reads in accordance with some embodiments of the present disclosure.

Referring to FIG. 3B, based upon the presence of primer sequence 316, the oligonucleotides 302a and 302b are able to prime the test nucleic acid fragment 306, which allows for extension of the oligonucleotides 302a and 302b using polymerase enzymes and other extension reagents also co-portioned with the bead 304 and sample test nucleic acid fragment 306.

Figure 3C:
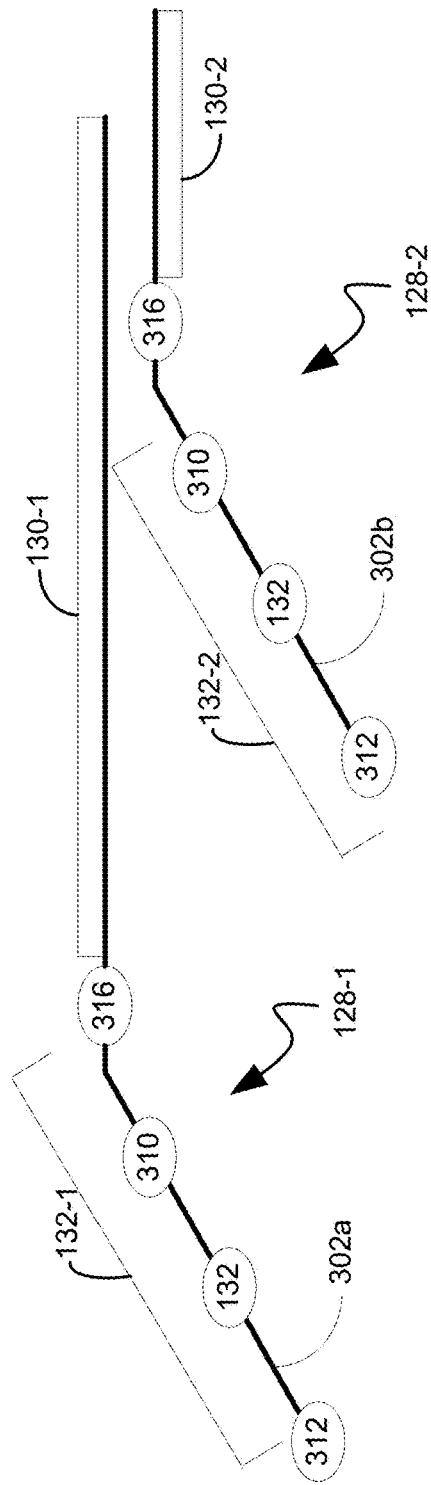

As shown in FIG. 3C, following extension of the oligonucleotides that, for random N-mer primers, would anneal to multiple different regions of the sample test nucleic acid fragment 306; multiple overlapping complements or fragments of the test nucleic acid fragment 306 are created, e.g., fragments 130-1 and 130-2. As such, FIG. 3C illustrates (A) obtaining a plurality of sequence reads, wherein each respective sequence read 128 in the plurality of sequence reads comprises a first portion 130 that corresponds to a subset of the test nucleic acid 602 and a common second portion 132 that forms an barcode that is independent of the sequence of the larger contiguous nucleic acid 602 and that identifies a partition 304, in a plurality of partitions, in which the respective sequence read was formed (e.g., barcode sequence 132).

Although including sequence portions that are complementary to portions of test nucleic acid, e.g., sequences 306-1 and 306-2, these constructs are generally referred to herein as comprising fragments of the sample test nucleic acid 602, having the attached barcode sequences. As will be appreciated, the replicated portions of the template sequences as described above are often referred to herein as "fragments" of that template sequence. Notwithstanding the foregoing, however, the term "fragment" encompasses any representation of a portion of the originating test nucleic acid sequence, e.g., a template or sample nucleic acid, including those created by other mechanisms of providing portions of the template sequence, such as actual fragmentation of a given molecule of sequence, e.g., through enzymatic, chemical or mechanical fragmentation. In preferred aspects, however, fragments of a test nucleic acid sequence will denote replicated portions of the underlying sequence or complements thereof.

Figure 3D:
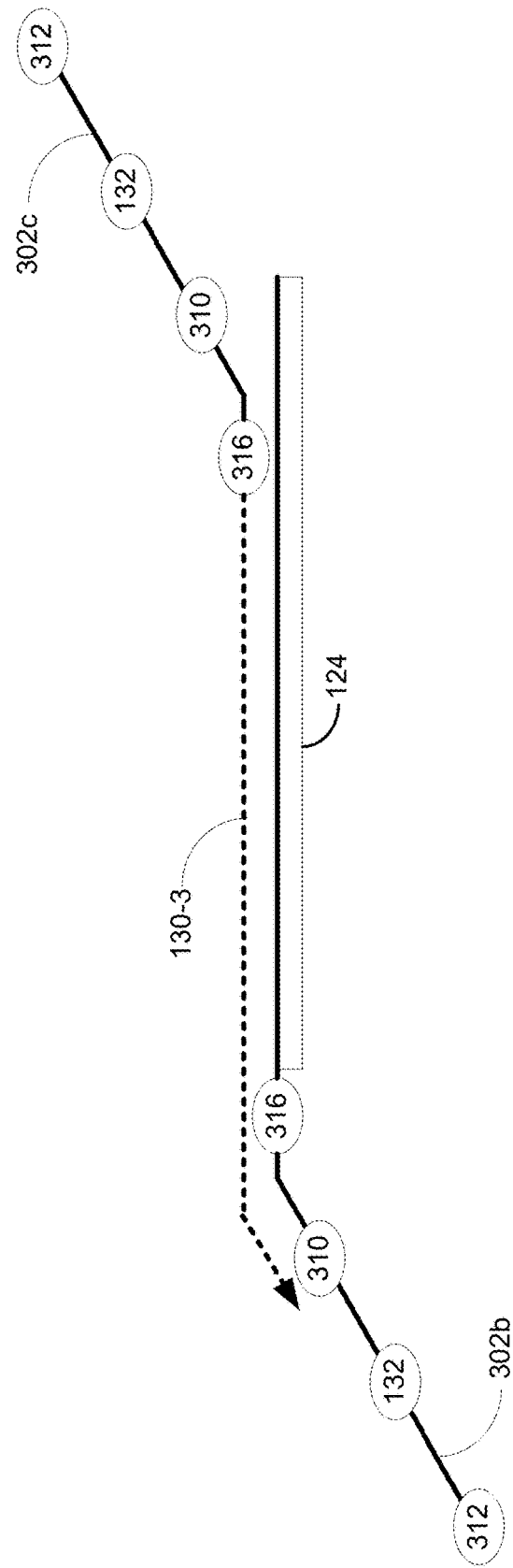
Figure 3E:
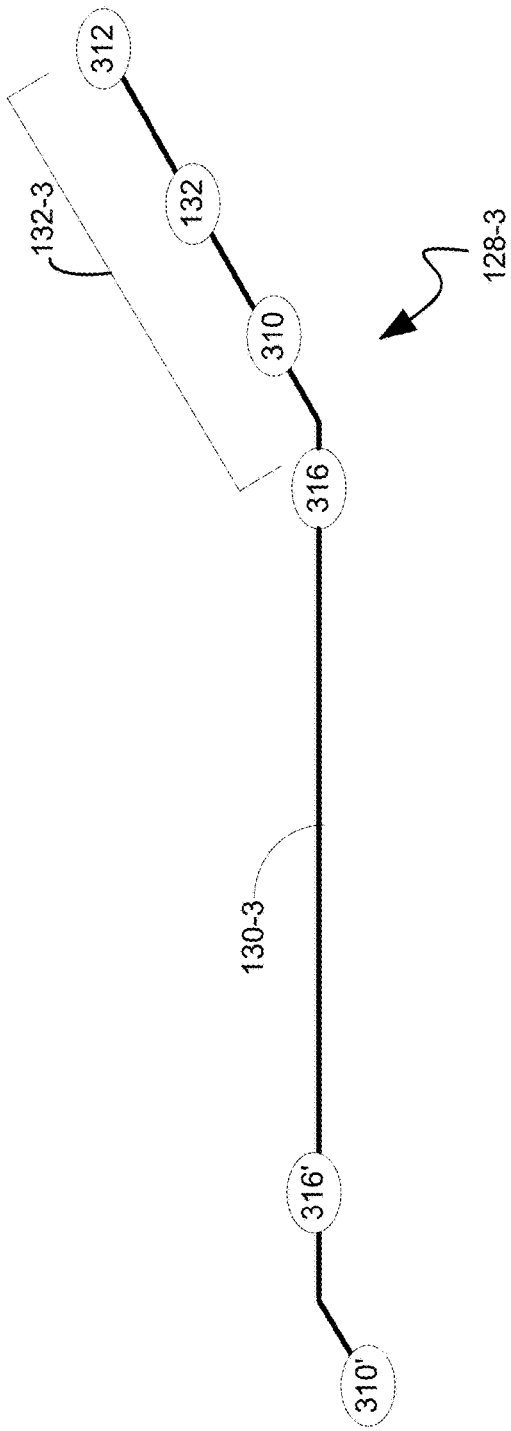
Figure 3F:
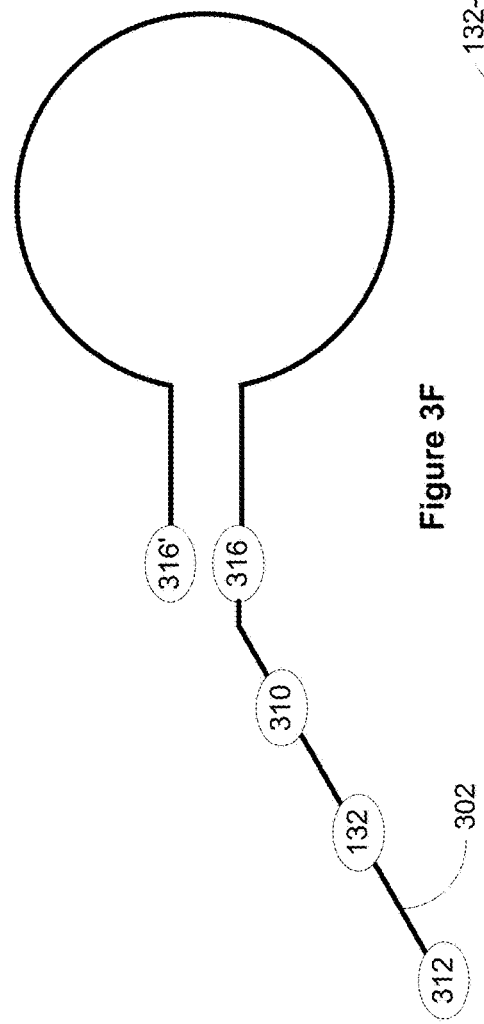
Figure 3G:
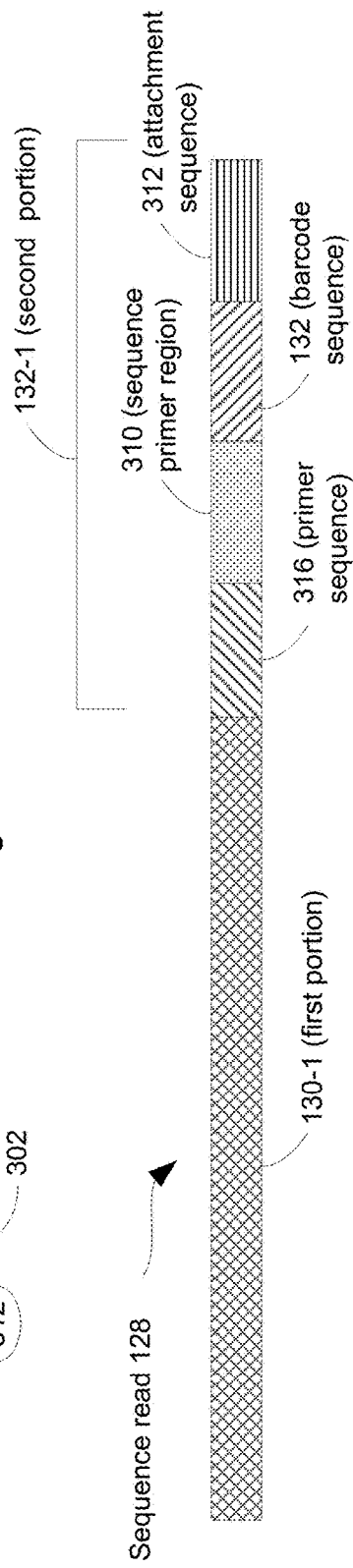
Figure 3H:
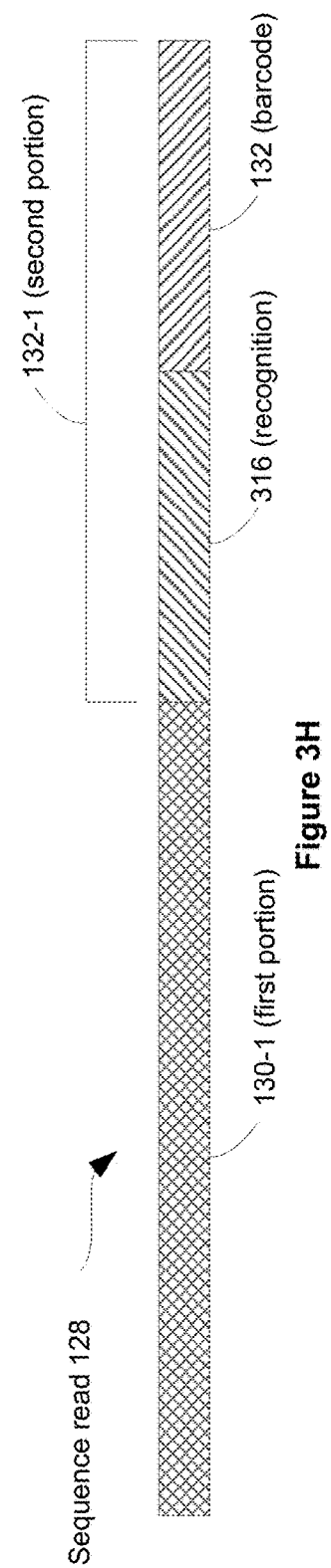

The barcoded nucleic acid fragments of FIG. 3B may then be subjected to characterization, e.g., through sequence analysis, or they may be further amplified in the process, as shown in FIG. 3D. For example, additional oligonucleotides, e.g., oligonucleotide 302c, also released from bead 308, may prime the fragment 302b. In particular, again, based upon the presence of the random N-mer primer 316 in oligonucleotide 302c (which in many cases will be different from other random N-mers in a given partition) the oligonucleotide anneals with the fragment 302b, and is extended to create a complement 130-3 to at least a portion of fragment 302b which comprises a duplicate of a portion of the test nucleic acid sequence. Extension of the oligonucleotide 302b continues until it has replicated through the oligonucleotide portion 130 of fragment 302b. As noted elsewhere herein, and as illustrated in FIG. 3D, the oligonucleotides may be configured to promptly stop in the replication by the polymerase at a desired point, e.g., after replicating through sequences 316 and 310 of oligonucleotide 302b that is included within fragment. As described herein, this may be accomplished by different methods, including, for example, the incorporation of different nucleotides and/or nucleotide analogues that are not capable of being processed by the polymerase enzyme used. For example, this may include the inclusion of uracil containing nucleotides within the sequence region 310 to prevent a non-uracil tolerant polymerase to cease replication of that region. As a result, referring to FIG. 3E, a sequence read 128-3 is created that includes the full-length oligonucleotide 302b at one end, including the barcode sequence 132, the attachment sequence 312, the R1 primer region 310, and the random N-mer sequence 316. At the other end of the sequence is included the complement 316' to the random N-mer of the first oligonucleotide 302, as well as a complement to all or a portion of the R1 sequence, shown as sequence 310'. The R1 sequence 310 and its complement 310' are then able to hybridize together to form a partial hairpin structure 360. As will be appreciated, because the random N-mers differ among different oligonucleotides, these sequences and their complements would not be expected to participate in hairpin formation, e.g., sequence 316', which is the complement to random N-mer 316, would not be expected to be complementary to random N-mer sequence 316b. This would not be the case for other applications, e.g., targeted primers, where the N-mers would be common among oligonucleotides within a given partition.

By forming these partial hairpin structures, it allows for the removal of first level duplicates of the sample sequence from further replication, e.g., preventing iterative copying of copies. The partial hairpin structure also provides a useful structure for subsequent processing of the created fragments, e.g., fragment 130-3.

All of the sequence reads 128 from multiple different partitions may then be pooled for sequencing on high throughput sequencers as described herein. Because each sequence read 128 is coded as to its partition of origin, the sequence of that sequence read may be attributed back to its origin based upon the presence of the barcode 132. Such sequence reads, and analysis of such sequence reads, form the basis of the disclosed nucleic acid sequencing dataset 126.

This is schematically illustrated in FIG. 4. As shown in one example, a test nucleic acid fragment 306-1 and a test nucleic acid fragment 306-2 are each partitioned along with their own sets of barcode oligonucleotides 132 as described above. Within each partition, each fragment (306-1 and 306-2) is then processed to separately provide overlapping sequence reads 128 of the fragments 306-1 and 306-2 to form a respective set of sequence reads 414 and 416. This processing provides sequence reads 414 with a barcode sequence 132 that is the same for each of the sequence reads 414 derived from a particular first fragment 306-1. As shown, the set of sequence reads 414 is denoted by "1" while the set of sequence reads 416 is denoted by "2". A diverse library of barcodes may be used to differentially barcode large numbers of different sets of fragment reads. However, it is not necessary for every sequence read in a given partition to be barcoded with different barcode sequence. In fact, in many cases, multiple different first fragments may be processed concurrently to include the same barcode sequence. Diverse barcode libraries are described in detail elsewhere herein.

The sets of sequence reads may then be pooled for sequencing using, for example, sequence by synthesis technologies available from Illumina or Ion Torrent division of Thermo Fisher, Inc. Once sequenced, the sequence reads 128 can be attributed to their respective fragment set, e.g., as shown in aggregated reads, at least in part based upon the included barcodes, and optionally, and preferably, in part based upon the sequence of the fragment itself. The attributed sequence reads for each fragment set are then assembled to provide the assembled sequence for each sample fragment, e.g., sequences 418 and 420, which in turn, may be further attributed back to their respective original fragments (306-1 and 302-2). Methods and systems for assembling genomic sequences are described in, for example, U.S. Provisional Patent Application No. 62/017,589, filed Jun. 26, 2014, the full disclosure of which is hereby incorporated by reference in its entirety.

In some embodiments, the biological sample is from a multi-chromosomal species and the test nucleic acid 602 comprises a plurality of nucleic acids collectively representing a plurality of chromosomes from the multi-chromosomal species (208). In some embodiments, the barcode in the second portion 132 of each respective sequence read in the plurality of sequence reads encodes a unique predetermined value selected from the set $\{1, \ldots, 1024\}$, $\{1, \ldots, 4096\}$, $\{1, \ldots, 16384\}$, $\{1, \ldots, 65536\}$, $\{1, \ldots, 262144\}$, $\{1, \ldots, 1048576\}$, $\{1, \ldots, 4194304\}$, $\{1, \ldots, 16777216\}$, $\{1, \ldots, 67108864\}$, or $\{1, \ldots, 1 \times 10^{12}\}$ (210). For instance, consider the case in which the barcode sequence 132 is represented by a set of five nucleotide positions. In this instance, each nucleotide position contributes four possibilities (A, T, C or G), giving rise, when all five positions are considered, to $4 \times 4 \times 4 \times 4 \times 4 = 1024$ possibilities. As such, the five nucleotide positions form the basis of the set $\{1, \ldots, 1024\}$. In other words, when the barcode sequence 132 is a 5-mer, the second portion 132 of each sequence read 128 encodes a unique predetermined value selected from the set $\{1, \ldots, 1024\}$. Likewise, when the barcode sequence 132 is represented by a set of six nucleotide positions, the six nucleotide positions collectively contribute $4 \times 4 \times 4 \times 4 \times 4 \times 4 = 4096$ possibilities. As such, the six nucleotide positions form the basis of the set $\{1, \ldots, 4096\}$. In other words, when the barcode sequence 132 is a 6-mer, the second portion 132 of each sequence read 128 encodes a unique predetermined value selected from the set $\{1, \ldots, 4096\}$.

In some embodiments, the barcode in the second portion 132 of a sequence read in the plurality of sequence reads is localized to a contiguous set of oligonucleotides within the sequence read (212). In one such exemplary embodiment, the contiguous set of oligonucleotides is an N-mer, where N is an integer selected from the set $\{4, \ldots, 20\}$ (214). In other words, in some embodiments, the barcode 132 in, for instance FIG. 3B, panel B, is a contiguous set of nucleotide positions (e.g., 4 contiguous nucleotide positions, 5 contiguous nucleotide positions, 6 contiguous nucleotide positions, 7 contiguous nucleotide positions, 8 contiguous nucleotide positions, 9 contiguous nucleotide positions, 10 contiguous nucleotide positions, 11 contiguous nucleotide positions, 12 contiguous nucleotide positions, 13 contiguous nucleotide positions, 14 contiguous nucleotide positions, 15 contiguous nucleotide positions, 16 contiguous nucleotide positions, 17 contiguous nucleotide positions, 18 contiguous nucleotide positions, 19 contiguous nucleotide positions, or 20 contiguous nucleotide positions) within oligonucleotide tag 302 which ultimately becomes second portion 132 upon transcription of the test nucleic acid.

By contrast, in some embodiments, the barcode in the second portion of a sequence read in the plurality of sequence reads is localized to a noncontiguous set of oligonucleotides within the sequence read (216). In one such exemplary embodiment, the predetermined noncontiguous set of nucleotides collectively consists of N nucleotides, where N is an integer in the set $\{4, \ldots, 20\}$ (218). As an example, in some embodiments, referring to FIG. 3A, panel B, barcode sequence 132 comprises a first set of contiguous nucleotide positions at a first position in oligonucleotide tag 302 and a second set of contiguous nucleotide positions at a second position in oligonucleotide tag 302, that is displaced from the first set of contiguous nucleotide positions by a spacer. In one specific example, the barcode sequence 132 comprises $(X1)_n Y_z (X2)_m$, where X1 is n contiguous nucleotide positions, Y is a constant predetermined set of z contiguous nucleotide positions, and X2 is m contiguous nucleotide positions. In this example, the barcode in the second portion of the sequence read 128 produced by a schema invoking this exemplary barcode is localized to a noncontiguous set of oligonucleotides, namely $(X1)_n$ and $(X2)_m$. This is just one of many examples of noncontiguous formats for barcode sequence 132.

In some embodiments, the first sequence read in the plurality of sequence reads corresponds to a subset of the test nucleic acid that is 2×36 bp, 2×50 bp, 2×76 bp, 2×100 bp, 2×150 bp or 2×250 bp, where the terminology 2×N by means that the sequence read has two reads of length N base pairs from a single piece of nucleic acid (e.g., from a text nucleic acid obtained from a biological sample) that are separated by an unspecified length. In some embodiments this unspecified length is between 200 to 1200 base pairs. In some embodiments, a first sequence read in the plurality of sequence reads represents at least 25 bp, at least 30 bp, at least 50 bp, at least 100 bp, at least 200 bp, at least 250 bp, at least 500 bp, less than 500 bp, less than 400 bp, or less than 300 bp of a single piece of nucleic acid (e.g., from a text nucleic acid obtained from a biological sample). (220).

Obtaining Bin Information.

Figure 5:
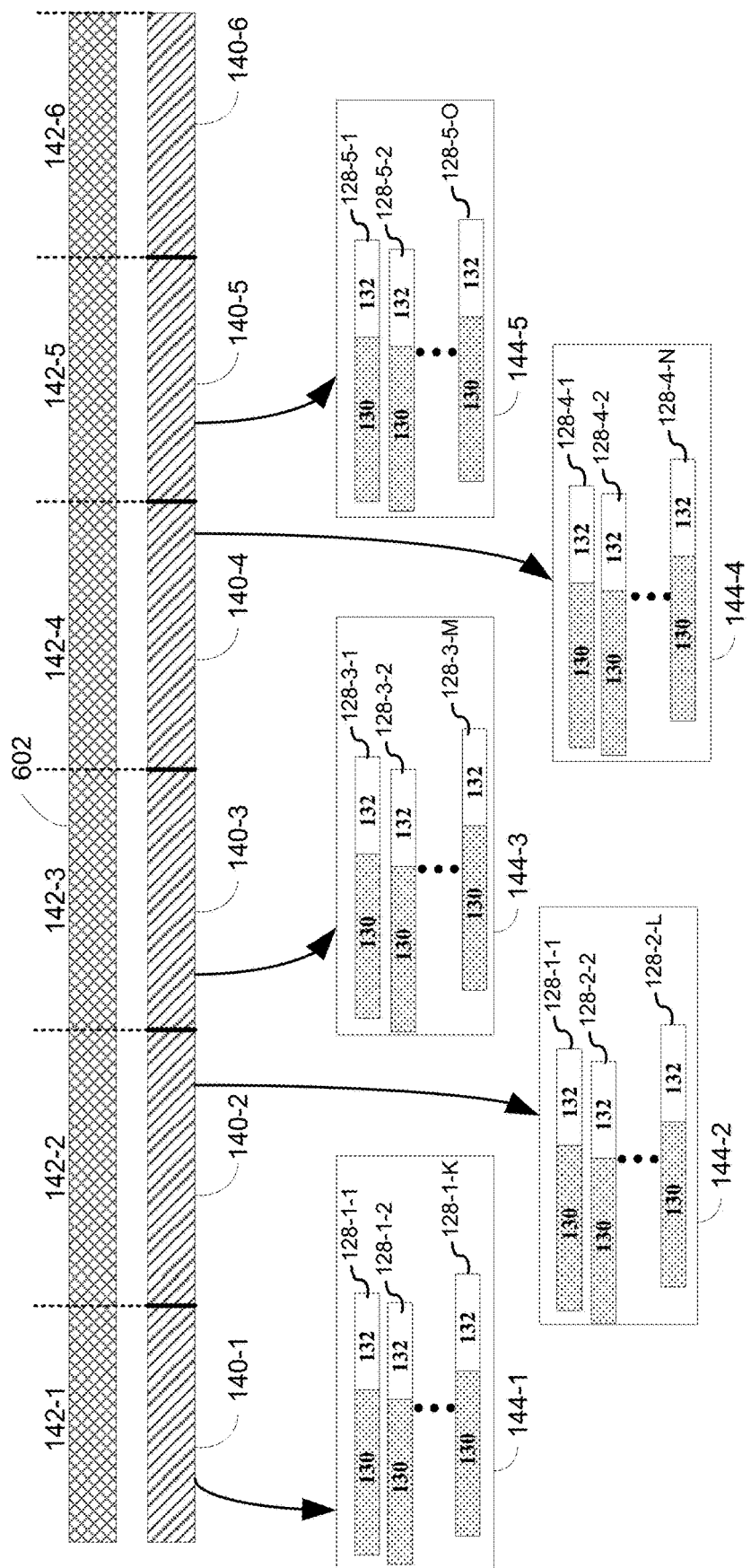
FIG. 5 illustrates bin information in accordance with some embodiments of the present disclosure.

In accordance with the disclosed systems and methods, bin information for a plurality of bins is obtained (222). Each respective bin 140 in the plurality of bins represents a different portion of the test nucleic acid. The bin information identifies, for each respective bin in the plurality of bins, a set of sequence reads in a plurality of sets of sequence reads. FIG. 5 illustrates. In FIG. 5, a test nucleic acid 602 is depicted. Further shown in FIG. 5, each respective bin 140 in a plurality of bins represents a different portion 142 of the test nucleic acid 602. Further, the bin information identifies, for each respective bin 140 in the plurality of bins, a set 144 of sequence reads 128 corresponding to the respective bin.

Continuing to refer to FIG. 5, each sequence read 128 in each set 144 of sequence reads in the plurality of sets of sequence reads is in the plurality of sequence reads. That is, each sequence read 128 corresponds to a portion 142 of the test nucleic acid 602 that has been binned.

Each respective sequence read 128 in each respective set 144 of sequence reads in the plurality of sets of sequence reads has a respective first portion 130 that corresponds to a subset of the test nucleic acid that at least partially overlaps the different portion 142 of the test nucleic acid 602 that is represented by the bin 140 corresponding to the respective set of sequence reads. For example, referring to set 144-1 illustrated in FIG. 5, each sequence read 128-1-1, . . . , 128-1-K, includes a first portion 130 that corresponds to at least a subset of the region 142-1 of the test nucleic acid 140-1 corresponding to bin 140-1. It will be appreciated from the schema and constructs of FIG. 3, that in typical embodiments, the first portions 130 of sequence reads 128-1-1, . . . , 128-1-K of set 144-1 are of different lengths and are displaced, yet overlapping, with respect to each other. In some embodiments, such first portions 130 may include some nucleotide positions from adjacent regions 142 of the test nucleic acid 602. In some embodiments the first portions 130 only represent a subset of the region 142 of the test nucleic acid 602 of the bin 140.

In some embodiments, the region 142 of the test nucleic acid corresponding to a bin 140—is substantially longer than any given first portion 130 in the set 144 of sequence reads 128 within the bin. Moreover, in some embodiments, a given set 144 of sequence reads 128 includes five or more different barcode sequences 132, ten or more different barcode sequences 132, fifteen or more different barcode sequences 132, twenty or more different barcode sequences 132, twenty-five or more different barcode sequences 132, thirty or more different barcode sequences 132, thirty-five or more different barcode sequences 132, forty or more different barcode sequences 132, forty-five or more different barcode sequences 132, or fifty or more different barcode sequences 132.

In some embodiments, two or more, three or more, four or more, five or more, six or more, seven or more, eight or more, nine or more, ten or more, or eleven or more sequence reads 128 in a bin 144 have the same barcode sequences 132. In some embodiments, each sequence read 128 in a bin 144 has a different barcode sequence 132.

In some embodiments, each bin 140 in the plurality of bins represents at least 20 kbp, at least 50 kbp, at least 100 kbp, at least 250 kbp, or at least 500 kbp of the test nucleic acid (224). In other words, referring to FIG. 5, in some embodiments, the portion 142-1 of test nucleic acid 602 represented by bin 140-1 is at least 20 kbp, at least 50 kbp, at least 100 kbp, at least 250 kbp, or at least 500 kbp.

In some embodiments, there is no overlap between each different portion 406 of the test nucleic acid represented by each respective bin in the plurality of bins (226). Such an embodiment is illustrated in FIG. 5. In such embodiments it is possible for overlap in the first portions 130 of the sequence reads 128, in the corresponding bin 144, with neighboring regions 142. In some embodiments, there is no overlap between each different portion 406 of the test nucleic acid represented by each respective bin in the plurality of bins (226), but there is some overlap in the first portions 130 of the sequence reads 128 in the corresponding bin 144 with neighboring portions 406.

In some embodiments, each respective sequence read 128 in each respective set 144 of sequence reads in the plurality of sequence reads has a respective first portion 130 that corresponds to a subset of the test nucleic acid 602 that fully overlaps the different portion 142 of the test nucleic acid 602 that is represented by the bin 144 corresponding to the respective set 144 of sequence reads. In other words, using bin 144-1 of FIG. 5 as an example, in some embodiments, each first portion 130 of each sequence read 128-1-1, . . . 128-1-k, includes a full copy of regions 142-1.

In some embodiments, the plurality of bins comprises 10,000 or more bins, 100,000 or more bins, or 1,000,000 or more bins (230).

Determining a Number of Unique Barcodes Common to Two Sets of Sequence Reads.

The method continues with a determination of the number of unique barcodes that are found in both the first and second set of sequence reads in the plurality of sequence reads (232). An example of such a determination is the determination of how many sequence reads 128-1-X in set 144-1 have a barcode sequence 132 that is the same as a barcode sequence 132 in a sequence read 128-2-Y in set 144-2. This determination results in a number of unique sequence barcodes. For example, consider the case in which there are five unique barcodes that are found in the sequence reads 128-1-X in set 144-1 as well as in the sequence reads 128-2-Y in set 144-2. In this instance, the number of distinct common barcodes is five.

Determine a Probability or Likelihood that the Number is Attributable to Chance.

The method continues by determining a probability or likelihood that the above-identified number determined at (232) is attributable to chance. This is done by comparison of a metric based upon the number to a threshold criterion (234). When the metric satisfies the threshold criterion, a structural variation is deemed to have occurred in (i) the different portion of the test nucleic acid that is represented by the first set of sequence reads and/or (ii) the different portion of the test nucleic acid that is represented by the second set of sequence reads.

For example, continuing to use the example of the comparison of sets 144-1 and 144-2 of FIG. 5 from above, a probability or likelihood that the number determined at (232) is attributable to chance is made. This is done by comparison of a metric based upon (i) the five unique barcodes (barcode sequences 132) common to set 144-1 and set 144-2 (ii) to a threshold criterion (234). When the metric satisfies the threshold criterion, a structural variation is deemed to have occurred in (i) portion 142-1 of the test nucleic acid 602 and/or (ii) the different portion 142-2 of the test nucleic acid.

In some embodiments, the metric is computed as:

$$p = \Pi_i^n f_{b_i} \quad (A)$$

where, $\{b_1, b_2, \ldots, b_n\}$ is the set of n unique barcodes (e.g., barcode sequences 132) that is found in both the first and second sets of sequence reads in the plurality of sequence reads, i is an integer index to n, and $f_{b_i}$ is the fraction of the plurality of bins in which the first portion of barcode $b_i$ appears (236). In other words, the product of formula A is taken over the distinct common barcodes, not over the common reads.

For instance, in the comparison of sets 144-1 to 144-2, the metric is computed as:

$$p = \Pi_i^n f_{b_i} \quad (1)$$

where, $\{b_1, b_2, \ldots, b_n\}$ is the set of n barcodes in set 144-1 having unique (that is, unique across the set $\{b_1, b_2, \ldots, b_n\}$) barcode sequences 132 that are also found in the set 144-2, i is an integer index to n, and $f_{b_i}$ is the fraction of the plurality of bins in which barcode $b_i$ appears (236). More specifically, in embodiments in which the first portion of the sequence read 128 includes a respective barcode sequence 132, $f_{b_i}$ is the fraction of the plurality of bins in which the respective barcode sequence 132 appears.

The probability in (1) is the probability of observing all n barcodes at the same time, assuming that they occur independently of each other. If this probability is small, the hypothesis that the overlap between the first bin and the second bin is random.

In some embodiments, the metric is computed as:

$$p = \Pi_i^n (1 - P_{Binom}(0; \max(n_1, n_2) f_{b_i})) \quad (2)$$

where, $\{b_1, b_2, \ldots, b_n\}$ is the set of n unique barcodes that is found in both the first and second set of sequence reads, $n_1$ is the number of unique barcodes in the first set of sequence reads, $n_2$ is the number of unique barcodes in the second set of sequence reads, i is an integer index to n, $f_{b_i}$ is the fraction of the plurality of bins in which the barcode $b_i$ appears, and $P_{Binom}(0; \max(n_1, n_2) f_{b_i})$ is a cumulative distribution function of a Binomial distribution. $P_{Binom}(0; \max(n_1, n_2) f_{b_i})$ is equated to a probability that, given max $(n_1, n_2)$ barcodes, each of which has a $f_{b_i}$ probability of carrying barcode at least one occurrence of $b_i$ in $\{b_1, b_2, \ldots, b_n\}$ is achieved. This assumes that the probability that a sequence read has barcode $b_i$ is equal to the frequency of the barcode in the plurality of barcodes.

Computing the probability in (2) or (1) requires iteration over all common barcodes between each pair of bins. Since it is typically the case that most pairs of bins will not have a significant sequence barcode overlap, an initial set of candidate pairs of bins can be obtained by performing a less computationally intense test that assumes that all barcodes have the same frequency. In some such embodiments, the metric is computed as:

$$p=1-P_{Binom}(n;n_1,n_2/B) \quad (3)$$

where n is the number of unique barcodes that is found in both the first and second set of sequence reads, $n_1$ is the number of unique barcodes in the first set of sequence reads, $n_2$ is the number of unique barcodes in the second set of sequence reads, and B is the total number of unique barcodes across the plurality of bins. Equation (3) is the probability of observing more than n overlapping barcodes assuming that all barcodes have the same frequency of appearance in the plurality of bins and are chosen at random.

Iterating over all pairs of bins genome-wide (e.g., across the plurality of bins) can be time consuming. For example, if the human genome (which is roughly $3\times10^9$ base pairs long) is binned in non-overlapping windows of size 10 kb, this would result in $3\times10^5$ bins. In other words, there would be $3\times10^5$ bins in the plurality of bins. In this case, the number of pairwise bin comparisons would be on the order of $10^{10}$. In some embodiments, to be able to perform this comparison efficiently, matrix operations are used. In particular, for each chromosome, a B×N matrix, A, is defined, where B is the number of unique barcodes present in the experiment and N is the number of bins in that chromosome. This matrix will tend to be very sparse, since only a small subset of the barcodes will appear in any given bin. To find the overlapping bins between two chromosomes (or a chromosome and itself), with respective barcode matrices $A_1$ and $A_2$ (defined as above for A), the product $V=A_1^T A_2$ is computed, where T denotes the transpose of the matrix $A_1$. If $N_1$ and $N_2$ are the number of bins in $A_1$ and $A_2$ respectively, then V will be a $N_1 \times N_2$ matrix. $V_{ij}$ will be non-zero if and only if there is barcode overlap between the $i^{th}$ bin of $A_1$ and the $j^{th}$ bin of $A_2$. The time and memory required to perform this sparse matrix multiplication depends on the number of non-zero elements in the resulting matrix, rather than on the total size of the matrix. Thus, advantageously, the time required to detect all bins that share barcodes increases with the number of such bins and not with the total number of bins.

Accordingly, in some embodiments, an identity of the first and second bin is determined using sparse matrix multiplication. In some embodiments, the sparse matrix multiplication comprises computing:

$$V=A_1^T A_2,$$

where, $A_i$ is a first $B \times N_1$ matrix of barcodes that includes those of the first bin, $A_2$ is a second $B \times N_2$ matrix of barcodes that includes those of the second bin, B is the number of unique barcodes in the plurality of bins, $N_1$ is the number of bins in $A_1$, $N_2$ is the number of bins in $A_2$, and $A_1^T$ is the transpose of matrix $A_1$.

In some embodiments, the first and second bin are in different chromosomes. Accordingly, in some such embodiments, the first bin is associated with a first chromosome of the biological sample, the second bin is associated with a second chromosome of the biological sample, $N_1$ is the number of bins associated with the first chromosome, and $N_2$ is the number of bins associated with the second chromosome.

In alternative embodiments, the first and second bins are in the same chromosome. Accordingly, in some such embodiments, the first and second bins are associated with a first chromosome of the biological sample, $N_1$ is the number of bins associated with the first chromosome, and $N_2$ equals $N_1$.

As an example of the computations of the present disclosure, with reference to FIG. 6, consider the EML4-ALK fusion, a gene fusion commonly found in the lung cancer cell line NCI-H2228. In this cell line, the intron between exons 6 and 7 of EML4 is fused to the intron between exons 20 and 21 of ALK. This creates a novel fused gene which consists of parts of both EML4 and ALK. In a sample that harbors the fusion, there will be fragments spanning the fused parts of EML4 and ALK. Therefore, the sequence reads 128 mapping to EML4 and ALK will tend to have common barcodes 132. Such barcode sharing would be much more unlikely in the absence of a fusion, since, normally, EML4 and ALK are too far apart (more than 10 million base-pairs) to be spanned by the same fragment. In a sample from the NCI-H2228 cell line, 12 barcodes 132 in common between EML4 and ALK were identified, suggesting that there were at least 12 fragments spanning the fusion region. Given the empirical frequencies of these barcodes across the plurality of bins, the probability of such an overlap occurring purely by chance, computed using metric (1) from above, is less than $10^{-8}$.

In some embodiments, the metric (e.g, metric (1), (2) or (3) from above) is deemed to satisfy the threshold criterion when p is $10^{-2}$ or less, $10^{-3}$ or less, $10^{-4}$ or less, or $10^{-5}$ or less (238).

In some embodiments, the structural variation is an insertion or deletion of 50 consecutive bases or more, 500 consecutive bases or more, or 5000 consecutive bases or more, into the different portion of the test nucleic acid that is represented by the first set of sequence reads (240).

In some embodiments, the different portion of the test nucleic acid represented by the first bin overlaps the different portion of the test nucleic acid represented by the second bin (242). In other words, referring to FIG. 5, in some embodiments sections 142 overlap each other rather than abut each other as depicted. In some such embodiments, at least 50 percent, at least 80 percent, or at least 95 percent of the different portion of the test nucleic acid 602 represented by the first bin (e.g. portion 142-1 corresponding to bin 144-1) overlaps the different portion of the test nucleic acid 602 represented by the second bin (e.g. portion 142-2 corresponding to bin 144-2) (244).

In some embodiments, the structural variation is a translocation of 50 consecutive bases or more, of 50 consecutive bases or more, 100 consecutive bases or more, 250 consecutive bases or more, 500 consecutive bases or more, 1000 consecutive bases or more, 10,000 consecutive bases or more, 20,000 consecutive bases or more, 40 kb consecutive bases or more, 100 kb consecutive bases or more, or 250 kb consecutive bases or more, into the different portion of the test nucleic acid 602 that is represented by the first set (e.g., set 144-1) of sequence reads from the different portion of the test nucleic acid that is represented by the second set (e.g., set 144-2) of sequence reads (246).

In some embodiments, the different portion of the test nucleic acid represented by the bin corresponding to the first set of sequence reads is from a first chromosome of the biological sample, and the different portion of the test nucleic acid represented by the bin corresponding to the second set of sequence reads is from a second chromosome of the biological sample, where the second chromosome is other than the first chromosome (248). In some such embodiments, the first chromosome is a paternal chromosome and the second chromosome is a maternal chromosome (250). In some such embodiments, the biological sample is human and the first chromosome is chromosome 21, 18, or 13 (252).

In some embodiments in which the structural variation is deemed to have occurred, the method further comprises treating a subject that originated the biological sample with a treatment regimen responsive to the identified structural variation (254). In some embodiments, this treatment regimen comprises a diet modification (256). For instance, in some embodiments the structural variation is associated with cancer and the diet modification includes avoidance of desserts and other foods that have high sugar content. In some embodiments, the treatment regimen comprises application of a pharmaceutical composition that inhibits or augments a biological pathway associated with the structural variation (258). Nonlimiting examples of such biological pathways are found in the KEGG database. See Kanehisa and Goto, 2000, "KEGG: Kyoto Encyclopedia of Genes and Genomes," Nucleic Acids Research 28, 27-30, which is hereby incorporated by reference herein in its entirety.

Accurately detecting structural variation relies on the ability of sequence aligners to map reads uniquely and confidently on the genome. In some instances this is not the case, even with state-of-the-art aligners such as BWA. See Heng and Durbin, 2010, "Fast and accurate long-read alignment with Burrows-Wheeler transform, "Bioinformatics, 26(5):589-95, which is hereby incorporated by reference for disclosure on BWA. For example, consider two highly homologous regions of the test nucleic acid 602, i.e. two regions with a large degree of sequence similarity. Sequence reads 128 coming from either region would align reasonably well to both regions of the test nucleic acid 602. Sequencing errors, combined with natural sequence variation, might make sequence reads 128 from such a region look like they came from its homologous partner. This can lead to a spurious barcode 132 sharing between homologous regions. Algorithms that rely on read-pair information suffer from the same problem. To be able to detect such false positive structural variants, in some embodiments a step of local realignment of sequence reads 128 around the detected breakpoints is performed. Sequence reads 128 that align with similar quality to both breakpoints of a called structural variant are discarded as spurious.

Accordingly, in some embodiments in which the metric is deemed to satisfy the threshold criterion, the method further comprises aligning each respective sequence read 128 in the number of respective sequence reads to the subset 142 (e.g., subset 142-1) of the test nucleic acid 602 corresponding to the first set of sequence reads (e.g., set 144-1) using a local realignment procedure that is more accurate than genome-wide alignment with algorithms such as BWA. Then, a first alignment quality is determined for each respective sequence read in the number of respective sequence reads against the subset of the test nucleic acid corresponding to the first set of sequence reads (e.g., subset 142-1) based on the aligning. In such embodiments, the method further comprises aligning each respective sequence read 128 in the number of respective sequence reads with the subset of the test nucleic acid 142 (e.g., subset 142-2) corresponding to the second set of sequence reads. Moreover, a second alignment quality is determined for each respective sequence read in the number of respective sequence reads against the subset of the test nucleic acid corresponding to the second set of sequence reads (e.g, subset 142-2) based on the aligning. The purpose of such alignments is to eliminate from the number of respective sequence reads those sequence reads having alignment scores that do not discriminate between the first subset (e.g., subset 141-1) and the second subset (e.g., subset 142-2). In other words, those sequence reads in which first alignment quality and the second alignment are similar are eliminated thereby resulting in a reduced number of sequence reads. With this reduced number of sequence reads, process 234 is repeated (260). A probability or likelihood that the number of sequence reads (now reduced) is attributable to chance is determined by comparison of a metric based upon the number of sequence reads to a threshold criterion. When the metric satisfies the threshold criterion, a structural variation is deemed to have occurred in (i) the different portion of the test nucleic acid that is represented by the first set of sequence reads and/or (ii) the different portion of the test nucleic acid that is represented by the second set of sequence reads. In some embodiments, this metric is defined in equation (1) above.

In some embodiments, a blackout list is maintained. The blackout list comprises a plurality of blackout regions of the test nucleic acid 602. In some such embodiments, the determining process 234 further comprises eliminating a sequence read 128 from the number of respective sequence reads when the first portion 130 of the sequence read overlaps a blackout region in the plurality of blackout regions (262). In some such embodiments, the determining process 234 further comprises eliminating a sequence read 128 from the number of respective sequence reads only when the first portion 130 of the sequence read is completely within a blackout region in the plurality of blackout regions.

In some embodiments, a white list is maintained. The white list comprises a plurality of regions of the test nucleic acid 602. In some such embodiments, the determining process 234 further comprises eliminating sequence reads 128 from the number of respective sequence reads when the first portion 130 of the sequence read does not overlap a white list region in the plurality of white list regions). In some such embodiments, the determining process 234 further comprises eliminating a sequence read 128 from the number of respective sequence reads only when the first portion 130 of the sequence read is completely outside all white list regions in the plurality of white list regions.

Part B. Additional Embodiment for Structural Variation.

Referring to FIG. 7, there is disclosed additional methods for detecting structural variation in sequencing data obtained from a single biological sample. Sequence reads are obtained, each comprising a portion corresponding to a subset of the test nucleic acid and a portion encoding an barcode that is independent of the sequencing data. Bin information is obtained. Each bin represents a different portion of the sample nucleic acid. Each bin corresponds to a set of sequence reads in a plurality of sets of sequence reads formed from the obtained sequence reads such that each sequence read in a respective set of sequence reads corresponds to a subset of the test nucleic acid represented by the bin corresponding to the respective set. Binomial tests identify bin pairs having more sequence reads with the same barcode in common than expected by chance. Probabilistic models determine structural variation likelihood from the sequence reads of these bin pairs.

FIG. 7 is a flow chart illustrating a method of determining a likelihood of a structural variation occurring in a test nucleic acid obtained from a single biological sample (702). In some embodiments, the method takes place at a computer system having one or more processors, and memory storing one or more programs for execution by the one or more processors in accordance with some embodiments (704).

Obtaining a Plurality of Sequence Reads.

In accordance with the disclosed systems and methods, a plurality of sequence reads 128 is obtained (706). Methods for obtaining sequence reads are disclosed in FIG. 7 at elements 706 through 720. Furthermore, any of the methods of obtaining sequence reads disclosed in Part A, Structural Variations, (e.g., elements 206 through 220 of FIG. 2) as described above may be used and for brevity are not repeated here.

Obtaining Bin Information.

In accordance with the disclosed systems and methods, a plurality of bins 140 is obtained (722). Methods for obtaining bins are disclosed in FIG. 7 at elements 722 through 730. Furthermore, any of the methods of obtaining binds disclosed in Part A, Structural Variations, (e.g., elements 222 through 230 of FIG. 2) as described above may be used and for brevity are not repeated here.

In some embodiments, to call large-scale structural variants, the test nucleic acid (e.g., the genome) is binned into 10 kb windows (hereinafter referred to as bins 140) and the unique barcodes 132 of Q60 reads within each bin 140 is counted. In some embodiments, to call large-scale structural variants, the test nucleic acid (e.g., the genome) is binned into bins 140 of a predetermined size (e.g., 5 kb, 1.0 kb, 20 kb, 40 kb and the unique barcodes 132 of Q40 reads, Q50 reads, Q60 reads or Q70 reads within each bin 140 are counted.

In some embodiments, each respective bin 140 in the plurality of bins represents a different portion of the test nucleic acid 602. The bin information identifies, for each respective bin in the plurality of bins, a set of sequence reads 128 in a plurality of sets of sequence reads, FIG. 5 illustrates. In FIG. 5, a test nucleic acid 602 is depicted. Further shown in FIG. 5, each respective bin 140 in a plurality of bins represents a different portion 142 of the test nucleic acid 602. Further, the bin information identifies, for each respective bin 140 in the plurality of bins, a set 144 of sequence reads 128 corresponding to the respective bin.

Continuing to refer to FIG. 5, each sequence read 128 in each set 144 of sequence reads in the plurality of sets of sequence reads is in the plurality of sequence reads. That is, each sequence read 128 corresponds to a portion 142 of the test nucleic acid 602 that has been binned.

Each respective sequence read in each respective set 144 of sequence reads in the plurality of sets of sequence reads has a respective first portion 130 that corresponds to a subset of the test nucleic acid that at least partially overlaps the different portion of the test nucleic acid that is represented by the bin corresponding to the respective set of sequence reads (722). For example, referring to set 144-1 illustrated in FIG. 5, each sequence read 128-1-1, . . . , 128-1-K, includes a first portion 130 that corresponds to at least a subset of the region 142-1 of the test nucleic acid 140-1 corresponding to bin 140-1. It will be appreciated from the schema and constructs of FIG. 3, that in typical embodiments, the first portions 130 of sequence reads 128-1-1, . . . , 128-1-K of set 144-1 are of different lengths and are displaced, yet overlapping, with respect to each other. In some embodiments, such first portions 130 may include some nucleotide positions from adjacent regions 142 of the test nucleic acid 602.

In some embodiments the first portions 130 only represent a subset of the region 142 of the test nucleic acid 602 of the bin 140.

In some embodiments, the region 142 of the test nucleic acid corresponding to a bin 140—is substantially longer than any given first portion 130 in the set 144 of sequence reads 128 within the bin. Moreover, in some embodiments, a given set 144 of sequence reads 128 includes five or more different barcode sequences 132, ten or more different barcode sequences 132, fifteen or more different barcode sequences 132, twenty or more different barcode sequences 132, twenty-five or more different barcode sequences 132, thirty or more different barcode sequences 132, thirty-five or more different barcode sequences 132, forty or more different barcode sequences 132, forty-five or more different barcode sequences 132, or fifty or more different barcode sequences 132.

In some embodiments, two or more, three or more, four or more, five or more, six or more, seven or more, eight or more, nine or more, ten or more, or eleven or more sequence reads 128 in a bin 144 have the same barcode sequences 132. In some embodiments, each sequence read 128 in a bin 144 has a different barcode sequence 132.

In some embodiments, each bin 140 in the plurality of bins represents at least 20 kbp, at least 50 kbp, at least 100 kbp, at least 250 kbp, or at least 500 kbp of the test nucleic acid (724). In other words, referring to FIG. 5, in some embodiments, the portion 142-1 of test nucleic acid 602 represented by bin 140-1 is at least 20 kbp, at least 50 kbp, at least 100 kbp, at least 250 kbp, or at least 500 kbp.

In some embodiments, there is no overlap between each different portion of the test nucleic acid represented by each respective bin in the plurality of bins (726). Such an embodiment is illustrated in FIG. 5. In such embodiments it is possible for overlap in the first portions 130 of the sequence reads 128, in the corresponding bin 144, with neighboring regions 142. In some embodiments, there is no overlap between each different portion 406 of the test nucleic acid represented by each respective bin in the plurality of bins (726), but there is some overlap in the first portions 130 of the sequence reads 128 in the corresponding bin 144 with neighboring portions 406.

In some embodiments, each respective sequence read in each respective set of sequence reads in the plurality of sequence reads has a respective first portion 130 that corresponds to a subset of the test nucleic 602 acid that fully overlaps the different portion of the test nucleic acid that is represented by the bin corresponding to the respective set of sequence reads (728). In other words, using bin 144-1 of FIG. 5 as an example, in some embodiments, each first portion 130 of each sequence read 128-1-1, . . . 128-1-k, includes a full copy of regions 142-1.

In some embodiments, the plurality of bins comprises 20 or more bins, 100 or more bins, 1000 or more bins, 10,000 or more binds, 100,000 or more bins or 1,000,000 or more bins (730).

Identify Bins that have Common Barcodes.

In the disclosed systems and methods, there is identified, from among the plurality of bins 140, a first bin and a second bin that correspond to portions of the test nucleic acid that are nonoverlapping. The first bin is represented by a first set of sequence reads 144 in the plurality of sequence reads and the second bin is represented by a second set of sequence reads 144 in the plurality of sequence reads (732). In some embodiments, each such set of sequence reads 144 comprises 10 or more sequence reads 128, 20 or more sequence reads 128, 30 or more sequence reads 128, or 100 or more sequence reads 128.

In some embodiments, the first bin (140) and the second bin (140) are at least a predetermined number of kilobases apart on the test nucleic acid (734). In some embodiments, the first bin and the second bin are at least 5 kilobases, at least 25 kilobases, at least 50 kilobases, at least 50 kilobases, or at least 100 kilobases apart on the test nucleic acid (736).

In some embodiments, a first value that represents a numeric probability or likelihood that the number of barcodes 132 common to the first set 144 and the second set 144 is attributable to chance is computed (738). In some embodiments, a binomial test to compute the first value (740). For instance, in some embodiments a binomial test is used to find all pairs of bins that are at least a predetermined distance (e.g., 50 kb or on different chromosomes) apart and share more barcodes 132 than what would be expected by chance (e.g., using a p-value cutoff of $10^{-15}$ without any multiple hypothesis correction). Advantageously, it has been discovered that such a cutoff is loose enough to include all interesting regions of potential structural variation. In some embodiments, the binomial test has the form:

$$p=1-P_{Binom}(n;n_1n_2/B)$$

where, p is the first value, expressed as a p-value, n is the number of unique barcodes that is found in both in the first and second set of sequence reads, $n_1$ is the number of unique barcodes in the first set of sequence reads, $n_2$ is the number of unique barcodes in the second set of sequence reads, and B is the total number of unique barcodes across the plurality of bins (742). In some embodiments, the single biological sample is human, the test nucleic acid 602 is the genome of the biological sample, and the first value satisfies the predetermined cut-off value when the first value is $10^{-12}$ or less, when the first value is $10^{-13}$ or less, when the first value is $10^{-14}$ or less, or when the first value is $10^{-15}$ or less (746).

In some embodiments, the number of pairs of bins that are compared here is roughly in the order of $10^{10}$. In order to perform these comparisons efficiently, in some embodiments the set of barcodes 132 in each bin 140 is coded as non-zero entries in a (very sparse) matrix and sparse matrix multiplications are used to identify regions that overlap (748). This allows for the quick identification of candidate bins 140 for further structural variation study. However, the disclosed binomial tests generate a very large number of false positives in some instances since it does not account for many aspects of the system, such as the length distribution of the test nucleic acid fragments 306 and the variation in the amplification rate across GEMs. In some embodiments, an identity of the first and second bin is determined using sparse matrix multiplication of the form:

$$V=A_1^TA_2,$$

where $A_1$ is a first $B \times N_1$ matrix of barcodes that includes the first bin, $A_2$ is a second $B \times N_2$ matrix of barcodes that includes the second bin, B is the number of unique barcodes across the plurality of bins, $N_1$ is the number of bins in $A_1$, $N_2$ is the number of bins in $A_2$, and is the transpose of matrix $A_1$ (750). In some embodiments, the first bin is associated with a first chromosome of the biological sample, the second bin is associated with a second chromosome of the biological sample, $N_1$ is the number of bins associated with the first chromosome, and $N_2$ is the number of bins associated with the second chromosome (752). In some embodiments, the first bin and the second bin are each associated with a first chromosome of the biological sample, $N_1$ is the number of bins associated with the first chromosome, and $N_2$ equals $N_1$ (754).

In a second pass, a probabilistic approach is used to clean up the initial candidate list of bins 140 (744). In some embodiments, an estimate of the set of library molecules is obtained by joining nearby sequence reads 128 (e.g. closer than 30 kb) having the same barcode 132. In the following discussion, the term "fragment" is used to refer to a span of nearby sequence reads 128 with the same barcode 132. Fragments originate from some unobserved molecules (that may be longer than the observed fragments). Based on the set of fragments, quantities such as read generation rate (sequenced reads per bp) of individual GEMs, the number of molecules inside each partition 304, and the molecule length distribution are estimated.

Given a pair of candidate bins $W_1$, $W_2$, the sets of fragments that overlap them are identified and then pairs of fragments in bins $W_1$ and $W_2$ with the same barcode 132 are identified. Such pairs of bins are potentially evidence for structural variation, since they suggest that the same molecule might have spanned two relatively distant loci of the genome. Accordingly, in some embodiments, responsive to a determination that the first value (described above) satisfies a predetermined cut-off value, for each barcode that is common to a first bin and a second bin 140, there is obtain a fragment pair thereby obtaining one or more fragment pairs. Each fragment pair in the one or more fragment pairs (i) corresponds to a different barcode that is common to the first bin and the second bin and (ii) consists of a different first calculated fragment and a different second calculated fragment. In some embodiments the one or more fragment pairs is a single fragment pair. In some embodiments the one or more fragment pairs is 2 or more fragment pairs, 5 or more fragment pairs, 10 or more fragment pairs or 100 or more fragment pairs.

For each respective fragment pair in the one or more fragment pairs the different first calculated fragment consists of a respective first subset of sequence reads 128 in the plurality of sequence reads having the barcode corresponding to the respective fragment pair. Each sequence read 128 in the respective first subset of sequence reads is within a predefined genetic distance (e.g., 30 kb) of another sequence read 128 in the respective first subset of sequence reads. The different first calculated fragment of the respective fragment pair originates with a first sequence read having the barcode corresponding to the respective fragment pair in the first bin. Each sequence read in the respective first subset of sequence reads is from the first bin. The different second calculated fragment consists of a respective second subset of sequence reads in the plurality of sequence reads having the barcode corresponding to the respective fragment pair. Each sequence read in the respective second subset of sequence reads is within a predefined genetic distance (e.g., 30 kb) of another sequence read in the respective second subset of sequence reads. The different second calculated fragment of the respective fragment pair originates with a second sequence read having the barcode corresponding to the respective fragment pair in the second bin, and each sequence read in the respective second subset of sequence reads is from the second bin (744).

To quantify the above identified evidence that a pair of bins exhibit structural variation a likelihood ratio score is computed in some embodiments (756). In some embodiments, a respective likelihood is computed based upon a probability of occurrence of a first model and a probability of occurrence of a second model regarding the one or more fragment pairs to thereby provide a likelihood of a structural variation in the test nucleic acid 602. The first model specifies that the respective first calculated fragments and the respective second calculated fragments of the one or more fragment pairs are observed given no structural variation in the target nucleic acid sequence and are part of a common molecule. The second model specifies that the respective first calculated fragments and the respective second calculated fragments of the one or more fragment pairs are observed given structural variation in the target nucleic acid sequence (756).

In some embodiments, the computed likelihood is computed as a ratio score between the probability of occurrence of the first model and the probability of occurrence of the second model (758). Referring to element 760 of FIG. 7F, in some embodiments, the computed likelihood is computed as:

$$LR = \frac{P(\text{observed fragments} \mid SV)}{P(\text{observed fragments} \mid \text{no } SV)}$$

Since fragments with different barcodes are independent, this score decomposes to a product of terms with one term for each of the pairs of fragments with the same barcode b:

$$\frac{P(r_1, r_2, l_1, l_2 d \mid SV; a_b)}{P(r_1, r_2, l_1, l_2, d \mid \text{no } SV; a_b)} \quad (1)$$

where:

$r_1, r_2$ are the number of sequence reads (128) on each of the two fragments, $l_1, l_2$ are the observed lengths of the two fragments, d is the distance between the two fragments, and $a_b$ is the rate (reads/bp) of the GEM/barcode b.

In other words, LR is equal to a product of one or more terms (e.g., a plurality of terms), where each respective term (i) represents a respective fragment pair in the one or more fragment pairs and (ii) has the form:

$$\frac{P(r_1, r_2, l_1, l_2, d \mid SV; a_b)}{P(r_1, r_2, l_1, l_2, d \mid \text{no } SV; a_b)}$$

where $r_1$ is a number of sequence reads in the respective first subset of sequence reads in the first calculated fragment for the respective fragment pair, $l_1$ is a length of the first calculated fragment as determined by the first subset of sequence reads of the respective fragment pair, $r_2$ is a number of reads in the respective second subset of sequence reads in the second calculated fragment for the respective fragment pair, $l_2$ is a length of the second calculated fragment as determined by the second subset of sequence reads of the respective fragment pair, d is a distance between the first calculated fragment and the second calculated fragment of the respective fragment pair in the test nucleic acid, $a_b$ is a read rate of the first barcode across the plurality of sequence reads, SV indicates the first calculated fragment and the second calculated fragment are observed in accordance with the first model, and no SV indicates the first calculated fragment and the second calculated fragment are observed in accordance with the second model (760).

Figure 7A:
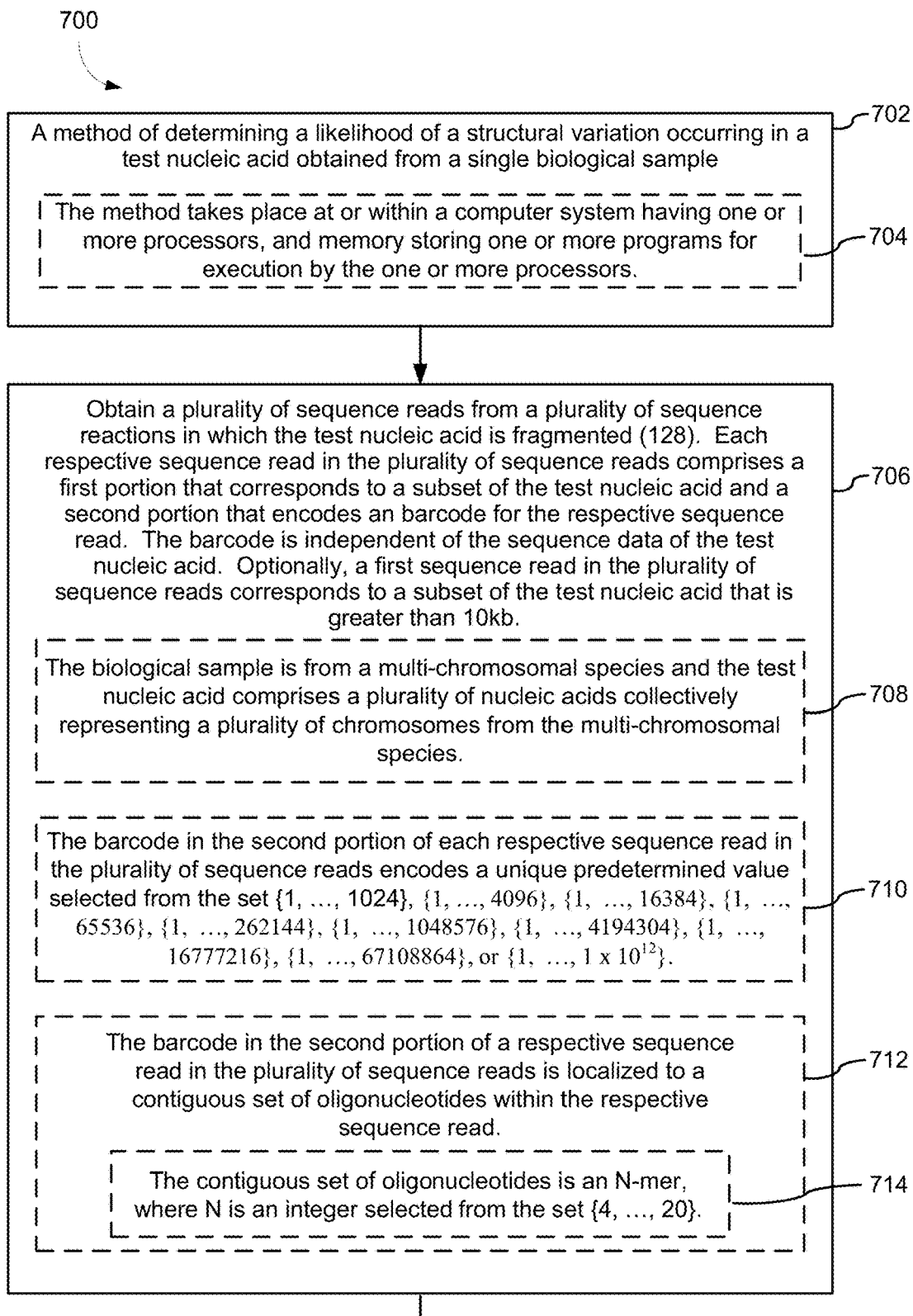
Figure 7B:
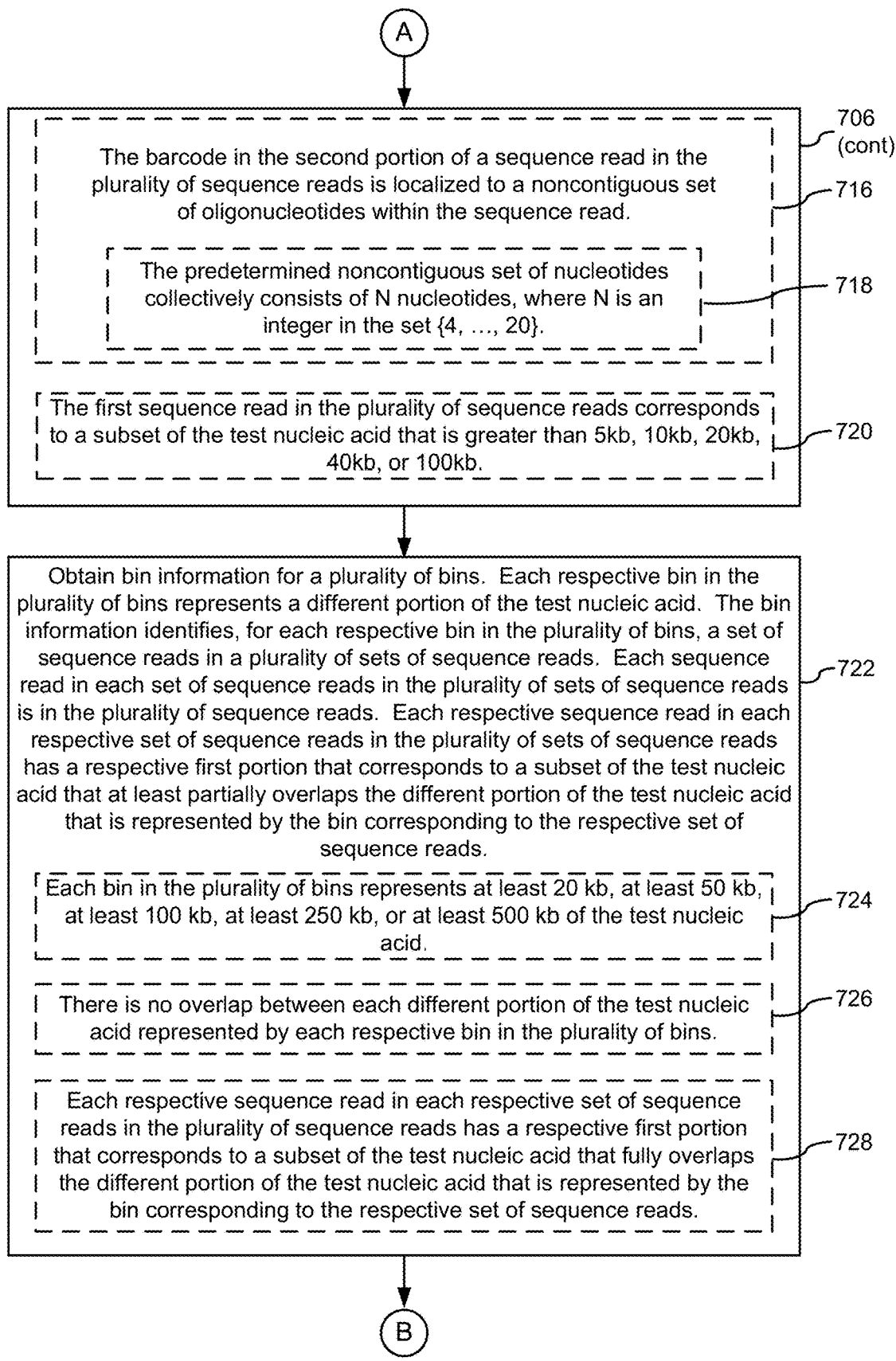
Figure 7C:
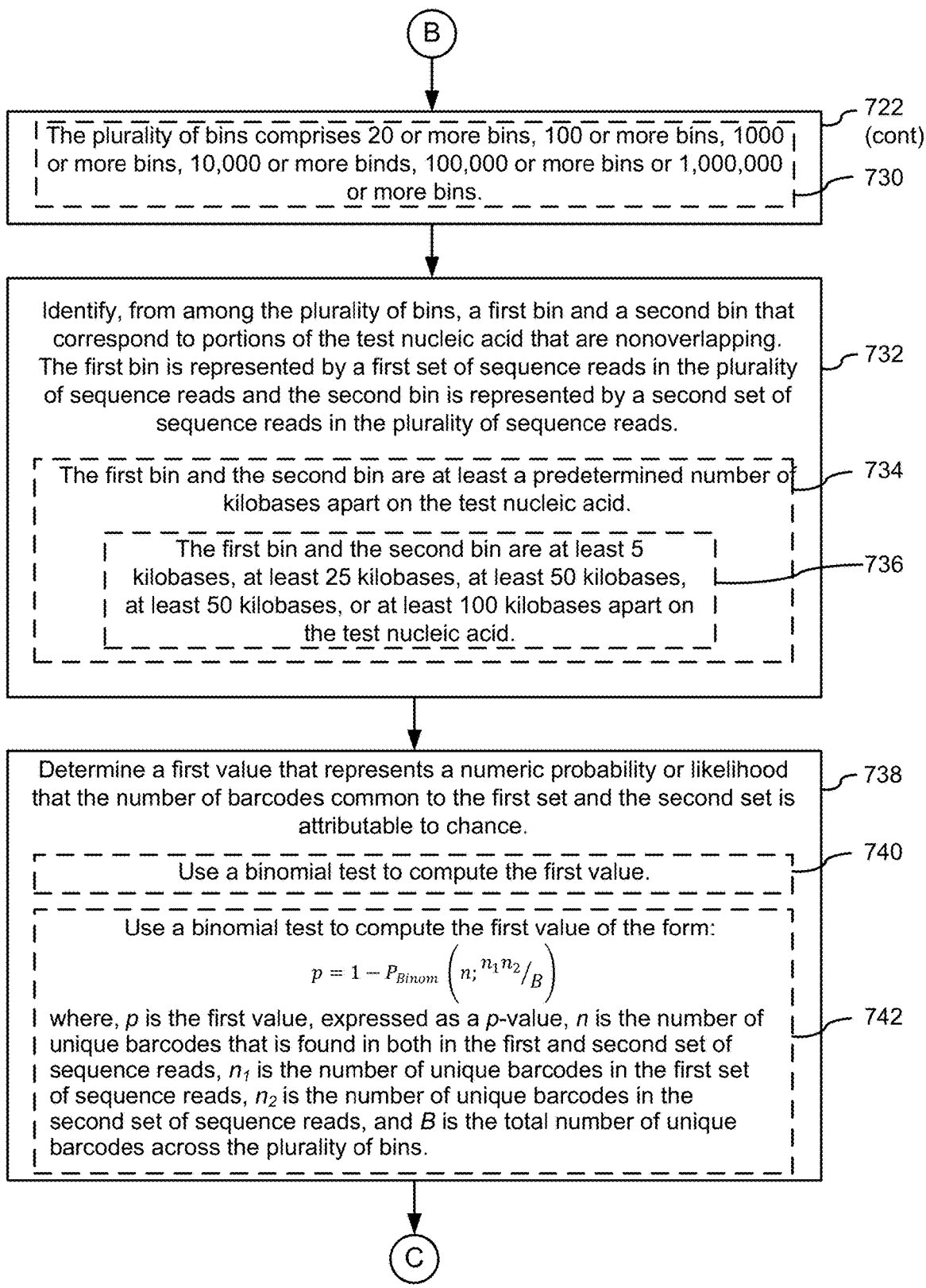
Figure 7E:
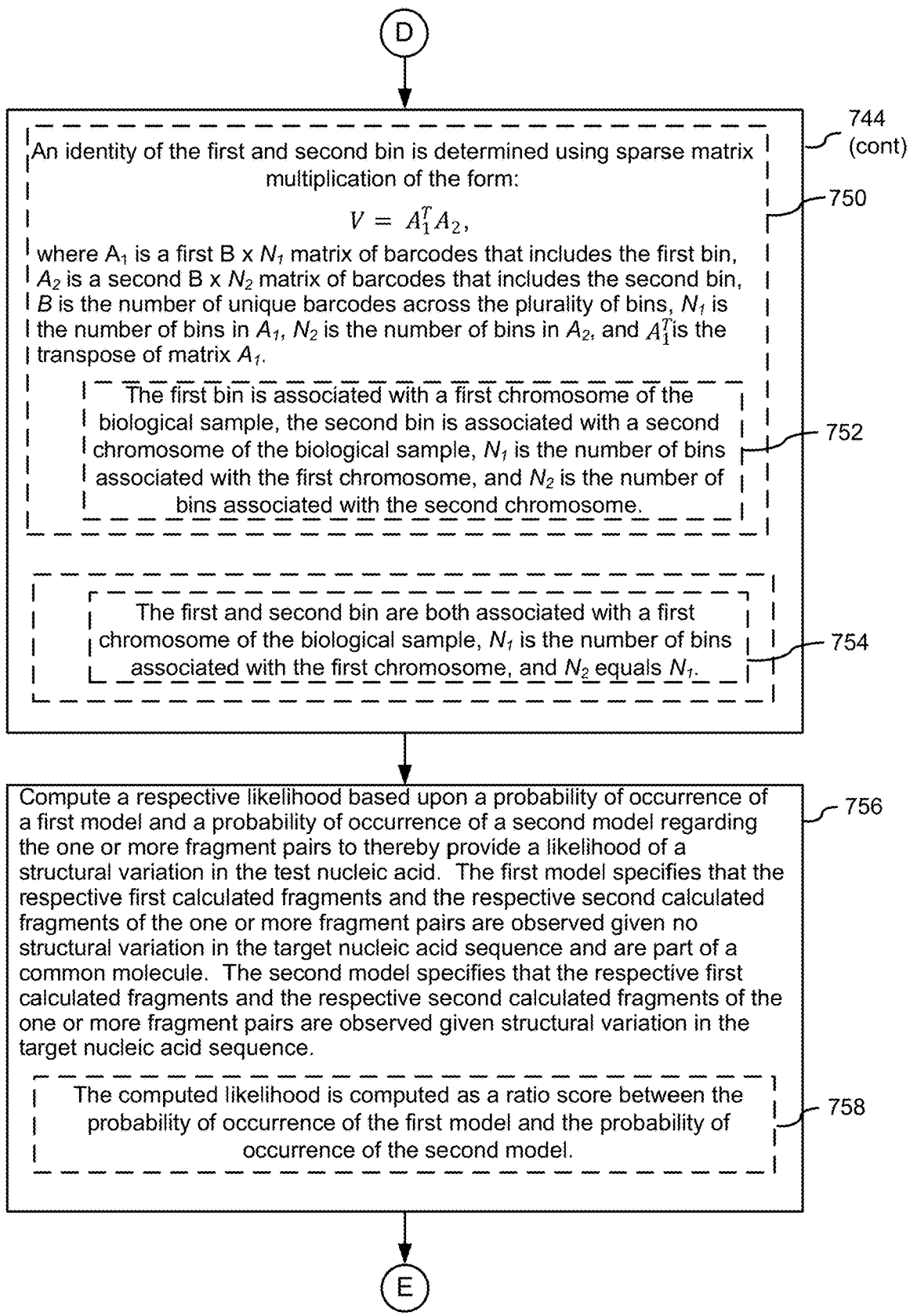
Figure 7F:
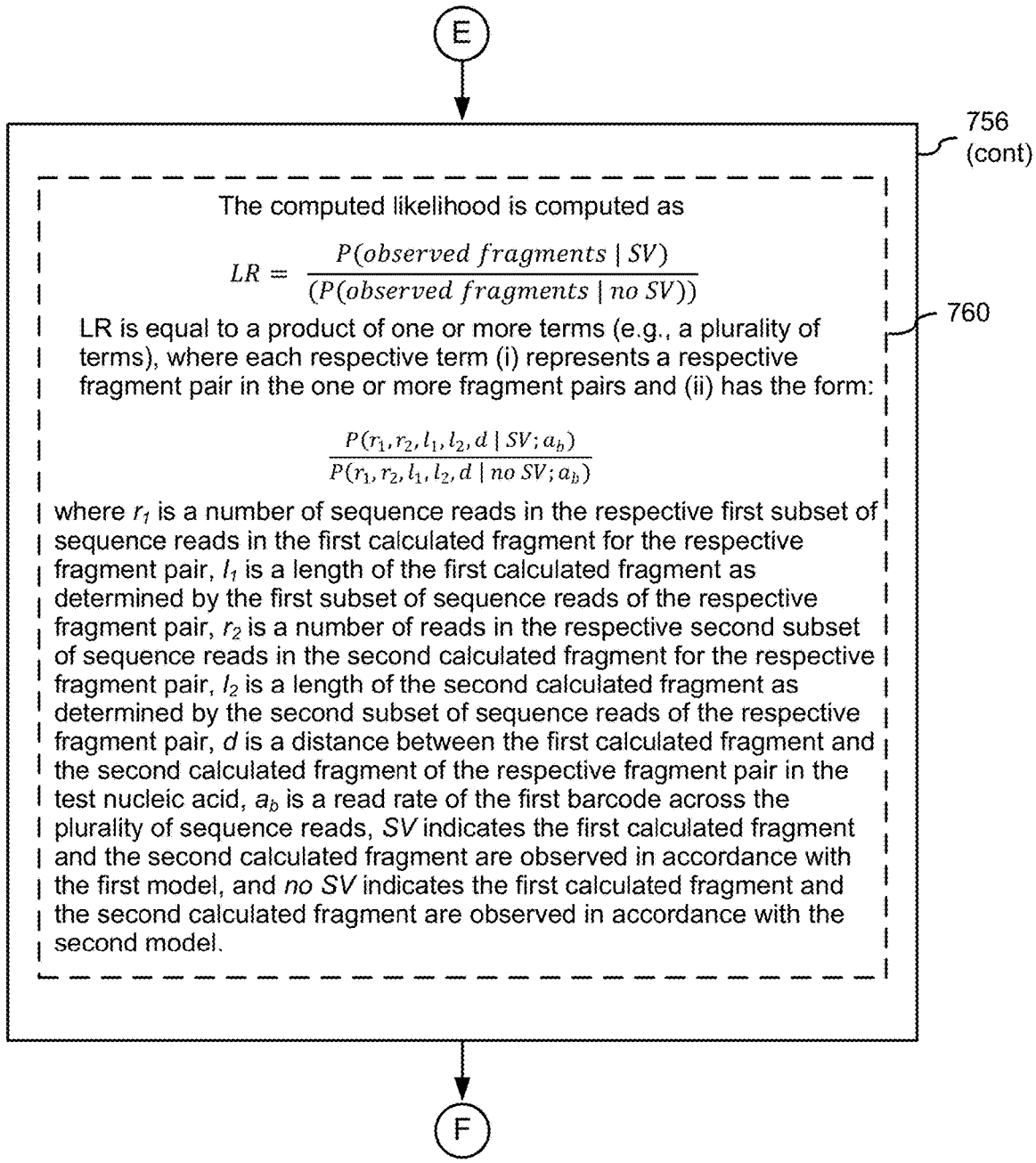

Referring to element 762 of FIG. 7G, in some embodiments, the two candidate fragments might have originated from the same molecule or from different molecules, therefore:

$P(r_1,r_2,l_1,l_2,d \mid \text{no } SV; a_b) = P(r_1,r_2,l_1,l_2,d \mid \text{same molecule, no } SV; a_b)P(\text{same molecule} \mid \text{no } SV) + P(r_1,r_2,l_1,l_2,d \mid \text{different molecules, no } SV; a_b) P(\text{different molecules} \mid \text{no } SV)$ (2)

The probability given that the fragments originated from different molecules is:

$P(r_1,r_2,l_1,l_2,d \mid \text{different molecules, no } SV; a_b) = P_{frag}(r_1, l_1; a_b) P_{frag}(r_2, l_2; a_b)$ where $P_{frag}(r,l;a_b)$ is the probability of observing r sequence reads 128 from a molecule of unknown length such that the reads span an observed length of l. Referring to element 764 of FIG. 7G, assuming that the sequence reads 128 are generated from a Poisson process with constant rate across the genome, we get:

$$P_{frag}(r, l; a_b) = \sum_{m: m \geq l} \left( r(r-1)\left(\frac{l}{m}\right)^{r-2} \frac{m-l}{m^2} \right) P_p(r; ma_b) P_L(m) =$$

$$\sum_{m: m \geq l} (m-l) P_p(r-2; a_b l) P_p(0; a_b(m-l)) a_b^2 P_L(m)$$

where $P_p(r;b)$ is the probability mass function of a Poisson distribution with parameter b and $P_L(m)$ is the (pre-estimated) probability that the true molecule length is m.

Referring to element 766 of FIG. 7G, the probability given that the fragments came from the same molecule can be computed in a similar way as:

$$\sum_{m: m \geq l_1 + l_2 + d}^{P(r_1,r_2,l_1,l_2,d \mid \text{same molecule, no } SV; a_b)} = (m - l_1 - l_2 - d)$$

$$P_p(r_1 - 2; a_b l_1) P_p(r_2 - 2; a_b l_2) P_p(0; a_b(m - l_1 - l_2)) a_b^4 P_L(m)$$

where m is length of the true molecule length, $P_p(r_1-2;a_b l_1)$ is a probability mass function of a Poisson distribution with parameter b for $r_1$, $P_p(r_2-2;a_b l_e)$ and $r_2$, $P_p(0;a_b(m-l_1-l_2))$ are each probability mass functions of a Poisson distribution with parameter b, and $P_L(m)$ is a pre-estimated probability that the true common molecule length is m.

In the presence of a structural variation, the likelihood is similar to equation (2). However, in this case, there is an additional unknown, namely the exact position of the breakpoints with respect to the observed fragments. For example, assume that there was a deletion between positions 100,000 and 200,000 of chr1 and that the observed fragments span the regions 85,000-90,000 and 210,000-230,000. If the exact breakpoints were known, the previous calculations could be used with d set to 10 kb+10 kb=20 kb. Since the position of the true breakpoints (and therefore the true distance between the observed fragments) is unknown, it is integrate out in some embodiment. Rather, in some embodiments, to simplify calculations, a rough estimate of d is obtained by computing the maximum extent d' such that $P_p(0;a_b d') \geq 0.75$. Then, d is set to 2d' in the equations above in order to compute $P(r_1,r_2,l_1,l_2,d \mid SV;a_b)$. In other words, in some embodiments $P(r_1,r_2,l_1,l_2,d \mid SV;a_b) = P(r_1,r_2,l_1,l_2,2d' \mid SM, \text{no } SV;a_b) P(SM \mid \text{no } SV) + P(r_1,r_2,l_1,l_2,2d' \mid DM, \text{no } SV;a_b) P(DM \mid \text{no } SV),$ where SM is the hypothesis that the first calculated molecule and the second calculated molecule originated from the same fragment of the test nucleic acid in the plurality of sequencing reactions, DM is the hypothesis that the first calculated molecule and the second calculated molecule originated from different fragments of the test nucleic acid in the plurality of sequencing reactions, $$P(r_1,r_2,l_1,l_2,2d'|DM,SV;a_b)=P_{frag}(r_1,l_1;a_b)P_{frag}(r_2,l_2;a_b), \text{ wherein}$$

$P_{frag}(r_1,l_1;a_b)$ is the probability of observing $r_1$ reads from a first molecule of unknown length such that the reads span an observed length of $l_1$, $P_{frag}(r_2,l_2;a_b)$ is the probability of observing $r_2$ reads from a second molecule of unknown length such that the reads span an observed length of $l_2$, and 2d'=is a distance between the first calculated fragment and the second calculated fragment of the respective fragment pair in the test nucleic acid taking into account an estimate of the breakpoints of a structural variation associated with the first calculated molecule and the second calculated molecule. Here $P_{frag}(r_1,l_1,a_b)$ and $P_{frag}(r_2,l_2,a_b)$ are each computed as $$\sum_{m:m\geq l}\left(r(r-1)\left(\frac{l}{m}\right)^{r-2}\frac{m-l}{m^2}\right)P_p(r;ma_b)P_L(m) = \sum_{m:m\geq l}(m-l)P_p(r-2;a_bl)P_p(0;a_b(m-l))a_b^2P_L(m)$$

where, $P_p(r;b)$ is the probability mass function of a Poisson distribution with parameter b, and $P_L(m)$ is the (pre-estimated) probability that the true molecule length of the respective molecule is m. Further, $P(r_1,r_2,l_1,l_2,2d'|SM,SV;a_b)$ is computed as $$\sum_{m:m\geq l_1+l_2+d}(m-l_1-l_2-2d')P_p(r_1-2;a_bl_1)P_p(r_2-2;a_bl_2)P_p(0;a_b(m-l_1-l_2))a_b^4P_L(m)$$

where m is the length of the true molecule length, $P_p(r_1-2;a_bl_1)$ is a probability mass function of a Poisson distribution with parameter b for $r_1$, $P_p(r_2-2;a_bl_2)$ is a probability mass function of a Poisson distribution with parameter b for $r_2$, $P_p(0;a_b(m-l_1-l_2))$ is a probability mass function of a Poisson distribution with parameter b, and $P_L(m)$ is a pre-estimated probability that the true common molecule length is m.

In some embodiments, to get the priors in equation (2) above, it is assumed that the probability of having a second molecule at any given position of the genome is M/G where M is the total number of input molecules and G is the size of the genome. These priors are actually independent of whether there is a structural variation or not so P(same molecule j no SV)=P(same molecule) and P(different molecules)=1−P(same molecule).

The above discussion for equations (1) and (2) assumes whole-genome sequencing data. In the case of targeted sequencing, the composition of the target set is taken into consideration. In some embodiments, the assumption is made that the off-target regions generate reads following a similar Poisson process as the target regions, but with a different rate. In particular, let $b_t$ be the fraction of reads on target and $g_t$ be the fraction of the genome that is covered by the target regions. If $a_b$ the Poisson rate of target regions, then the rate of off-target regions is:

$$\tilde{a}_b = \frac{1-b_t}{1-g_t}\frac{g_t}{b_t}a_b$$

The probability of observing r reads from a region that contains $l_t$ by of targets and $l_n$ by of off-target regions is:

$$P_{mixture}(r, l_1, l_2; a_b, \tilde{a}_b) = \sum_{n=0}^{n=r} P_p(r-n; a_bl_t)P_p(n; \tilde{a}_bl_n)$$

The probability of observing r reads from a molecule of unknown length that spanned an observed length of $l=l_t+l_r$, is:

$$\sum_{m:m\geq l} P_{mixture}(r-2, l_t, l_n; a_b, \tilde{a}_b)a_b^2P_L(m)\sum_{f\in\text{offsets}} P_{mixture}(0, d_{f_t}, d_{f_n}; a_b, \tilde{a}_b)$$

where the inner sum is taken over all m−l offsets of the unobserved molecule with respect to the observed fragment, and $d_{f_t}$ and $d_{f_n}$ are the bases on and off-target for the corresponding offset. To simplify calculations, for a given value of m, the average fraction of bases on and off-target is computed across all offsets and the assumption is made that all offsets have the same target composition in some embodiments. The rest of the probabilities needed to compute (1) are adjusted in a similar way from the WGS case.

In some embodiments, all probabilities were computed in log-space to avoid underflows. In some embodiments, a log-likelihood ratio cutoff of 200 is used. This cutout has been empirically found to result in high-quality calls with very low false positive rates (after the filtering steps described below).

In some embodiments, the structural variation is an insertion or deletion of 50 consecutive bases or more, 500 consecutive bases or more, or 5000 consecutive bases or more, into the different portion of the test nucleic acid that is represented by the first set of sequence reads (768). In some embodiments, the different portion of the test nucleic acid of the first bin overlaps the different portion of the test nucleic acid represented by the second bin (770). In some embodiments, at least 50, 80 percent, or 95 percent of the different portion of the test nucleic acid of the first bin overlaps the different portion of the test nucleic acid of the second bin (772). In some embodiments, the structural variation is a translocation of 50 consecutive bases or more into the different portion of the test nucleic acid that is represented by the first set of sequence reads from the different portion of the test nucleic acid that is represented by the second set of sequence reads (774).

In some embodiments, the different portion of the test nucleic acid represented by the bin corresponding to the first set of sequence reads is from a first chromosome of the biological sample, and the different portion of the test nucleic acid represented by the bin corresponding to the second set of sequence reads is from a second chromosome of the biological sample, where the second chromosome is other than the first chromosome (776). In some embodiments, the first chromosome is a paternal chromosome and the second chromosome is a maternal chromosome (778). In some embodiments, the biological sample is human and the first chromosome is any of chromosome 1-21 (780).

In some embodiments, the structural variation is deemed to have occurred, and the method further comprises treating a subject that originated the biological sample with a treatment regimen responsive to the structural variation (782). In some embodiments, the treatment regimen comprises a diet modification (784). In some embodiments, the treatment regimen comprises application of a pharmaceutical composition that inhibits a biological pathway associated with the structural variation (786).

Refining Breakpoints Using Short Read Information.

In some embodiments, after obtaining breakpoint windows using the approach described above, this information from read pairs and split reads is used to further refine the breakpoint locations. For each called structural variant, all read pairs and split reads within the called breakpoint bins are selected. Then a probabilistic approach similar to Layer et al, 2014, "LUMPY: A probabilistic framework for structural variant discovery," *Genome Biology*, 15(6), R84, doi: 10.1186/gb-2014-15-6-r84, which his hereby incorporated by reference herein in its entirety, is used to infer the breakpoint loci based on the combined evidence from all selected read pairs and split reads. In order to avoid false positives, inference of the exact breakpoint loci was only attempted when there were at least four read pairs and split reads supporting the call.

Filtering Calls Based on Gaps and Segmental Duplications.

In some embodiments, a blackout list is maintained (788), the blackout list comprising a plurality of blackout regions of the test nucleic acid, and the method further comprises eliminating a sequence read, prior to the identifying, from the number of respective sequence reads when the first portion of the sequence read overlaps a blackout region in the plurality of blackout regions (788). For instance, in some embodiments, structural variant calls whose breakpoints overlap different copies of the same segmental duplication (using the Segmental Duplication track from the UCSC browser) were excluded. Structural variation is enriched in such regions (Mills et al., 2011, "Mapping copy number variation by population-scale genome sequencing," *Nature*, 470(7332), 59-65, doi:10.1038/nature09708, which is hereby incorporated by reference in its entirety), so some of these calls might represent true events. However, a large fraction of calls in regions of structural variation have been observed to be the result of the inability of aligners to properly resolve repetitive regions, since a small amount of variation is sufficient to make reads map uniquely and with high mapping quality to one or the other copy of the segmental duplication. Structural variant calls within a pre-determined distance (e.g. 10 kb) from gaps (using the gaps track from the UCSC browser) or from new sequence introduced in hg38 (using the hg19 diff track from the UCSC browser) were also excluded. The rationale was that such calls are not interesting since they probably represent misassemblies in hg19.

Part C. Phasing.

Figure 11:
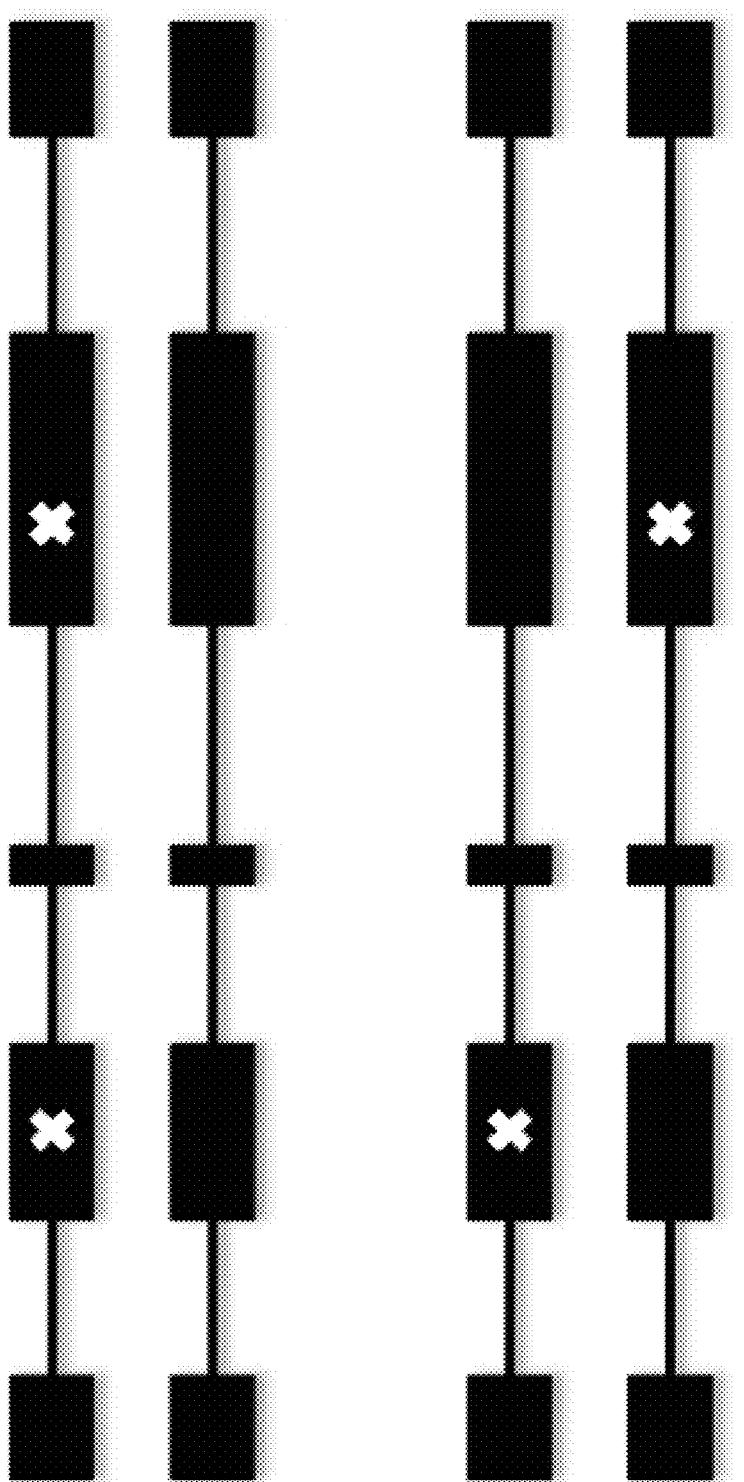
FIG. 11 illustrates cis versus trans mutations in accordance with the prior art.

In this section, exemplary methods implemented by some embodiments of phasing sub-module 124 are disclosed. Motivation for phasing the sequence reads 128 into parental haplotypes is illustrated. Phased variants are a more complete representation of the state of a diploid genome. A variety of research has found that phased variants allow for a better understanding of observed phenotypes. See, for example, Tewhey et al., 2011, "The importance of phase information for human genomics," Nat Rev Genet, 12:215-223, which is hereby incorporated by reference in its entirety. For example, in the presence of compound heterozygosity, phasing is required to disambiguate the loss of one or both copies of the gene. Referring to FIG. 11, for example, two loss of function mutations in cis leave a functional copy of the gene, whereas two loss of function mutations in trans leaves both copies inactivated. Thus, it is necessary to properly phase sequence reads in order to elucidate the state of a diploid genome.

Algorithm for phasing. In order to phase the variants (e.g., the variants called in Part A or Part B above), the likelihood of sequence read and barcode support for each allele given a phasing configuration is modeled. See, for example, Bansal et al., 2008, "An MCMC algorithm for haplotype assembly from whole-genome sequence data," Genome Res, 18:1336-1346, which is hereby incorporated by reference in its entirety. Then a search for the maximum likelihood phasing configuration is conducted. This algorithm first finds near-optimal local haplotype configurations with beam-search over blocks of adjacent variants. In some embodiments, the blocks of adjacent variants comprise about 40 variants. In some embodiments, the blocks of adjacent variants consist of between 10 and 30 variants, between 20 and 50 variants, between 30 and 60 variants, or more than 60 variants. Neighboring blocks are greedily joined to form a global solution, which is iteratively refined until convergence. The confidence of each phasing decision is the likelihood-ratio between optimal and next-best solutions.

In particular, a pre-determined set of variant calls is obtained (e.g., from parts A or part B above, a plurality of single nucleotide polymorphisms, from other sources, etc.). Alleles $A_{i,p}$ are labeled, where $i \in 1; \ldots, N$ indexes the variant. In some embodiments, $p \in 0, 1$ is an arbitrary label for the two alleles of the variant. The set of alleles that come from the same parent chromosome is referred to as a haplotype, and are arbitrarily labeled $H_0$ and $H_1$. The goal of the phasing algorithm is to determine which allele from each variant came from each parent chromosome. In some embodiments, the phasing result can be described by a binary variable for each variant $X_i \in 0, 1$ where $X_i = 0$ indicates the $A_{i,0} \in H_0$ and $A_{i,1} \in H_1$ and $X_i = 1$ indicates that $A_{i,0} \in H_1$ and $A_{i,1} \in H_0$.

In some alternative embodiments, $p \in \{0, 1, -1\}$ in which label "0" assigns a respective variant call in $A_{i,p}$ to $H_O$, label "1" assigns the respective variant call to $H_1$, and label "−1" provides the advantageous possibility of denoting an error condition in the assignment of the variant call to a haplotype. This error condition represents an error in the zygosity of the underlying variant. This alternative embodiment takes into consideration that standard variant calling algorithms that are relied upon to provide variant calls at positions $A_{i,p}$ between $H_O$ and $H_1$ may, in fact, call the zygosity of such positions incorrectly on occasion. The disclosed alternative phasing embodiment $p \in \{0, 1, -1\}$ advantageously allows for exploration of this form of zygosity error during the phasing. The ability to selectively sample for this error state advantageously protects the phasing algorithm from error in the input data that arises, for instance due to error in the sequencing process, weak sequencing signal, and the like.

Neighboring variants on the test nucleic acid sequence 602 (e.g. genome) are often separated by distances longer than the read-pair length (e.g., sequence read length 128), causing very short phase blocks. As disclosed above, long test nucleic acid fragments 306 (e.g. input fragments) covering a small fraction (0:01-0:001) of the test nucleic acid sequence 602 (e.g. genome) are exposed to each barcode 132, so the probability that a barcode 132 contains sequence reads 128 from both haplotypes is small.

In some embodiments, sequence reads 128 are aligned to the genome of the target organism. Sequence reads 128 are grouped by the attached barcode 132 sequences. Sequence reads 128 with common barcode sequences 132 are partitioned into groups that are likely to have originated from a single test nucleic acid fragment 306 (e.g. genomic input fragment), and thus provide evidence that the alleles covered by the sequence reads 128 came from the same haplotype. In some embodiments, the plurality of barcoded sequence reads is denoted $\vec{O}$. In some embodiments, each respective sequence read $\vec{O}_q$ in the plurality of sequence reads, where q is an integer index into $\vec{O}$, comprises a first portion that corresponds to a subset of the reference sequence and a second portion that encodes a respective barcode, independent of the reference sequence, for the respective sequence read, in a plurality of barcodes.

In some embodiments, each respective sequence read $\vec{O}_q$ in the plurality of sequence reads $\vec{O}$ is $\in \{0, 1, -\}^n$, where (i) each respective label "0" for the respective sequence read $\vec{O}_q$ assigns a corresponding variant call in $A_{i,p}$ to $H_0$, (ii) each respective label "1" for the respective sequence read $\vec{O}_q$ assigns a corresponding variant call in $A_{i,p}$ to $H_1$, and (iii) each respective label "-" for the respective sequence read $\vec{O}_q$ indicates that the corresponding variant call in $A_{i,p}$ is not covered. For example, consider the case in which $\vec{O}_q$ contains 5 of the 10 variant calls in $A_{i,p}$. In this example, $\vec{O}_q$ will contain five variant calls with values "-" because they are not in the respective sequence read and $\vec{O}_q$ will contain values for the five other variant calls in $A_{i,p}$. Each value in these five values will be a zero or a one depending on the haplotype assigned to the respective variant call in the sequence read. In some embodiments, such haplotype assignments are obtained for the variant calls in individual sequence reads using conventional haplotype assignment algorithms.

In some embodiments, to account for possible error in the zygosity of a variant call as described above, each respective sequence read $\vec{O}_q$ in the plurality of sequence reads $\vec{O}$ is $\in \{0, 1, -1, -\}^n$, where (i) each respective label "0" for the respective sequence read $\vec{O}_q$ assigns a corresponding variant call in $A_{i,p}$ to $H_0$, (ii) each respective label "1" for the respective sequence read $\vec{O}_q$ assigns a corresponding variant call in $A_{i,p}$ to $H_1$, (iii) each respective label "-1" for the respective sequence read $\vec{O}_q$ assigns a corresponding variant call in $A_{i,p}$ to the zygosity error condition (present, but neither $H_0$ nor $H_1$), and (iv) each respective label "-" for the respective sequence read $\vec{O}_q$ indicates that the corresponding variant call in $A_{i,p}$ is not covered.

In the disclosed methods, a phasing result $\vec{X}$ is obtained by optimization of haplotype assignments at individual positions i in $A_{i,p}$. In embodiments where each respective sequence read $\vec{O}_q$ in the plurality of sequence reads $\vec{O}$ is $\in \{0, 1, -\}^n$, these haplotype assignments are each between $H_0$ and $H_1$ at individual positions i for the plurality of sequence reads. In the alternative embodiments where possible error in the zygosity of the position i is to be additionally sampled in the phasing algorithm, each respective sequence read $\vec{O}_q$ in the plurality of sequence reads $\vec{O}$ is $\in \{0, 1, -1, -\}^n$, these haplotype assignments are each between $H_0$, $H_1$ and $H_{-1}$ at individual positions i for the plurality of sequence reads, where $H_{-1}$ denotes the zygosity error condition above.

Sequence reads are aligned to a reference genome. Furthermore, sequence reads that have the same barcode are grouped together. In this way, sequence reads with a common barcode are partitioned into groups that are likely to have originated from a single genomic input fragment f, and thus provide evidence that the alleles covered by the sequence read came from the same haplotype.

In some embodiments where each respective sequence read $\vec{O}_q$ in the plurality of sequence reads $\vec{O}$ is $\in \{0, 1, -\}^n$, the probability of the observed sequence reads 128 covering variant i from test nucleic acid fragment 306f is computed as:

$$\log P(O_{i,f} | A_{i,p}) = \sum_r 1(S_r = A_{i,p})(1 - 10^{-Q_r/10}) + 1(S_r \neq A_{i,p})(10^{-Q_r/10})$$

where r sums over the reads and $1(S_r = A_{i,p})$ is the indicator function testing whether the $r^{th}$ sequence read 128 $S_r$ matches allele $A_{i,p}$. When the $r^{th}$ sequence read 128 $S_r$ matches allele the indicator function has a first value (e.g., "1") and is a second value (e.g. "0") otherwise. The term $1(S_r \neq A_{i,p})$ is the indicator function that has a first value (e.g., "1") when the $r^{th}$ sequence read $S_r$ from fragment f does not match $A_{i,p}$ and is a second value (e.g., "0") otherwise. In some embodiments, the probability assigned is derived from the inverse-Phred transformed quality value of relevant read base $Q_r$.

In embodiments where each respective sequence read $\vec{O}_q$ in the plurality of sequence reads $\vec{O}$ is $\in \{0, 1, -1, -\}^n$, that is possible zygosity error at position i is additionally sampled, the probability of the observed sequence reads covering variant i from fragment f is computed as:

$$\log P(O_{i,f} | A_{i,p}) = $$
$$\sum_r 1(S_r = A_{i,p})(1 - 10^{-Q_r/10}) + 1(S_r \neq A_{i,p})(10^{-Q_r/10}) + 1(A_{i,p} = X^-)^{0.5}$$

where,
$X^-$ is $H_{-1}$, and
$1(A_{i,p}=X^-)$ is the indicator function that has a first value (e.g., "1") when $A_{i,p}$ is equal to -1 ($H_{-1}$) and is a second value (e.g., "0") otherwise.

In embodiments where $\vec{O}$ is $\in \{0, 1, -\}^n$, the phasing result can be obtained by optimizing an objective function expressed as a maximum likelihood phasing parity vector:

$$\hat{X} = \underset{\vec{X}}{\mathrm{argmax}}\, P(\vec{O} | \vec{X})$$

Here, $\hat{X}$ is the refined phasing vector while $\vec{X}$ is the phasing vector result to be inferred and $$P(\vec{O}|\vec{X}) = \Pi_f P(O_{1,f}, \ldots, O_{N,f}).$$

In embodiments where $\vec{O}$ is $\in \{0, 1, -1, -\}^n$, the phasing vector can be found by optimizing an overall objective function:

$$\hat{X} = \mathop{\mathrm{argmax}}_{\vec{X}} P(\vec{X} \mid \vec{O}) \bigg| = \frac{P(\vec{X})P(\vec{O} \mid \vec{X})}{C}$$

where, $$P(\vec{X}) = \prod_i \frac{(1-\varepsilon_i)}{2}(X_i = H_1) + (X_i = H_0) + \varepsilon_i(X_i = H_{-1}),$$

$H_{-1}$ is the condition of zygosity error at position i,
$\varepsilon_i$ is an estimate of incurring this form of error at position i, and $$P(\vec{O} \mid \vec{X}) = \prod_f P(O_{1,f}, \ldots, O_{N,f}).$$

In some embodiments, $\varepsilon_i$ is a function of the type of variant at position i. For instance $\varepsilon_i$ is given a first value if the variant at position i arises through genetic insertions or deletion, and another value if the variant at position i arises by other means (e.g., single nucleotide polymorphisms).

The data from a test nucleic acid fragment 306 $f$ come from one of three cases. The first two cases are that the alleles present are only from $H_0$ or only from $H_1$. These cases are the typical cases and have a high prior probability, governed by the fraction of the test nucleic acid fragment 306 (e.g., genome) present in each partition 304. The third case is that input DNA from both haplotypes was present at the locus, so either allele is equally likely to be observed:

$$P(O_{1,f}, \ldots, O_{N,f} \mid X, H_f = 0) = \Pi_i P(O_{i,f} \mid A_{i,X_i}),$$

$$P(O_{1,f}, \ldots, O_{N,f} \mid X, H_f = 1) = \Pi_i P(O_{i,f} \mid A_{i,1-X_i}),$$

$$P(O_{1,f}, \ldots, O_{N,f} \mid X, H_f = M) = \Pi_i 0.5$$

The above three equations give the probability of the observed sequence reads 128 from fragment 306$f$ at variant location i, $X_i$, and fragment haplotype $H_f$. Observations are independent given the variant party and fragment haplotype. The prior probability of the third case is $\propto$—the probability that a partition contains both haplotypes at a locus. The overall likelihood can be computed by summing over the three cases:

$$P(O_{i,f} \mid X_i) =$$
$$\frac{(1-\propto)}{2}(P(O_{i,f} \mid X_i, H_f = 0) + P(O_{i,f} \mid X_i, H_f = 1)) + \propto P(O_{i,f} \mid H_f = M)$$

$$P(O_{i,f}, \ldots, O_{N,f} \mid X) =$$
$$\frac{(1-\propto)}{2}\left(\prod_i P(O_{i,f} \mid A_i, X_i) + \prod_i P(O_{i,f} \mid A_i, 1 - X_i)\right) + \propto \prod_i 0.5$$

Each position in the test nucleic acid 602 (e.g., genome) with a heterozygous variant is given a variant index $v \in 1, \ldots, N$, and each of the two alleles are arbitrarily assigned an index $a \in 0, 1$.

Optimization.

Figure 13:
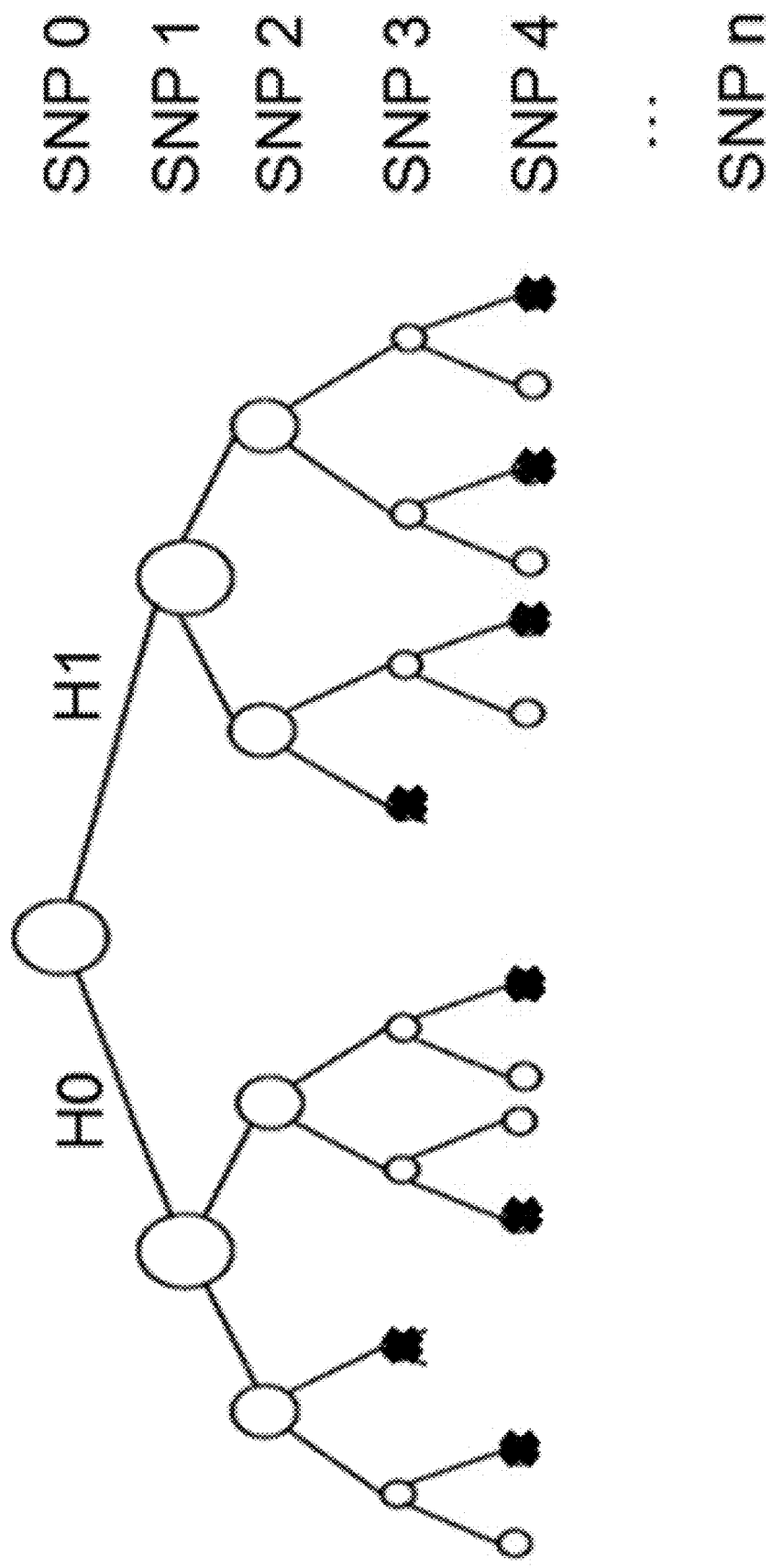
FIG. 13 illustrates a beam search in accordance with an embodiment of the systems and methods of the present disclosure.

In some embodiments, one of the overall objective functions presented above is optimized using a hierarchical search over the phasing vector $\vec{X}$. The objective function for the embodiment of $\vec{O} \in \{0, 1, -\}^n$ is illustrated in FIG. 12. In some embodiments, $\vec{X}$ is broken up into local chunks of $n \approx 40$ variants and the relative phasing of the block is determined using beam search over the assignments of $X_k$, $X_{k+1}, \ldots, X_{k+n}$, where k is the first variant in the local block. In some embodiments local chunks consists of between 10 and 20 variants, between 20 and 30 variants, between 30 and 40 variants, between 35 and 45 variants, between 40 and 50 variants, or more than 50 variants. Beam search is described at, for example, en.wikipedia.org/wiki/Beam_search, which is hereby incorporated by reference herein in its entirety. See also FIG. 13 which illustrates the beam search. In FIG. 13, at each stage of the beam search, only the k highest scoring partial solutions are retained. In FIG. 13, k=6. In FIG. 13, nodes marked with a red X are not in the top k, so they are not explored further.

The relative phasing of neighboring blocks is found greedily, yielding a candidate phasing vector $\vec{X}$. Finally $\vec{X}$ is iteratively refined by swapping the phase of individual variants. Convergence of this refinement yields an estimate of the optimal phasing configuration $\vec{X}$. In some embodiments, the confidence of each phasing decision is the likelihood-ratio between optimal and next-best solutions. In some embodiments, an estimate of the accuracy of the phasing configuration is determined by computing the likelihood ratio between the optimal configuration $\vec{X}$ and some alternate configuration $X_{alt}$ by computing the likelihood ratio between the hypotheses. In some embodiments, the confidence is then reported as a Phred-scaled quality value:

$$Q(X_{alt}) = -10\log_{10}\left(\frac{P(O \mid X_{alt})}{P(O \mid \hat{X})}\right)$$

In some embodiments, there are two classes of errors considered: short switch errors and long switch errors. Short switch errors are single variants that are assigned the wrong phasing in an otherwise correctly phased region. To measure the short switch confidence of variant i, $X_i$ is flipped to form $X_{alt}$. When the short switch confidence is low, the variant is marked as not phased in the output, rather than reporting a phasing call likely to be erroneous.

Long switch errors occur when two neighboring block of variants $\ldots, X_{i-2}, X_{i-1}$ and $X_i, X_{i+1}, \ldots$ are correctly phased internally, but have the wrong relative phasing between the two blocks. In this case, a long switch error is called at position i. The long switch confidence at position i is tested by inverting the phase of $X_j$ for all i>=1 When the long switch confidence falls below a threshold, a new phase block is started and variants in different phase blocks are not called as phased with respect to one another.

Example 1

Sample Preparation

Figure 8:
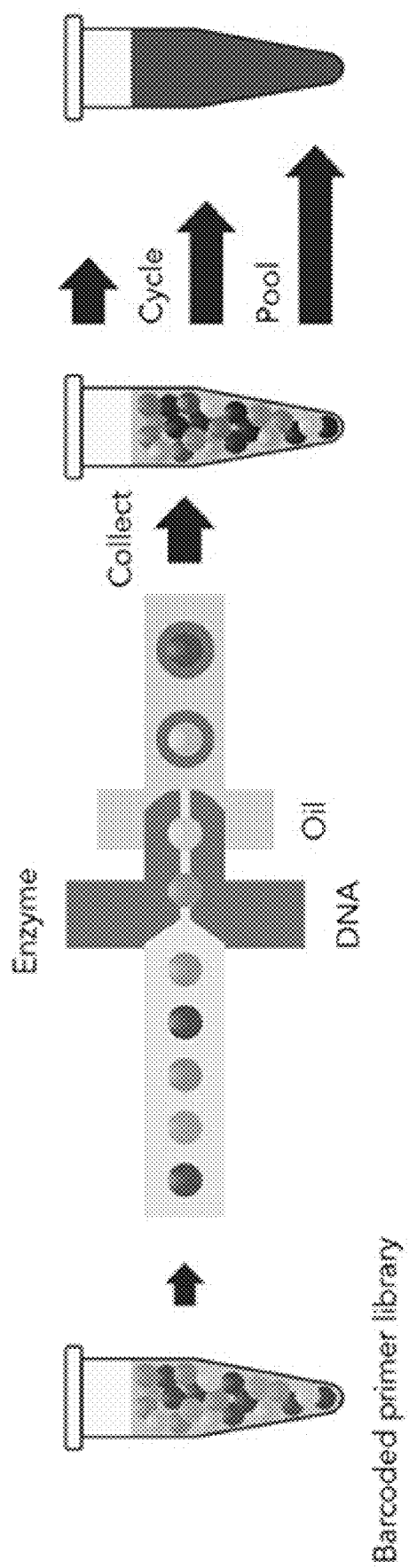
FIG. 8 illustrates an overview of a bar-coded library creation process in accordance with an embodiment of the present disclosure.

FIG. 8 provides an example of sample preparation in accordance with an exemplary embodiment of the present disclosure. The GemCode Platform massively partitions and barcodes DNA, producing sequencing-ready libraries with >100,000 unique barcodes. Custom algorithms use this barcode information to map reads back to original, long molecules of DNA, creating linked reads that span many tens of kilobases. Long template molecules from ~1 ng of gDNA are randomly distributed across >100,000 barcoded partitions, giving <10 fg (<0.3% of the genome) per partition. Each partition carries primers with barcodes that are constant within a partition, but distinct across partitions. An amplification reaction creates barcoded short read library fragments within each partition. The resulting library is compatible with standard exome capture, while preserving long range linkage information. In particular, the resulting libraries are sample-indexed and can be whole genome sequenced, or used as input into one of many commercially available hybrid capture platforms to generate targeted sequencing libraries. The powerful nature of this new linked read data type means that long-range information is retained after target enrichment, even though intronic regions are not selected or sequenced.

Linked Reads.

Figure 9:
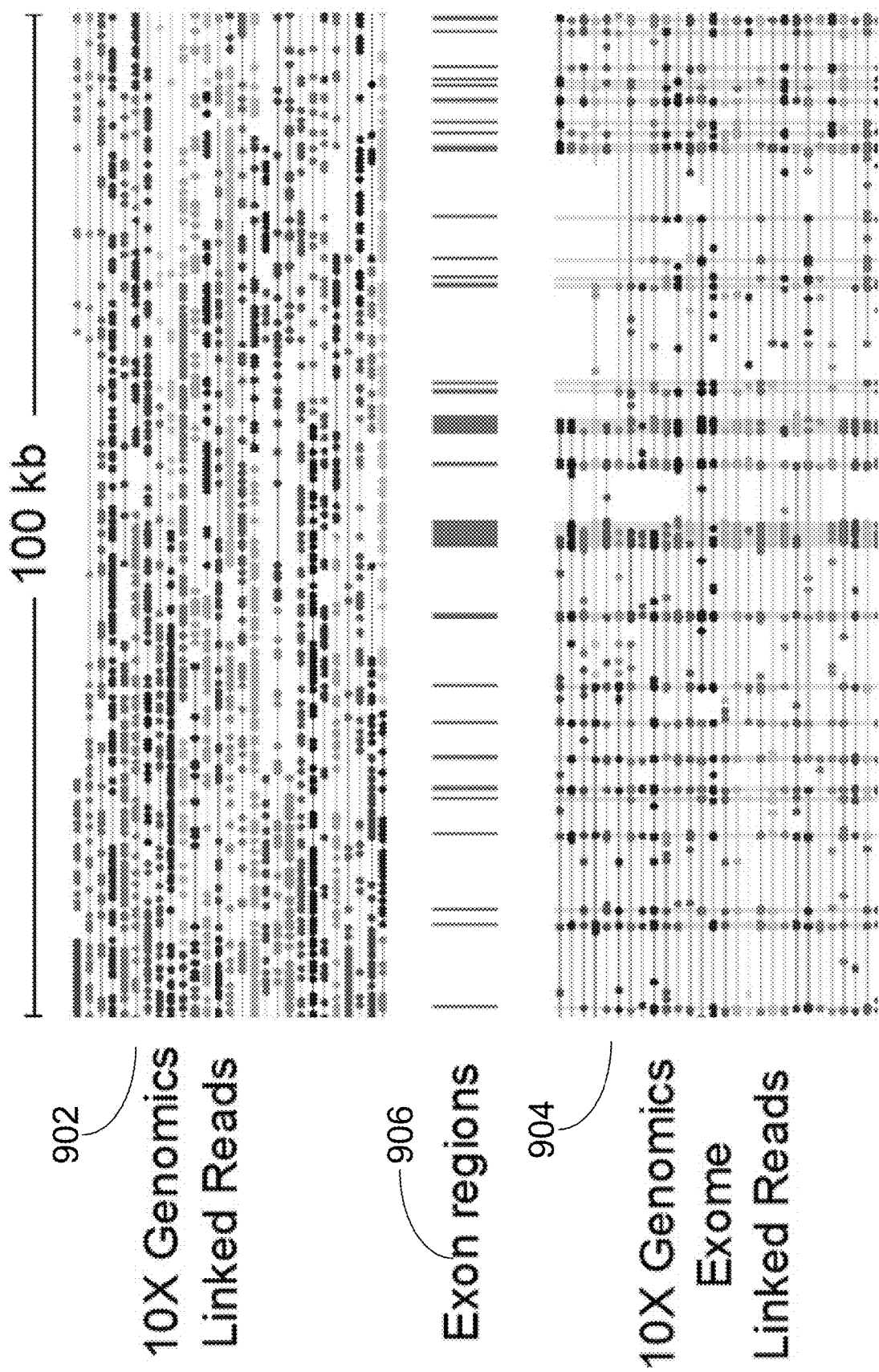
FIG. 9 illustrates linked sequence reads in accordance with the present disclosure in which each dot in the figure represents a read-pair and group of such read-pairs that are joined by a horizontal line share a common barcode from a pool more than 100,000 barcodes.

Referring to FIG. 9, after mapping, reads from the same locus with the same barcode form a set of 'linked reads' that were generated from a single input molecule. In exome data, linked reads span multiple target regions, allowing phasing and structural variant calling from exome data. In FIG. 9, each dot represents NGS read-pair (e.g., a sequence read). Groups of such sequence reads joined by a horizontal line in FIG. 9 share a common barcode from a pool of over 100,000 barcodes used to sequence the test nucleic acid. Moreover, the horizontal lines are arranged into respective groups 902 and 904, each such group representing the two parental haplotypes of the diploid organism from which the test nucleic acid was obtained. Further illustrated in FIG. 9 are the locations 906 of exons within the genome of the test nucleic acid. Each such exon is illustrated as a vertical bar within the figure.

Sequencing Results.

Referring to FIG. 10, the libraries of sequence reads from target nucleic acid obtained from two different organisms (respectively labeled NA12878 WGS and NA12878 WES) achieve low PCR duplication rates and high mapped fractions, despite requiring only 1 ng of input material. Each input molecule generates a group of tens of linked reads.

Phasing.

The disclosed systems and methods for phasing (column NA12878 WES) were compared with phased genomes generated from pedigree phasing (Cleary et al., 2014, "Joint variant and de novo mutation identification on pedigrees from high-throughput sequencing data," *J Comput Biol*, 21:405-419, which is hereby incorporated by reference in its entirety) (NA12878 WGS), sperm direct haplotyping (Kirkness et al., 2013, "Sequencing of isolated sperm cells for direct haplotyping of a human genome," *Genome Res*, 23:826-832, which is hereby incorporated by reference in its entirety) (HuRef1 WGS), and fosmid pooling (Kitzman et al., 2011, "Haplotype-resolved genome sequencing of a Gujarati Indian individual." *Nat Biotechnol*, 29:59-63, which is hereby incorporated by reference in its entirety) (NA20847 WGS), by phasing existing variant calls. These results are summarized in FIG. 14. High concordance with previous results is found and MB-scale phase blocks at modest coverage levels is consistently achieved. With exome sequencing, 96% of the genes shorter than 100 kb are contained in single phase blocks using the systems and method of the present disclosure.

Structural Variant Determination—Results of Large Scale Structural Variant Detection—WGS Case Study CEPH Trio.

In this example, all called deletions were found in previous studies. Eight deletions previously reported by three other studies, Kidd et al., 2010, "A human genome structural variation sequencing resource reveals insights into mutational mechanisms," Cell, 143:837-47; Layer et al., 2014, "LUMPY: a probabilistic framework for structural variant discovery," Genome Biol, 15:R84; and Mills et al., 2011, "Mapping copy number variation by population-scale genome sequencing," Nature, 470:59-65, each of which is hereby incorporated by reference, were selected for further validation using OS-seq (Myllykangas et al., 2011, "Efficient targeted resequencing of human germline and cancer genomes by oligonucleotide-selective sequencing," *Nat Biotechnol*, 29:1024-1027, which is hereby incorporated by reference, phasing information, LOH, and depth of coverage. Tables 1 and 2 provide the results.

TABLE 1

|  | Detected by the SV algorithm of the present disclosure | Not detected by the SV algorithm of the present disclosure |
| --- | --- | --- |
| Validated | 5 | 0 |
| Not Validated | 0 | 3 |

All calls in the child were consistent with Mendelian inheritance (see structural variant phasing section). Trio information was not used for phasing the structural variants.

TABLE 2

|  | NA12878 (mother) | NA12877 (father) | NA12882 (child) |
| --- | --- | --- | --- |
| Number of structural variants greater than 50 kb | 20 | 9 | 13 |
| Percentage of het structural variants phased | 81.2% | 88.9% | 100% |

Structural Variant Determination Exome Case Study: H2228.

The lung cancer cell line H2228 has two validated gene fusions with breakpoints inside long introns (Choi et al., 2008, "Identification of novel isoforms of the EML4-ALK transforming gene in nonsmall cell lung cancer," Cancer Res, 68:4971-4976; and Jung et al., 2012, "Discovery of ALK-PTPN3 gene fusion from human non-small cell lung carcinoma cell line using next generation RNA sequencing," Genes Chromosomes Cancer, 51:590-597, each of which is hereby incorporated by reference. These breakpoints can be detected with linked reads despite the absence of overlapping capture targets. Table 3 provides the results.

TABLE 3

|  | Rank | Intron Lengths |
| --- | --- | --- |
| ALK-EML4 | 3 | 2K, 16K |
| ALK-PTPN3 | 8 | 2K, 6K |

Structural Variant Phasing Approach—Taken in Example 1.

Figure 15:
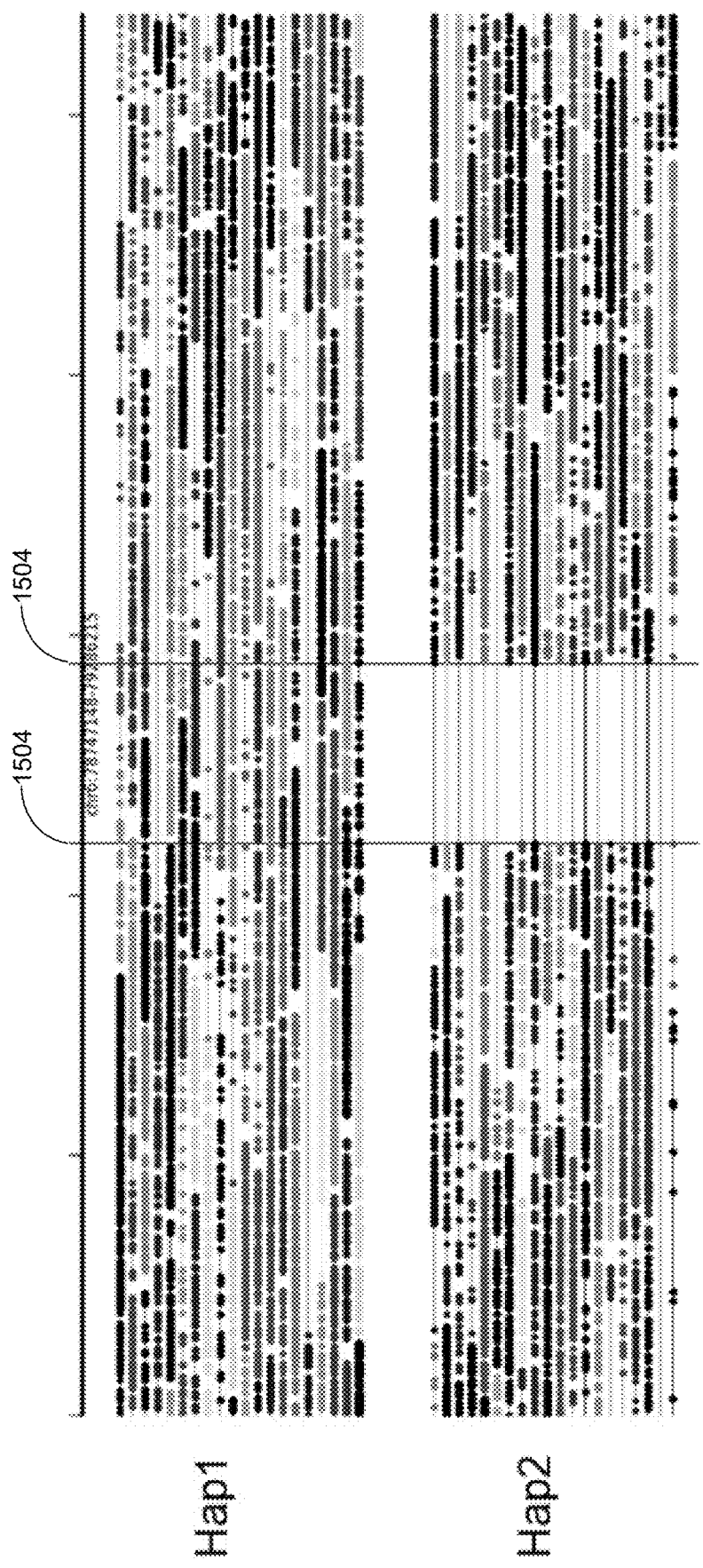
FIG. 15 illustrates a phased structural variant call in accordance with an embodiment of the systems and methods of the present disclosure in which linked reads split by the haplotype assignment of each input molecule reveals the phased structure of the structural variant. Vertical bars indicate the breakpoints of the structural variant call.

During phasing the haplotype of each template molecule is computed concurrently with the variants. By associating each barcode supporting a structural variant with the haplotype it derived from, structural variants can be phased. Phasing structural variants provides a powerful confirmation method false positive structural variants are unlikely to phase to a single haplotype. A p-value for the association of a structural variant to a haplotype is computed using a binomial test. FIG. 15 illustrates a phased structural variant call. Splitting linked reads by the haplotype assignment of each input molecule reveals the phased structure of the structural variant. Vertical bars 1504 indicate the breakpoints of the structural variant call.

FIG. 16 illustrates called deletions in NA12878. Barcodes supporting the structural variant calls are phased to a single haplotype. The three structural variants at the bottom of the table represent short-read false positive calls, correctly filtered by the disclosed algorithm. False positive calls do not phase uniquely or follow Mendelian inheritance patterns.

Example 2

This example describes technologies relating to detecting structural variants and phasing haplotypes from cancer exome sequencing. Specifically incorporated into Example 2 is U.S. Provisional Patent Application 62/120,330, entitled "Detecting Structural Variants and Phasing Haplotypes from Cancer Exome Sequencing Using 1 ng Dna Input," filed Feb. 24, 2015, which is hereby incorporated by reference in its entirety.

Structural changes, and particularly gene fusions, are known driving mutations in many cancers. In many cases they have also proven to be effective drug targets. However, detecting fusions is a challenge with existing short-read sequencing technologies, particularly when using exon target enrichment approaches to achieve the ultra-deep coverage required to sensitively detect important mutations in heterogeneous cancer samples. Accordingly, what is needed in the art are improved systems and methods for detecting important mutations in heterogeneous cancer samples.

Technical solutions (e.g., computing systems, methods, and non-transitory computer readable storage mediums) for detecting important mutations in heterogeneous cancer samples are provided in this Example. In particular, a new platform from 10× Genomics is used to address multiple challenges in cancer sequencing: (i) detecting gene fusion events from exome sequencing data, (ii) obtaining complex sequencing libraries from ~1 ng DNA input, (iii) phasing single nucleotide polymorphisms and structural variants, and (iv) resolving complex rearrangements.

Figure 17:
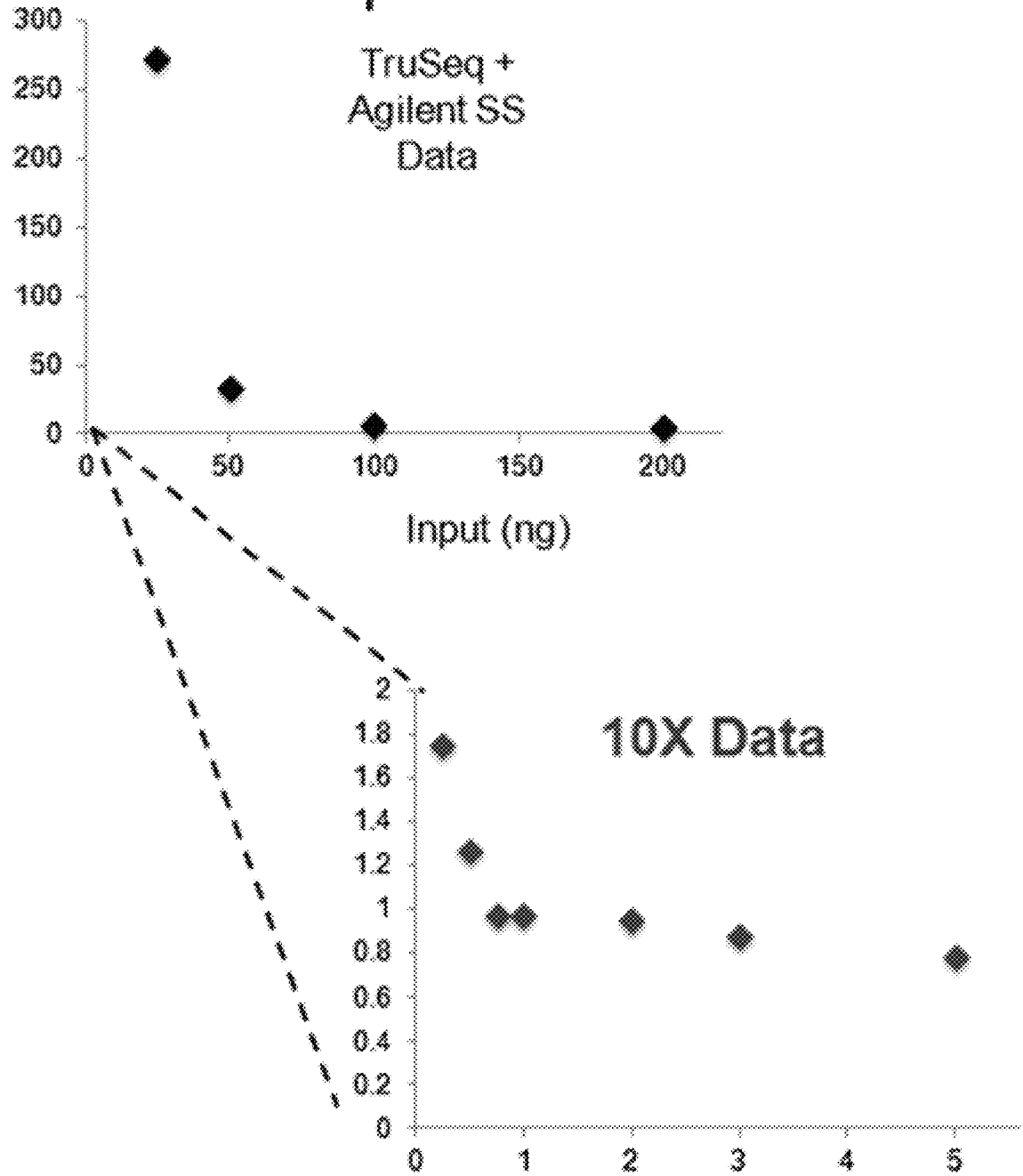
FIG. 17 compares PCR duplication rate between the disclosed systems and methods (10x) and that of TruSeq+ AGILENT SS data at various input quantities in accordance with an embodiment of the present disclosure.
Figure 18:
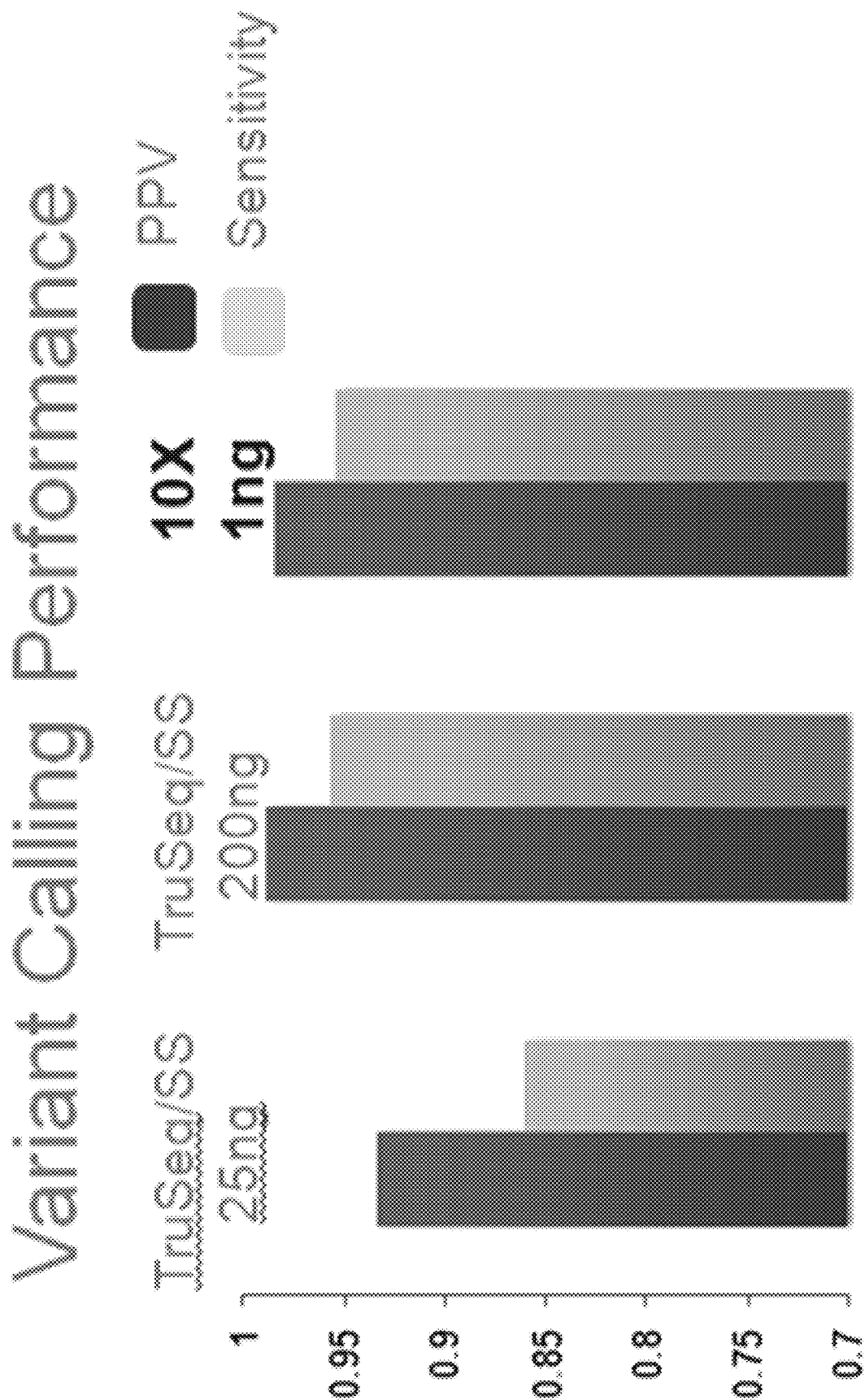
FIG. 18 compares variant calling performance between the disclosed systems and methods (10x) and that of TruSeq/SS at various input quantities.

In Example 2, sample preparation and determination of linked reads was as given in Example 1 with reference to FIGS. 8 and 9. Cancer cell line and matched normal DNA was acquired from ATCC and size selected for fragments ≥20 kb using the BluePippin from Sage Science. Sequencing libraries were prepared using ~1 ng of gDNA input into the GemCode Platform. 5 mg of library was used for exome capture using the AGILENT SURESELECT Human All Exon V5+UTRs with IDT xGen® Universal Blocking Oligos. Libraries were sequenced on an ILLUMINA HiSeq 2500 using a paired-end 2×98 run. Sequencing results were analyzed and visualized using the GEMCode Software Suite. FIG. 17 compares the PCR duplication rate between the methodology of the disclosed systems and methods and that of TruSeq+AGILENT SS data at various input quantities. FIG. 18 compares variant calling performance between the 10× methodology and that of TruSeq/SS at various input quantities. FIG. 19 provides sequencing metrics for various sample runs using the 10× methodology. FIGS. 17 through 19 show that the disclosed systems and methods (e.g., the 10× GemCode Platform) generates high complexity sequencing libraries using inputs in the ~1 ng range. This high complexity allows for deeper targeted sequencing and more sensitive variant calling when sample quantities are limited.

Referring to FIG. 20, previously annotated rearrangements that occur within 30 kb of a region targeted with exome capture were compared to gene fusions detected using the systems and methods of the present disclosure (e.g., GemCode Platform with Whole Exome Sequencing). Previous annotations were found using whole genome sequencing or RNA-based analysis.

Figure 21:
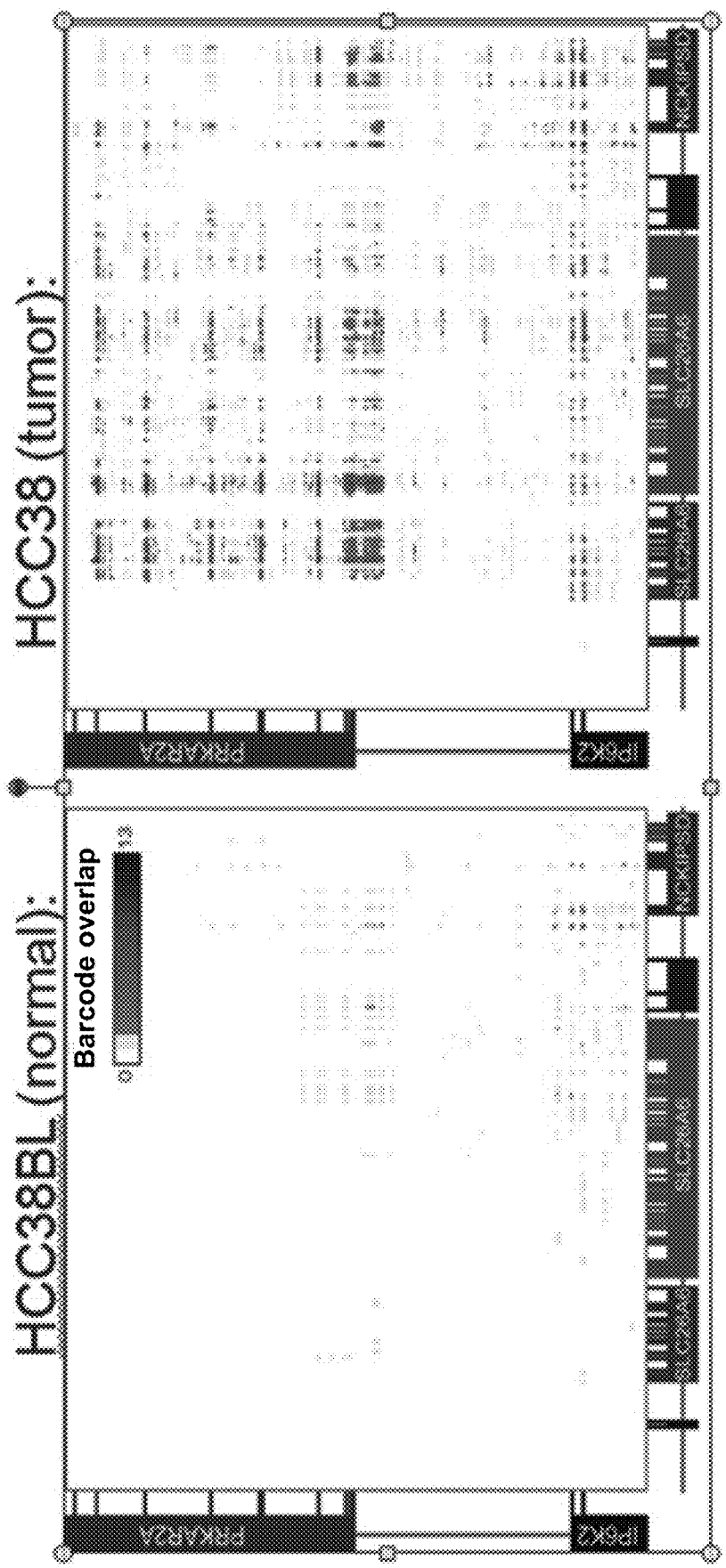
FIG. 21 illustrates high confidence detection of a tumor-specific gene fusion in HCC38 triple negative breast cancer cell line in accordance with embodiments of the present disclosure.

FIG. 21 illustrates high confidence detection of a tumor-specific gene fusion in HCC38 triple negative breast cancer cell line using the systems and methods of the present disclosure.

Figure 22:
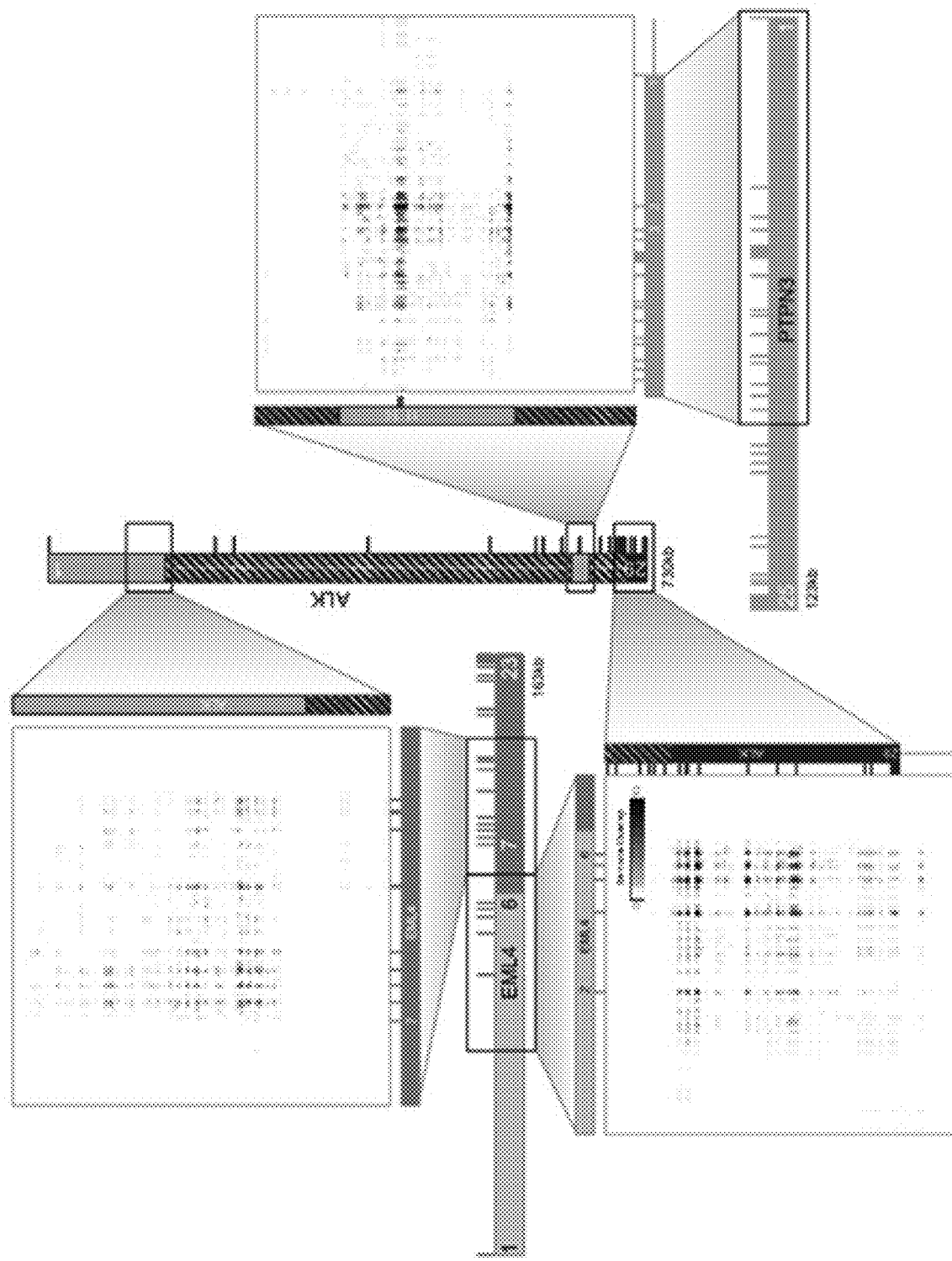
FIGS. 22 and 23 illustrate resolving complex rearrangements using the systems and methods of the present disclosure.
Figure 23:
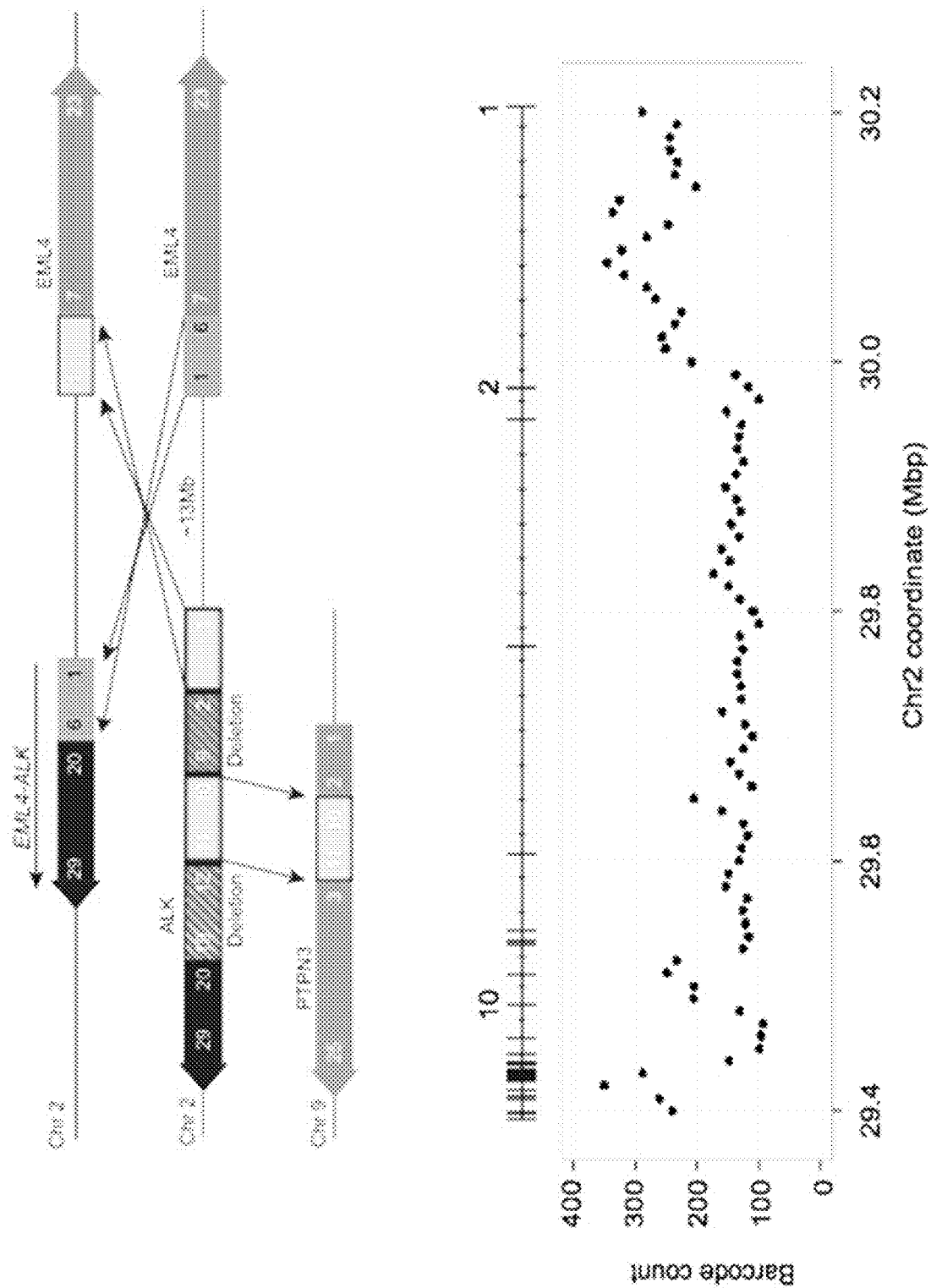

FIGS. 22 and 23 illustrate resolving complex rearrangements using the systems and methods of the present disclosure. In particular, looking for the EML4/ALK fusion in H2228 lung cancer cell line reveals a much more complex event: whole genome sequencing BC and read counts confirm presence of a deletion within exons 2-19 of ALK.

FIG. 24 illustrates haplotype phasing of gene fusion events in accordance with some embodiments of the present disclosure.

Figure 25:
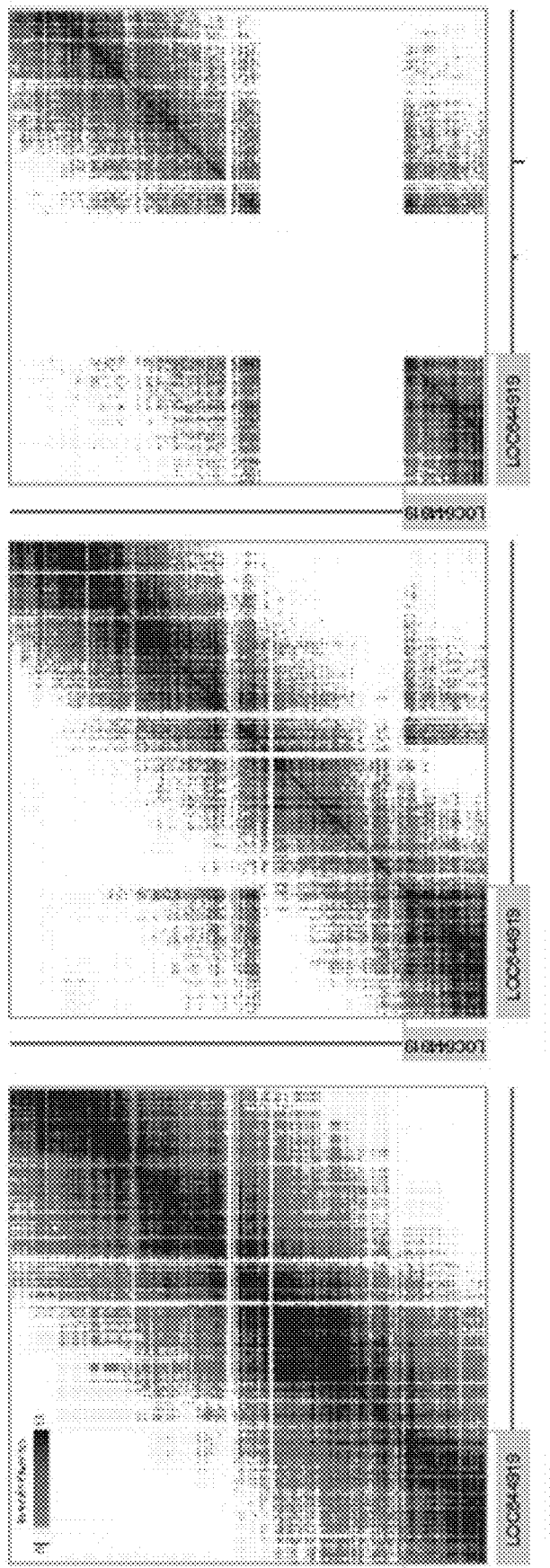
FIGS. 25 and 26 illustrate how whole-genome sequencing linked reads and phasing reveal a complex deletion and allele loss event in HCC1143 triple negative breast cancer.
Figure 26:
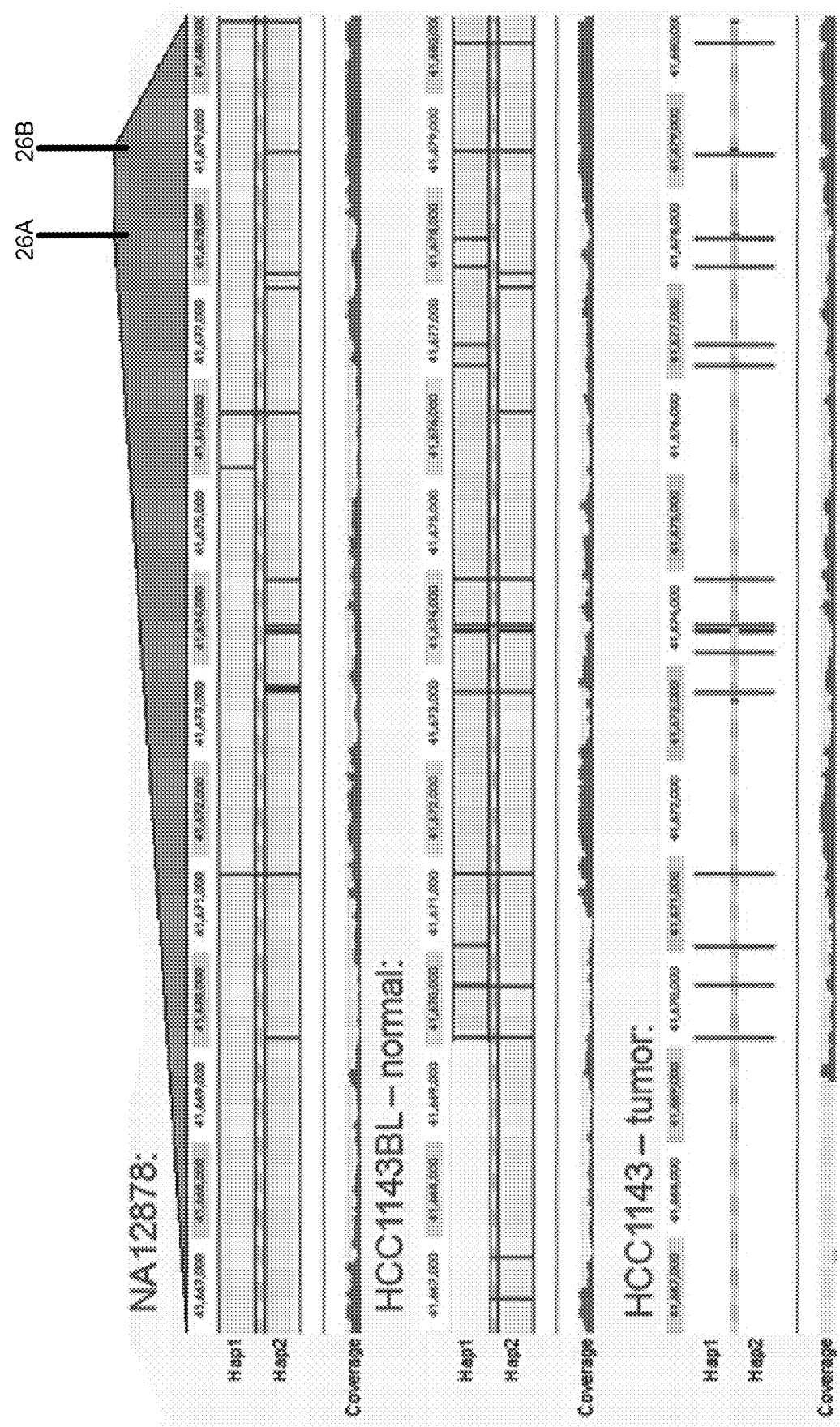

FIGS. 25 and 26 illustrate how whole-genome sequencing linked reads and phasing reveal a complex deletion and allele loss event in HCC1143 triple negative breast cancer. Lines 26A and 26B provide the relative positioning of FIG. 26 with respect to the X axis of FIG. 25.

Figure 27:
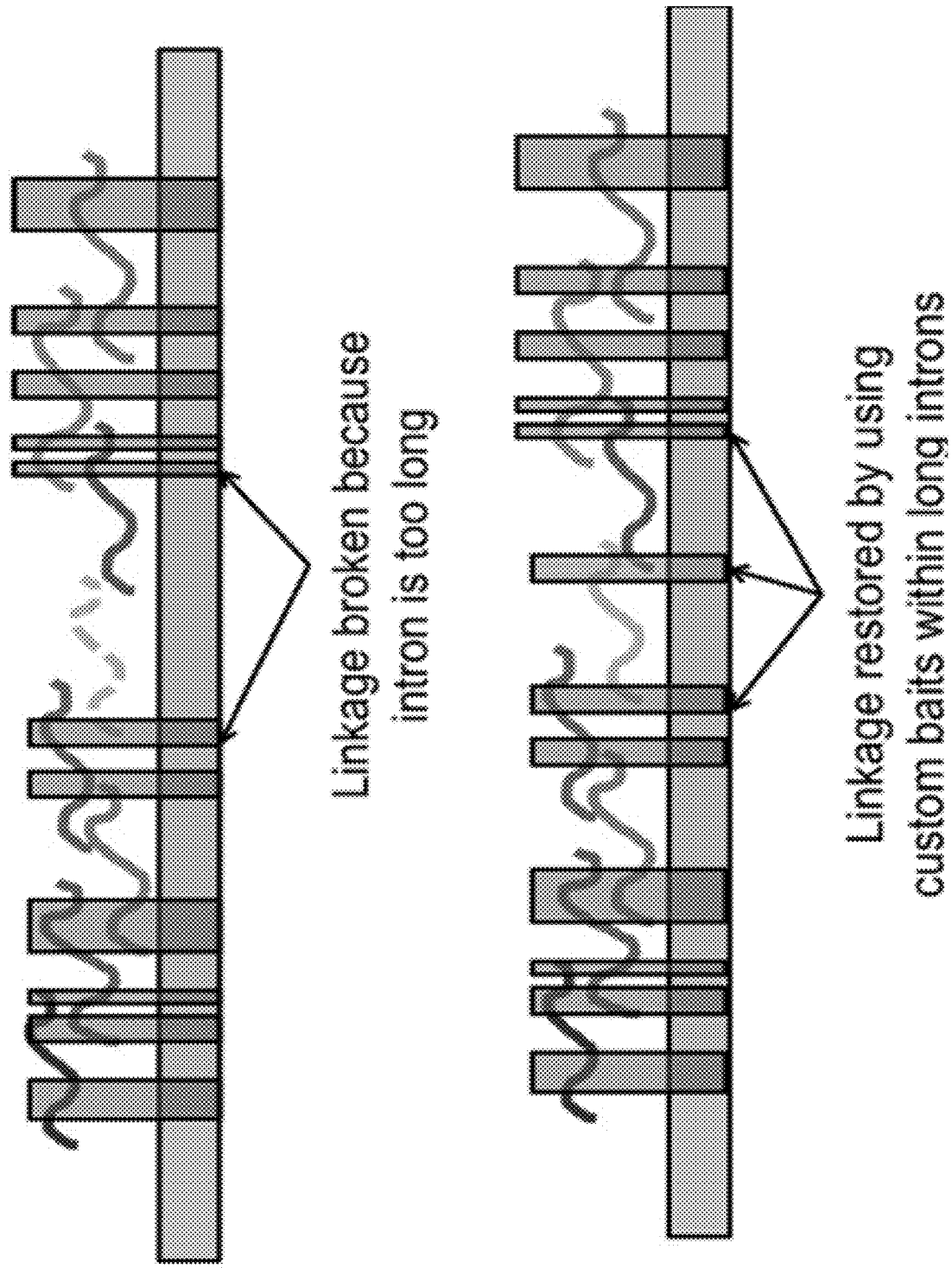
FIG. 27 illustrates a schematic for detecting BCR-ABL with whole exome sequencing in which there is extra baiting of long introns in accordance with embodiments of the present disclosure.
Figure 28:
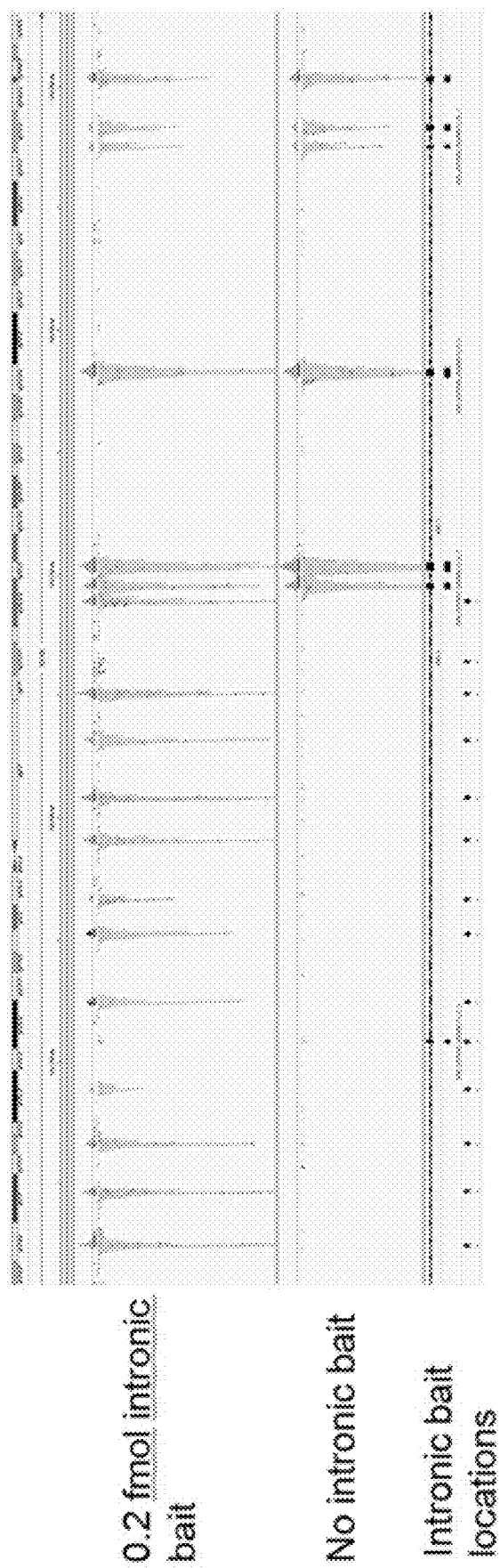
FIGS. 28 and 29 illustrate how a 10× GemCode library was generated from an input of ~1 ng of KU812 gDNA using the systems and methods of the present disclosure. Hybrid capture was done with the standard IDT Exome panel, with (Exome+) or without (Exome) additional Ultramer DNA baits that map to the >100 kb intronic region between exon 1 and exon 2 of ABL1 (average bait spacing ~2 kb).
Figure 29:
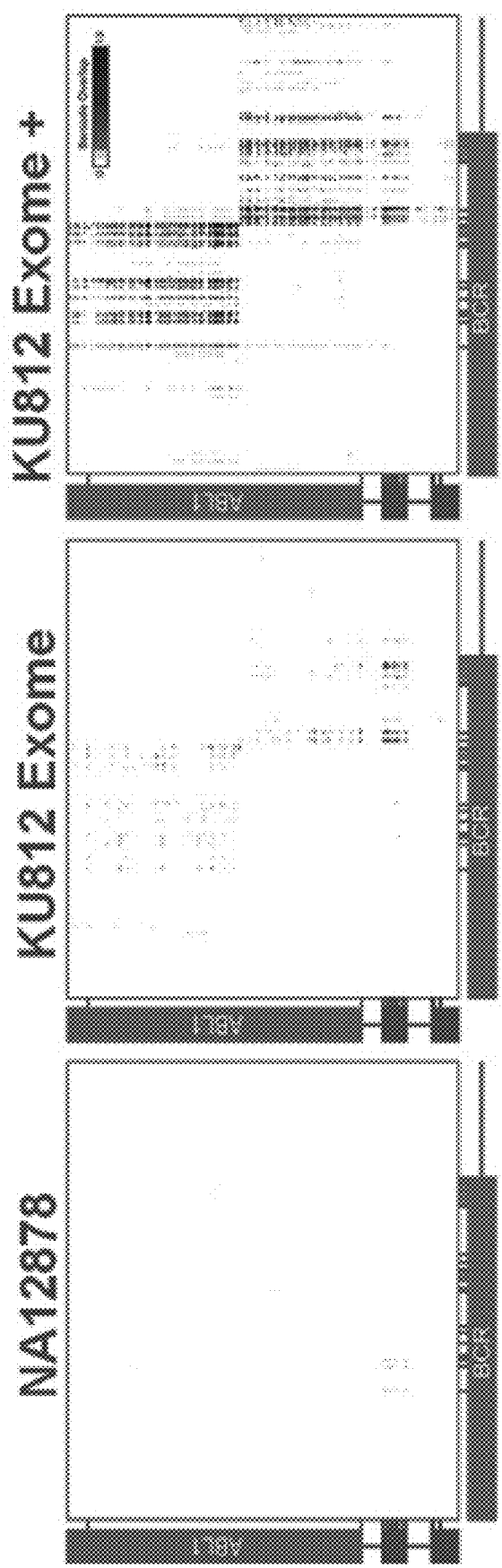

FIG. 27 illustrates a schematic for detecting BCR-ABL with whole exome sequencing in which there is extra baiting of long introns. Referring to FIGS. 28 and 29, a 10× GemCode library was generated from an input of ~1 ng of KU812 gDNA using the disclosed systems and methods. Hybrid capture was done with the standard IDT Exome panel, with (Exome+) or without (Exome) additional Ultramer DNA baits that map to the >100 kb intronic region between exon 1 and exon 2 of ABL1 (average bait spacing 2 kb). FIG. 30 summarizes structural variant statistics for 0.2 fmol of intronic bait versus no intronic bait runs.

CONCLUSION

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms "first," "second," etc. may be used herein to describe various elements, these elements should not be limited by these terms. These terms are only used to distinguish one element from another. For example, a first object could be termed a second object, and, similarly, a second object could be termed a first object, without changing the meaning of the description, so long as all occurrences of the "first object" are renamed consistently and all occurrences of the "second object" are renamed consistently. The first object and the second object are both objects, but they are not the same object.

The terminology used herein is for the purpose of describing particular implementations only and is not intended to be limiting of the claims. As used in the description of the implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined (that a stated condition precedent is true)" or "if (a stated condition precedent is true)" or "when (a stated condition precedent is true)" may be construed to mean "upon determining" or "in response to determining" or "in accordance with a determination" or "upon detecting" or "in response to detecting" that the stated condition precedent is true, depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A method of phasing sequencing data of a test nucleic acid sample obtained from a biological sample from a single organism of a species, wherein the test nucleic acid sample comprises a first set of haplotypes ($H_0$) and a second set of haplotypes ($H_1$), the method comprising:
   at a computer system having one or more processors, and memory storing one or more programs for execution by the one or more processors:
   (A) obtaining a reference sequence for all or a portion of a genome of the species;
   (B) obtaining a plurality of variant calls $A_{i,p}$ for the biological sample, wherein i is an index to a position in the reference sequence, and $p \in \{0, 1, -1\}$ in which label 0 assigns a respective variant call in $A_{i,p}$ to $H_O$, label 1 assigns the respective variant call to $H_1$, and label $-1$ assigns the respective variant call to the zygosity error condition $H_{-1}$;

(C) obtaining a plurality of sequence reads $\vec{O}$ for the biological sample, wherein the plurality of sequence reads $\vec{O}$ comprises at least 100,000 sequence reads and collectively represents at least 1000 different regions of the reference sequence, each respective sequence read $\vec{O}_i$ in the plurality of sequence reads comprises a first portion that corresponds to a subset of the reference sequence and a second portion that encodes a respective barcode, independent of the reference sequence, for the respective sequence read, in a plurality of barcodes, and each respective sequence read $\vec{O}i$ in the plurality of sequence reads is $\in \{0, 1, -1, -\}^n$, wherein (i) n is the number of variants calls in $A_{i,p}$, (ii) each respective label 0 for the respective sequence read $\vec{O}i$ assigns a corresponding variant call in $A_{i,p}$ to $H_0$, (iii) each respective label 1 for the respective sequence read $\vec{O}i$ assigns a corresponding variant call in $A_{i,p}$ to $H_1$, (iv) each respective label $-1$ for the respective sequence read $\vec{O}i$ assigns a corresponding variant call in $A_{i,p}$ to $H_{-1}$, and (v) each respective label – for the respective sequence read $\vec{O}i$ indicates that the corresponding variant call in $A_{i,p}$ is not covered; and (D) refining a phasing vector result $\hat{X}$ by optimization of haplotype assignments at individual positions i in $A_{i,p}$ between $H_O$, $H_1$ and $H_{-1}$ for the plurality of sequence reads using an overall objective function:

$$\hat{X} = \genfrac{}{}{0pt}{}{\text{argmax}}{\vec{X}} \, P(\vec{X} \mid \vec{O}) \bigg| = \frac{P(\vec{X})P(\vec{O} \mid \vec{X})}{C}$$

wherein, $$P(\vec{X}) = \prod_i \frac{(1-\varepsilon_i)}{2}(X_i = H_1) + (X_i = H_0) + \varepsilon_i(X_i = H_{-1}),$$

$\varepsilon_i$ is an estimate of incurring $H_{-1}$ at position i, $$P(\vec{O} \mid \vec{X}) = \prod_f P(O_{1,f}, \ldots, O_{N,f}),$$

$\hat{X}$ is the refined phasing vector result,
C is a constant,
$\vec{X}$ is the phasing vector result to be inferred, and
$(O_{1,f}, \ldots, O_{N,f})$ is the respective subset of N variant calls in the plurality of variant calls $A_{i,p}$ observed in the subset of sequence reads that include the same respective barcode from the plurality of barcodes,
thereby phasing sequencing data of the test nucleic acid sample in the form of the refined phasing vector result $\vec{X}$.

2. The method of claim 1, wherein $$P(O_{1,f}, \ldots, O_{N,f} | \vec{X}, H_f=0) = \Pi_i P(O_{i,f} | A_i, X_i),$$

$$P(O_{1,f}, \ldots, O_{N,f} | \vec{X}, H_f=1) = \Pi_i P(O_{i,f} | A_i, 1-X_i),$$

$$P(O_{1,f}, \ldots, O_{N,f} | \vec{X}, H_f=M) = \Pi_i 0.5,$$

M indicates a mixture of $H_f=0$ and $H_f=1$ for the respective barcode f, $$P(O_{i,f}, \ldots, O_{N,f} | \vec{X}) = \frac{(1-\alpha)}{2}\left(\prod_i P(O_{i,f} | A_i, X_i) + \prod_i P(O_{i,f} | A_i, 1-X_i)\right) + \alpha \prod_i 0.5,$$

$$\log P(O_{i,f} | A_{i,p}) = \sum_r 1(S_r = A_{i,p})(1 - 10^{-Q_r/10}) +$$
$$1(S_r \neq A_{i,p})(10^{-Q_r/10}) + 1(A_{i,p} = H_{-1})^{0.5}$$

$\alpha$ is a predetermined fractional value representing a likelihood or probability that $H_f=M$ arises, i is the $i^{th}$ variant in the respective subset of N variant calls observed for the subset of sequence reads that include the same respective barcode, r sums over the subset of sequence reads that include the same respective barcode, $1(S_r = A_{i,p})$ is an indicator function testing if the base assignment at position i in the $r^{th}$ sequence read $S_r$ in the subset of sequence reads that include the same respective barcode matches $A_{i,p}$, wherein when they match $1(S_r = A_{i,p})$ has a value of 1 and when they do not match $1(S_r = A_{i,p})$ has a value of zero, $1(S_r \neq A_{i,p})$ is an indicator function testing if the base assignment at position i in the $r^{th}$ sequence read $S_r$ in the subset of sequence reads that include the same respective barcode does not match $A_{i,p}$, wherein when they do not match $1(S_r \neq A_{i,p})$ has a value of 1 and when they do match $1(S_r = A_{i,p})$ has a value of zero, $1(A_{i,p} = H_{-1})$ is an indicator function that has a value of 1 when $A_{i,p}$ is equal to $H_{-1}$ and is a value of zero otherwise, and $Q_r$ is a quality value for $S_r$ for the read base at the position of i in the reference sequence.

3. The method of claim 1, wherein
the first set of haplotypes ($H_0$) consists of maternal haplotypes for the single organism, and
the second set of haplotypes ($H_1$) consists of paternal haplotypes for the single organism.

4. The method of claim 1 wherein the plurality of barcodes comprise 1000 or more barcodes and the plurality of variant calls $A_{i,p}$ comprise 1000 or more variant calls.

5. The method of claim 1, wherein $\vec{X}$ is (x), wherein
x is a binary string of length n,
each value of 0 in x indicates origination of the corresponding variant call in the first set of haplotypes ($H_0$), and
each value of 1 in x indicates origination of the corresponding variant call in the second set of haplotypes ($H_1$).

6. The method of claim 1, wherein the subset of sequence reads that include the same respective barcode f comprises 10 or more sequence reads.

7. The method of claim 1, wherein the refining (D) optimizes the overall objective function using a hierarchical search over $\vec{X}$.

8. The method of claim 7, wherein the hierarchical search comprises:
for each respective local block of variant calls in $A_{i,p}$ that are localized to a corresponding subset of the reference sequence, using a beam search over the assignments of $X_k$, $X_{k+1}$, ..., $X_{k+j}$ in the respective local block of variant calls, wherein k is the first variant in the respective local block of variant calls, j is a number of variant calls in the respective local block of variant calls and wherein assignments of $X_k$, $X_{k+1}$, ..., $X_{k+j}$ are found by computing the objective function in which the phasing vector of the objective function in respective computations is limited to $X_k$, $X_{k+1}$, ..., $X_{k+j}$, thereby finding an optimal phasing solution for each respective local block of variant calls, and
greedily joining neighboring local blocks of variant calls in $A_{i,p}$ using the optimal phasing solution for each respective local block of variant calls thereby obtaining an estimate of the optimal phasing configuration $\vec{X}$.

9. The method of claim 8, wherein the refining the phasing vector result further comprises iteratively swapping the phase result of individual $x_i$ in the estimate of the optimal phasing configuration $\vec{X}$ and recomputing the objective function, thereby obtaining $\vec{X}$.

10. The method of claim 8, wherein a respective local block of variant calls consists of between 20 and 60 variants in $A_{i,p}$.

11. The method of claim 8, wherein an iteration of the beam search for the assignments of one of $X_k$, $X_{k+1}$, ..., $X_{k+j}$ discards all but a predetermined number of solutions for $\vec{X}$.

12. The method of claim 1, wherein the barcode in the second portion of each respective sequence read in the plurality of sequence reads $\vec{O}$ encodes a unique predetermined value selected from the set {1, ..., 1024}, selected from the set {1, ..., 4096}, selected from the set {1, ..., 16384}, selected from the set {1, ..., 65536}, selected from the set {1, ..., 262144}, selected from the set {1, ..., 1048576}, selected from the set {1, ..., 4194304}, selected from the set {1, ..., 16777216}, selected from the set {1, ..., 67108864}, or selected from the set {1, ..., $1 \times 10^{12}$}.

13. The method of claim 1, wherein the plurality of variant calls is obtained from the plurality of sequence reads.

14. The method of claim 1, wherein the plurality of sequence reads is obtained from a plurality of barcoded-oligo coated gel-beads and wherein the test nucleic acid sample is 50 ng or less.

15. The method of claim 14 wherein the plurality of barcoded-oligo coated gel-beads comprises 10,000 beads, the test nucleic acid sample is 2.5 ng or less, and the plurality of sequencing reads $\vec{O}$ is obtained within ten minutes of exposure to the plurality of barcodes.

16. The method of claim 1, the method further comprising:
using the phasing vector result $\vec{X}$ to identify a structural variation in the single organism.

17. The method of claim 16, wherein the using the phasing vector result $\vec{X}$ to identify the structural variation in the single organism further comprises identifying the structural variation as cis or trans.

18. The method of claim 1, wherein the plurality of sequence reads $\vec{O}$ comprises at least $1\times10^6$ sequence reads.

19. The method of claim 1, wherein the plurality of sequence reads $\vec{O}$ collectively represents at least 10,000 different regions of the reference sequence.

20. The method of claim 1, wherein the plurality of sequence reads $\vec{O}$ collectively represents at least $1\times10^6$ different regions of the reference sequence.

21. A computing system comprising:
one or more processors;
memory storing one or more programs to be executed by the one or more processors;
the one or more programs comprising instructions for phasing sequencing data of a test nucleic acid sample obtained from a biological sample from a single organism of a species, wherein the test nucleic acid sample comprises a first set of haplotypes ($H_0$) and a second set of haplotypes ($H_1$), by executing a method comprising:
(A) obtaining a reference sequence for all or a portion of a genome of the species;
(B) obtaining a plurality of variant calls $A_{i,p}$ for the biological sample, wherein i is an index to a position in the reference sequence, and $p \in \{0, 1, -1\}$ in which label 0 assigns a respective variant call $A_{i,p}$ to $H_0$, label 1 assigns the respective variant call to $H_1$, and label $-1$ assigns the respective variant call to the zygosity error condition $H_{-1}$;
(C) obtaining a plurality of sequence reads $\vec{O}$ for the biological sample, wherein the plurality of sequence reads $\vec{O}$ comprises at least 100,000 sequence reads and collectively represents at least 1000 different regions of the reference sequence,
each respective sequence read $\vec{O}i$ in the plurality of sequence reads comprises a first portion that corresponds to a subset of the reference sequence and a second portion that encodes a respective barcode, independent of the reference sequence, for the respective sequence read, in a plurality of barcodes, and
each respective sequence read $\vec{O}i$ in the plurality of sequence reads is $\in \{0, 1, -1, -\}^n$, wherein (i) n is the number of variant calls $A_{i,p}$, (ii) each respective label 0 for the respective sequence read $\vec{O}i$ assigns a corresponding variant call in $A_{i,p}$ to $H_0$, (iii) each respective label 1 for the respective sequence read $\vec{O}i$ assigns a corresponding variant call in $A_{i,p}$ to $H_1$, (iv) each respective label $-1$ for the respective sequence read $\vec{O}i$ assigns a corresponding variant call in $A_{i,p}$ to $H_{-1}$, and (v) each respective label $-$ for the respective sequence read $\vec{O}i$ indicates that the corresponding variant call in $A_{i,p}$ is not covered; and D) refining a phasing vector result $\vec{X}$ by optimization of haplotype assignments at individual positions i in $A_{i,p}$ between $H_0$, $H_1$ and $H_{-1}$ for the plurality of sequence reads using an overall objective function:

$$\hat{X} = \underset{\vec{X}}{\mathrm{argmax}}\, P(\vec{X}\mid\vec{O}) = \frac{P(\vec{X})P(\vec{O}\mid\vec{X})}{C}$$

wherein, $$P(\vec{X}) = \prod_i \frac{(1-\varepsilon_i)}{2}(X_i = H_1) + (X_i = H_0) + \varepsilon_i(X_i = H_{-1}),$$

$\varepsilon_i$ is an estimate of incurring $H_{-1}$ at position i, $$P(\vec{O}\mid\vec{X}) = \prod_f P(O_{1,f}, \ldots, O_{N,f}),$$

$\hat{X}$ is the refined phasing vector result,
C is a constant,
$\vec{X}$ is the phasing vector result to be inferred, and
$(O_{1,f}, \ldots, O_{N,f})$ is the respective subset of N variant calls $A_{i,p}$ observed in the subset of sequence reads that include the same respective barcode form the plurality of barcodes, thereby phasing sequencing data of the test nucleic acid sample in the form of the refined phasing vector result $\vec{X}$.

22. The computing system of claim 21, wherein $(O_{1,f}, \ldots, O_{N,f}\mid\vec{X}, H_f=0) = \Pi_i P(O_{i,f}\mid A_{i,X_i})$, $P(O_{1,f}, \ldots, O_{N,f}\mid\vec{X}, H_f=1) = \Pi_i P(O_{i,f}\mid A_{i,1-X_i})$, $P(O_{1,f}, \ldots, O_{N,f}\mid\vec{X}, H_f=M) = \Pi_i 0.5$, M indicates a mixture of $H_f=0$ and $H_f=1$ for the respective barcode f, $$P(O_{i,f}, \ldots, O_{N,f}\mid\vec{X}) = \frac{(1-\alpha)}{2}\left(\prod_i P(O_{i,f}\mid A_i, X_i) + \prod_i P(O_{i,f}\mid A_i, 1-X_i)\right) + \alpha \prod_i 0.5,$$

$$\log P(O_{i,f}\mid A_{i,p}) = \sum_r 1(S_r = A_{i,p})(1 - 10^{-Q_r/10}) +$$
$$1(S_r \neq A_{i,p})(10^{-Q_r/10}) + 1(A_{i,p} = H_{-1})^{0.5}$$

$\alpha$ is a predetermined fractional value representing a likelihood or probability that $H_f=M$ arises,
i is the $i^{th}$ variant in the respective subset of N variant calls observed for the subset of sequence reads that include the same respective barcode,
r sums over the subset of sequence reads that include the same respective barcode,
$1(S_r=A_{i,p})$ is an indicator function testing if the base assignment at position i in the $r^{th}$ sequence read $S_r$ in the subset of sequence reads that include the same respective barcode matches $A_{i,p}$, wherein when they match $1(S_r=A_{i,p})$ has a value of 1 and when they do not match $1(S_r=A_{i,p})$ has a value of zero,
$1(S_r \neq A_{i,p})$ is an indicator function testing if the base assignment at position i in the $r^{th}$ sequence read $S_r$ in the subset of sequence reads that include the same respective barcode does not match $A_{i,p}$, wherein when they do not match $1(S_r \neq A_{i,p})$ has a value of 1 and when they do match $1(S_r=A_{i,p})$ has a value of zero,
$1(A_{i,p}=H_{-1})$ is an indicator function that has a value of 1 when $A_{i,p}$ is equal to $H_{-1}$ and is a value of zero otherwise, and $Q_r$ is a quality value for $S_r$ for the read base at the position of i in the reference sequence.

23. The computing system of claim 21, wherein the plurality of sequence reads $\vec{O}$ comprises at least $1 \times 10^6$ sequence reads.

24. The computing system of claim 21, wherein the plurality of sequence reads $\vec{O}$ collectively represents at least 10,000 different regions of the reference sequence.

25. The computing system of claim 21, wherein the plurality of sequence reads $\vec{O}$ collectively represents at least $1 \times 10^6$ different regions of the reference sequence.

26. A non-transitory computer readable storage medium storing one or more programs configured for execution by a computer, the one or more programs comprising instructions for phasing sequencing data of a test nucleic acid sample obtained from a biological sample from a single organism of a species, wherein the test nucleic acid sample comprises a first set of haplotypes ($H_0$) and a second set of haplotypes ($H_1$), the one or more programs collectively executing a method comprising:

(A) obtaining a reference sequence for all or a portion of a genome of the species;

(B) obtaining a plurality of variant calls $A_{i,p}$ for the biological sample, wherein i is an index to a position in the reference sequence, and $p \in \{0, 1, -1\}$ in which label 0 assigns a respective variant call $A_{i,p}$ to $H_0$ label 1 assigns the respective variant call to $H_1$, and label $-1$ assigns the respective variant call to the zygosity error condition $H_{-1}$;

(C) obtaining a plurality of sequence reads $\vec{O}$ for the biological sample, wherein the plurality of sequence reads $\vec{O}$ comprises at least 100,000 sequence reads and collectively represents at least 1000 different regions of the reference sequence, each respective sequence read $\vec{O}i$ in the plurality of sequence reads comprises a first portion that corresponds to a subset of the reference sequence and a second portion that encodes a respective barcode, independent of the reference sequence, for the respective sequence read, in a plurality of barcodes, and each respective sequence read $\vec{O}i$ in the plurality of sequence reads is $\in \{0, 1, -1, -\}^n$, wherein (i) n is the number of variant calls $A_{i,p}$, (ii) each respective label 0 for the respective sequence read $\vec{O}i$ assigns a corresponding variant call in $A_{i,p}$ to $H_0$, (iii) each respective label 1 for the respective sequence read $\vec{O}i$ assigns a corresponding variant call in $A_{i,p}$ to $H_1$, (iv) each respective label $-1$ for the respective sequence read $\vec{O}i$ assigns a corresponding variant call in $A_{i,p}$ to $H_{-1}$, and (v) each respective label $-$ for the respective sequence read $\vec{O}i$ indicates that the corresponding variant call in $A_{i,p}$ is not covered; and (D) refining a phasing vector result $\vec{X}$ by optimization of haplotype assignments at individual positions i in $A_{i,p}$ between $H_0$, $H_1$ and $H_{-1}$ for the plurality of sequence reads using an overall objective function:

$$\hat{X} = \underset{\vec{X}}{\mathrm{argmax}}\ P(\vec{X} \mid \vec{O}) = \frac{P(\vec{X})P(\vec{O} \mid \vec{X})}{C}$$

wherein, $$P(\vec{X}) = \prod_i \frac{(1-\varepsilon_i)}{2}(X_i = H_1) + (X_i = H_0) + \varepsilon_i(X_i = H_{-1}),$$

$\varepsilon_i$ is an estimate of incurring $H_{-1}$ at position i, $$P(\vec{O} \mid \vec{X}) = \prod_f P(O_{1,f}, \ldots, O_{N,f}),$$

$\hat{X}$ is the refined phasing vector result,
C is a constant,
$\vec{X}$ is the phasing vector result to be inferred, and
$(O_{1,f}, \ldots, O_{N,f})$ is the respective subset of N variant calls $A_{i,p}$ observed in the subset of sequence reads that include the same respective barcode form the plurality of barcodes, thereby phasing sequencing data of the test nucleic acid sample in the form of the refined phasing vector $\vec{X}$.

27. The non-transitory computer readable storage medium of claim 26, wherein $$(O_{1,f}, \ldots, O_{N,f} \mid \vec{X}, H_f=0) = \Pi_i P(O_{i,f} \mid A_{i,X_i}),$$

$$P(O_{1,f}, \ldots, O_{N,f} \mid \vec{X}, H_f=1) = \Pi_i P(O_{i,f} \mid A_{i,1-X_i}),$$

$$P(O_{1,f}, \ldots, O_{N,f} \mid \vec{X}, H_f=M) = \Pi_i 0.5,$$

M indicates a mixture of $H_f=0$ and $H_f=1$ for the respective barcode f, $$P(O_{i,f}, \ldots, O_{N,f} \mid \vec{X}) =$$

$$\frac{(1-\alpha)}{2}\left(\prod_i P(O_{i,f} \mid A_i, X_i) + \prod_i P(O_{i,f} \mid A_i, 1 - X_i)\right) + \alpha \prod_i 0.5,$$

$$\log P(O_{i,f} \mid A_{i,p}) = \sum_r 1(S_r = A_{i,p})(1 - 10^{-Q_r/10}) +$$

$$1(S_r \neq A_{i,p})(10^{-Q_r/10}) + 1(A_{i,p} = H_{-1})^{0.5}$$

$\alpha$ is a predetermined fractional value representing a likelihood or probability that $H_f=M$ arises, i is the $i^{th}$ variant in the respective subset of N variant calls observed for the subset of sequence reads that include the same respective barcode, r sums over the subset of sequence reads that include the same respective barcode, $1(S_r=A_{i,p})$ is an indicator function testing if the base assignment at position i in the $r^{th}$ sequence read $S_r$ in the subset of sequence reads that include the same respective barcode matches Ai,p, wherein when they match $1(S_r=A_{i,p})$ has a value of 1 and when they do not match $1(S_r=A_{i,p})$ has a value of zero, $1(S_r \neq A_{i,p})$ is an indicator function testing if the base assignment at position i in the $r^{th}$ sequence read $S_r$ in the subset of sequence reads that include the same respective barcode does not match Ai,p, wherein when they do not match $1(S_r \neq A_{i,p})$ has a value of 1 and when they do match $1(S_r=A_{i,p})$ has a value of zero, $1(A_{i,p}=H_{-1})$ is an indicator function that has a value of 1 when $A_{i,p}$ is equal to $H_{-1}$ and is a value of zero otherwise, and $Q_i$ is a quality value for $S_i$ for the read base at the position of i in the reference sequence.

28. The non-transitory computer readable storage medium of claim 26, wherein the plurality of sequence reads $\vec{O}$ comprises at least $1 \times 10^6$ sequence reads.

29. The non-transitory computer readable storage medium of claim 26, wherein the plurality of sequence reads $\vec{O}$ collectively represents at least 10,000 different regions of the reference sequence.

30. The non-transitory computer readable storage medium of claim 26, wherein the plurality of sequence reads $\vec{O}$ collectively represents at least $1 \times 10^6$ different regions of the reference sequence.

* * * * *